US009114228B2

(12) United States Patent
Zook et al.

(10) Patent No.: US 9,114,228 B2
(45) Date of Patent: Aug. 25, 2015

(54) DILATOR APPARATUS

(71) Applicant: Swan Valley Medical Incorporated, Bigfork, MT (US)

(72) Inventors: Ronald E. Zook, Bigfork, MT (US); Laurence K. Sampson, Denver, CO (US); Timothy E. Braun, Kalispell, MT (US); Kenneth A. High, Helena, MT (US); Steven W. Jackinsky, Denver, CO (US); Pete W. Kroehl, Denver, CO (US); Davey B. Palmer, Highlands Ranch, CO (US); David W. Wright, Littleton, CO (US); Paul P. Burek, Centennial, CO (US)

(73) Assignee: Swan Valley Medical Incorporated, Bigfork, MT (US)

( * ) Notice: Subject to any disclaimer, the term of this patent is extended or adjusted under 35 U.S.C. 154(b) by 462 days.

(21) Appl. No.: 13/738,832

(22) Filed: Jan. 10, 2013

(65) Prior Publication Data

US 2013/0123834 A1    May 16, 2013

Related U.S. Application Data

(60) Division of application No. 12/790,313, filed on May 28, 2010, now Pat. No. 8,382,785, which is a continuation-in-part of application No. 12/238,941, filed on Sep. 26, 2008, now Pat. No. 8,118,826, and a continuation-in-part of application No. 12/239,129, filed on Sep. 26, 2008, now Pat. No. 8,118,736.

(60) Provisional application No. 60/975,548, filed on Sep. 27, 2007, provisional application No. 61/038,457, filed on Mar. 21, 2008, provisional application No. 60/975,548, filed on Sep. 27, 2007, provisional application No. 61/038,457, filed on Mar. 21, 2008.

(51) Int. Cl.
| | |
|---|---|
| *A61M 29/00* | (2006.01) |
| *A61B 17/34* | (2006.01) |
| *A61B 17/00* | (2006.01) |
| *A61B 19/00* | (2006.01) |

(52) U.S. Cl.
CPC ............ *A61M 29/00* (2013.01); *A61B 17/3403* (2013.01); *A61B 17/3415* (2013.01); *A61B 17/3462* (2013.01); *A61B 2017/00278* (2013.01); *A61B 2017/00473* (2013.01); *A61B 2017/00477* (2013.01); *A61B 2017/3484* (2013.01); *A61B 2019/462* (2013.01)

(58) Field of Classification Search
CPC ........... A61B 17/0206; A61B 17/0218; A61B 17/0281; A61B 17/3403; A61B 17/3415; A61B 17/3439; A61B 17/3462; A61B 2017/3419; A61B 2017/3484; A61B 19/24; A61B 1/32; A61M 29/00
See application file for complete search history.

(56) References Cited

U.S. PATENT DOCUMENTS 5,857,999 A * 1/1999 Quick et al. ................... 604/107
5,882,340 A * 3/1999 Yoon ......................... 604/164.12

(Continued)

*Primary Examiner* — Sarah W Aleman
(74) *Attorney, Agent, or Firm* — John R. Ley

(57) ABSTRACT

A cystotomy apparatus includes a sound from which an advancement device having a cutting tip creates a surgical pathway from the bladder through abdominal tissue to the external abdomen along a predetermined path. The cutting tip is captured and removed from the advancement device in a capture cup located in the predetermined path by an alignment structure. The cutting tip is removed from the advancement device while within the capture cup, to allow a dilator, cannula or catheter to be drawn through the surgical pathway into the bladder.

10 Claims, 37 Drawing Sheets

(56) References Cited

U.S. PATENT DOCUMENTS

| | | | |
|---|---|---|---|
| 6,451,042 B1* | 9/2002 | Bonutti | 606/190 |
| 7,374,534 B2* | 5/2008 | Dalton | 600/222 |
| 7,491,168 B2* | 2/2009 | Raymond et al. | 600/231 |
| 7,758,501 B2* | 7/2010 | Frasier et al. | 600/233 |
| 7,946,982 B2* | 5/2011 | Hamada | 600/233 |
| 7,959,610 B2* | 6/2011 | Elbert et al. | 604/164.01 |
| 2007/0203399 A1* | 8/2007 | Gephart et al. | 600/219 |
| 2008/0242930 A1* | 10/2008 | Hanypsiak et al. | 600/114 |

* cited by examiner

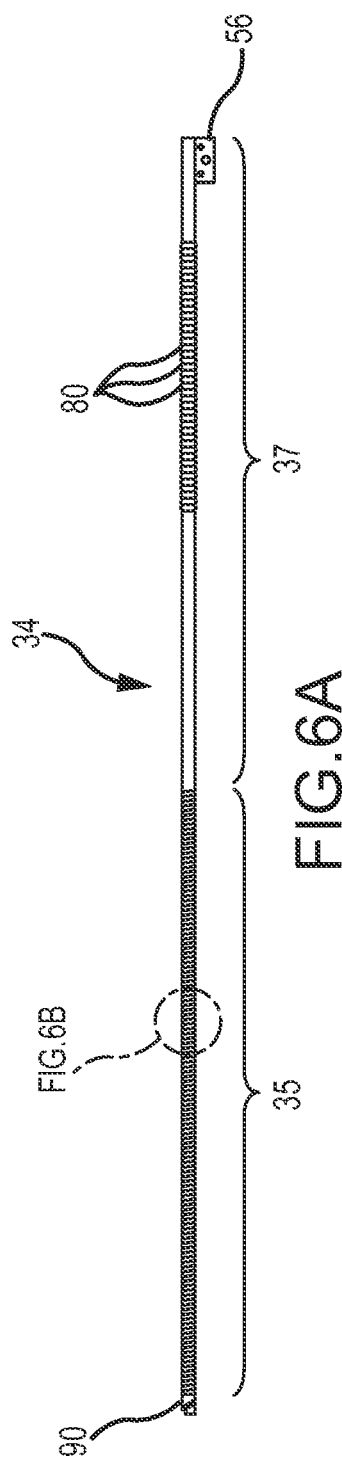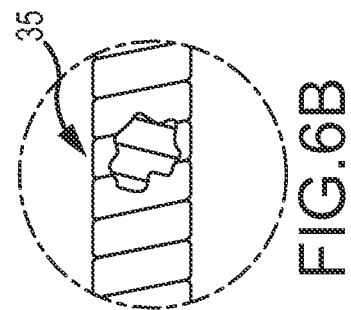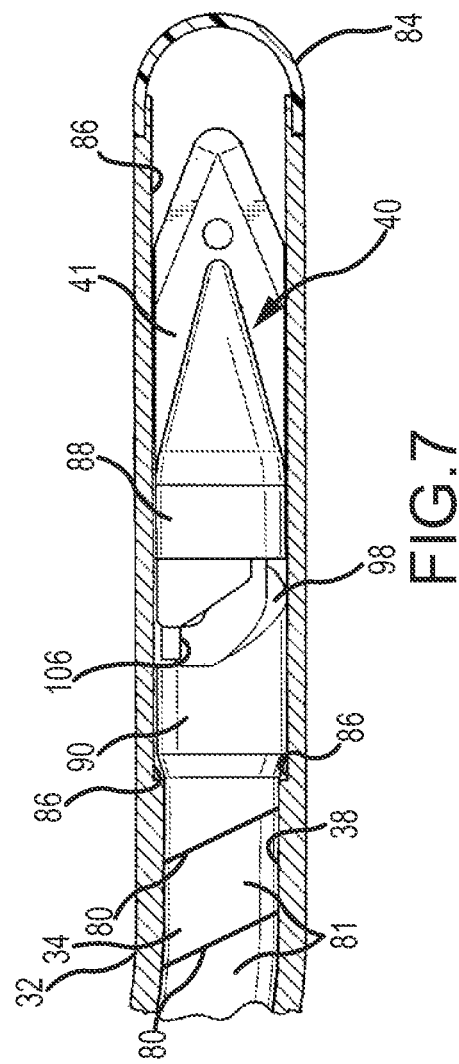

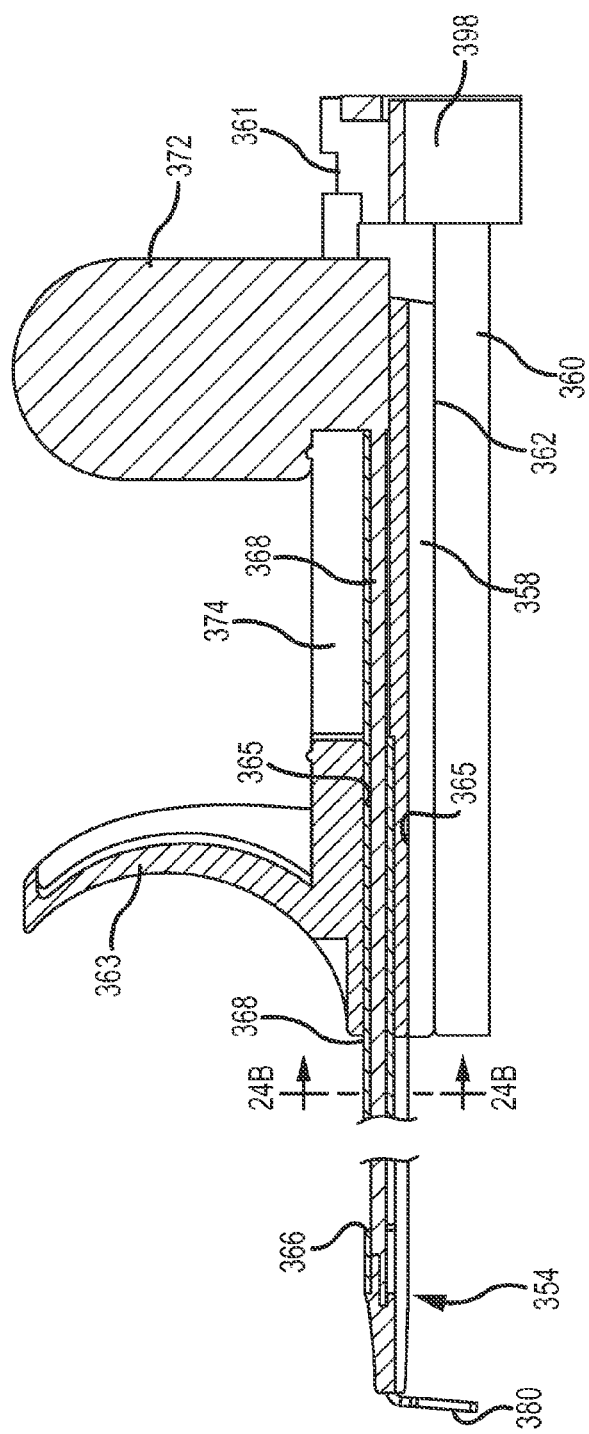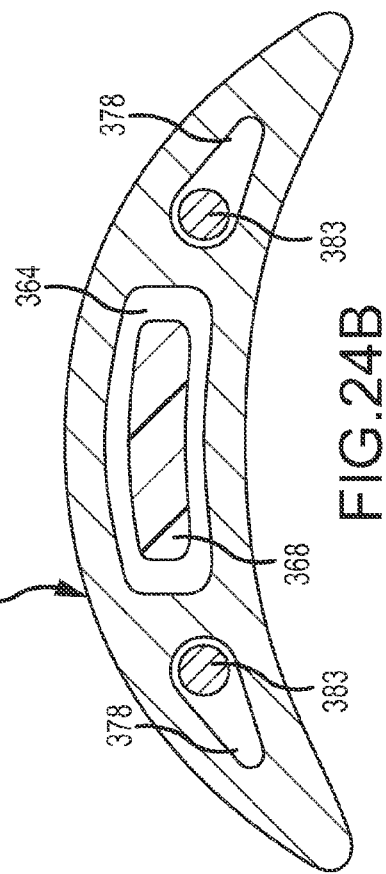

DILATOR APPARATUS

CROSS REFERENCE TO RELATED APPLICATIONS

This is a division of U.S. application Ser. No. 12/790,313, filed May 28, 2010, now U.S. Pat. No. 8,382,785. U.S. application Ser. No. 12/790,313 is a continuation in part of U.S. application Ser. No. 12/238,941, filed Sep. 26, 2008, now U.S. Pat. No. 8,118,826. U.S. application Ser. No. 12/790,313 is also a continuation in part of U.S. application Ser. No. 12/239,129, filed Sep. 26, 2008, now U.S. Pat. No. 8,118,736. Application Ser. Nos. 12/790,313, 12/238,941 and 12/239,129 claim priority to U.S. provisional application 60/975,548, filed Sep. 27, 2007 and to U.S. provisional application 61/038,457, filed Mar. 21, 2008. The subject matter of all of these prior applications is fully incorporated herein by this reference.

FIELD OF THE INVENTION

This invention relates to creating, maintaining and using a surgical pathway between the bladder and the exterior abdomen of a patient. More particularly, the present invention relates to a new and improved apparatus and method for performing a cystotomy for medical procedures such as inserting a cannula to facilitate surgical access to the bladder or inserting a catheter to facilitate urine drainage, in a manner which minimizes trauma experienced by the patient and promotes efficiently performing the procedure.

BACKGROUND OF THE INVENTION

A cystotomy is a surgical procedure which cuts or forms a surgical pathway between the bladder and the exterior abdomen through the intervening abdominal tissue. A cystotomy establishes access to the interior of the bladder. A cannula is inserted into the surgical pathway to create an access pathway for inserting medical instruments into the bladder. A variety of different medical procedures can be performed inside the bladder using the instruments inserted through the cannula.

A cystostomy is a surgical procedure which cuts or forms a surgical pathway between the bladder and the exterior abdomen through the intervening abdominal tissue for the purpose of establishing an additional urine drainage pathway from the bladder, such as when the urine flow path through the natural urinary canal is inhibited or obstructed. Once the surgical pathway has been formed, a hollow tubular urine drainage catheter is inserted in the surgical pathway. Urine is drained from the bladder through the catheter. The catheter initially remains in place long enough for the surrounding tissue to form a tract or sinus between the bladder and the exterior abdomen. Thereafter, the catheter is replaced periodically in order to help prevent infection. A cystostomy is typically required when urine flow is blocked by swelling of the prostate (benign prostatic hypertrophy), traumatic disruption of the urethra, congenital defects of the urinary tract, obstructions such as kidney stones passed into the urethra, or cancer. A cystostomy is also a common treatment used among spinal cord injury patients who are unable or unwilling to use intermittent catheterization to empty the bladder and cannot otherwise void due to detrusor sphincter dyssynergia.

In both a cystotomy and a cystostomy, a surgical pathway is created between the bladder and the exterior abdomen through the intervening abdominal tissue. Because of the common aspects of forming the surgical pathway, the term "cystotomy," as used herein, will refer to forming the surgical pathway between the bladder and the exterior abdomen through the intervening abdominal tissue, regardless of whether a catheter is inserted in the surgical pathway as an auxiliary urine drainage passageway or a cannula is inserted in the surgical pathway to receive and accept surgical instruments for performing a medical procedure within the bladder.

There are two general techniques for performing a cystotomy. An "outside-in" cystotomy, sometimes referred to as a percutaneous cystotomy, is performed by cutting the surgical pathway from the exterior abdomen through the intervening abdominal tissue into the bladder. An "inside-out" cystotomy is sometimes referred to as a transurethral cystotomy because access to the interior of the bladder is achieved through the urinary canal. An inside-out a cystostomy is performed by cutting the surgical pathway from the bladder through the intervening abdominal tissue to the exterior abdomen.

An outside-in cystotomy typically involves the insertion of a needle from the exterior abdomen to inside the bladder. The insertion of the needle through the abdomen creates a surgical pathway into the bladder. A sheath surrounding the needle is kept within the surgical pathway when the needle is removed. Outside-in cystotomies are suitable for draining urine from the bladder, but are not typically suitable for performing medical procedures within the bladder because the small diameter size of the sheath is insufficient to accommodate medical instruments. One difficulty or disadvantage associated with outside-in cystostomies is the potential to puncture through the posterior wall of the bladder creating fistulas.

An inside-out cystotomy involves the use of a medical instrument called a sound. The sound is inserted through the urinary tract and is pushed against the bladder. The surgical pathway is then formed by forcing the sound from the bladder through the intervening tissue to the external abdomen. An inside-out cystotomy is generally considered a blind procedure because the surgeon lacks a precise visual indication of the location of the end of the sound within the bladder, unless a bulge on the abdomen can be created. It is typically impossible to tent or bulge the exterior abdomen of obese patients, because of the excess abdominal tissue. Instead, the surgeon generally must rely on personal skill and experience to position the sound and predict the location where the cutting blade will emerge.

All cystotomies carry some risk of complication. Potential complications from performing a cystotomy involve accidentally cutting the intestine. The intestines are located very close to the location where the surgical pathway is normally established. Furthermore, different patients have slightly different anatomies which makes it difficult to predict exactly the location of the intestines in the intervening tissue between the bladder and the external abdomen, particularly in the case of obese patients. Generally, imaging is not used during the procedure. The dangers from infection due to even a small and unintentional cut of the intestine are substantial, and a not-insignificant number of such incidents can result in death. Nevertheless, a cystotomy may be the only option for use with some patients who have greater risks of other medical problems resulting from not performing the cystotomy, or a cystotomy may be required or desirable as part of another surgical procedure.

To minimize the possibility of inadvertently cutting the intestine and to otherwise reduce tissue trauma, and because the sound must have a size capable of being inserted through the urinary tract, the cutting tip used to create the surgical pathway is relatively small in size. The small size helps to reduce the possibility of cutting adjacent tissues, such as the intestines. If a cannula is to be inserted within the surgical pathway, the surgical pathway must be expanded to accept the larger cannula. It is desirable to expand the size of the initial surgical pathway without unduly tearing the tissue and without inducing more trauma. It is also desirable to facilitate the use of medical equipment to perform the cystotomy, thereby reducing the time duration of the medical procedure and the trauma to the patient.

Additionally, known instruments currently available for use in cystotomies have no capability for effectively securing the bladder wall during the procedure, allowing for the possibility that the flaccid wall of the bladder may impede the procedure.

SUMMARY OF THE INVENTION

The present invention involves improvements in the medical equipment used to perform a cystotomy, thereby improving the chances of a successful medical result while minimizing trauma to the patient and minimizing risks to the medical personnel who perform the procedure. The new and improved features of the apparatus and methodology described herein enhance the accuracy of creating the surgical pathway at the desired location, facilitate the maintenance and expansion of the surgical pathway after it has been created, secure the bladder wall to avoid impeding the procedure, minimize risks to the surgeon and medical personnel of being accidentally cut by the cutting tip, permit the insertion of a dilator and cannula into the surgical pathway with greater ease to the surgeon and less trauma to the patient, provide more reliable indications of the extent of movement required to cut the surgical pathway and to insert a dilator and a cannula, minimize additional cutting or tearing of patient tissue surrounding the surgical pathway while expanding the surgical pathway, maintain the distal tip of the sound within the bladder and within the surgical pathway, maintain the dilator and cannula in the surgical pathway without permitting inadvertent movement out of the surgical pathway, avoid accidentally allowing the surgical pathway to close after it has been created, and generally facilitate better and more effective cystotomies, among other things.

In accordance with these and other features, one aspect of this invention relates to a cystotomy apparatus for creating a surgical pathway from a bladder through abdominal tissue to an exterior abdomen. The cystotomy apparatus includes a sound for insertion through a urinary tract into the bladder. The sound defines a passageway which extends from its distal end to its proximal end. A handle portion is connected to the proximal end of the sound at a position which remains exterior to the urinary tract. The handle portion is adapted for manipulating the distal end of the sound adjacent to a position where the surgical pathway is to be created. A cutting tip having a blade for cutting through tissue to create the surgical pathway is connected to an advancement device by the complementary interaction of a cutting tip connector on the cutting tip and an advancement device connector on the advancement device. The advancement device is longitudinally moveable within the passageway of the sound. The distal end of the sound extends the distal end of the advancement device and the connected cutting tip in a predetermined path from the distal end of the sound when the surgical pathway is created. A capture cup has a containment area for receiving and holding the cutting tip. An alignment structure is connected to the handle portion and includes a retaining portion for releasably retaining the capture cup at a position exterior to the abdomen in alignment with the predetermined path. Retained in this manner, the containment area of the capture cup receives the cutting tip after the surgical pathway has been created by longitudinal movement of the advancement device and the connected cutting tip.

Subsidiary features of the cystotomy apparatus of the invention include bayonet style connections formed by the advancement device connector and cutting tip connector, an adjustable portion of the alignment structure to adjust the position of the capture cup along the predetermined path relative to the distal end of the sound, a bayonet style connection between the retention portion of the alignment structure and the capture cup to detach the capture cup from the retaining portion while simultaneously detaching the alignment structure connector and the cutting tip connector, an elastomeric lining within containment area of the capture cup to frictionally engage the cutting tip upon movement of the cutting tip into the containment area and to transfer rotational force from the capture cup to the cutting tip through the elastomeric lining to detach the cutting tip from the distal end of the advancement device, a lock wire longitudinally moveable within the internal passageways of the advancement device connector and the cutting tip connector to separate an alternative embodiment of the connectors, an inflatable balloon positioned at the distal end of the sound which in an inflated state protrudes radially outward from the distal end of the sound a sufficient distance to impede the distal end of the sound from moving into the surgical pathway, a metal ribbon wound in a longitudinally extending helical coil to form a portion of the advancement device, a plurality of rods positioned within an internal passageway defined by the helical coil to enhance transfer force capability of the advancement coil when moving longitudinally to create the surgical pathway, a gap which separates adjacent portions of a semicircular wall structure of the retention portion of the alignment structure through which distal end of the advancement device may be passed without disconnecting the alignment structure from the handle, an annular groove around the capture cup to receive the semicircular wall structure of the retention portion to retain the capture cup, a rounded end piece attached to the distal end of the sound which covers the passageway of the sound and facilitates movement of the distal end of the sound through the urinary tract and through which the blade of the cutting tip cuts upon longitudinal advancement of the cutting tip out of the distal end of the passageway of the sound, and an inverted funnel shape located in the capture cup to direct the cutting tip into the containment area after the surgical pathway is created.

Other subsidiary features involve using a dilator in combination with the cystotomy apparatus. The dilator is inserted into the surgical pathway. The dilator includes a stylet which has a stylet connector at a distal end that is adapted to connect with the advancement device connector after removal of the cutting tip. The advancement device is moved in a proximal longitudinal direction to move the dilator and the connected stylet through the surgical path until the stylet connector and the advancement device connector are located within the bladder, at which point the stylet disconnects the stylet connector from the device connector within the bladder.

Other subsidiary features involve using a cannula in combination with the dilator after the dilator is located in the surgical pathway. The cannula includes a cannula tube which defines an internal passageway for inserting and manipulating medical instruments. An obturator includes a shaft adapted to be removably received within the internal passageway of the cannula tube by insertion through a center opening of the dilator. The dilator operatively expands to accommodate the cannula tube and the shaft of the obturator as the cannula and the obturator are moved into the center opening of the dilator, thereby expanding the surgical pathway.

Another aspect of the invention relates to a method of creating the surgical pathway using the cystotomy apparatus. The method involves inserting the sound through the urinary tract until a distal end of the sound abuts the bladder at a position where the surgical pathway is to be created, adjusting the alignment structure to position the capture cup on the external abdomen in alignment with the predetermined path, longitudinally moving the advancement device and the connected cutting tip through the bladder and the abdominal tissue to the external abdomen to create the surgical pathway, continuing longitudinally moving the advancement device until the cutting tip is received within the capture cup, disconnecting the capture cup from the alignment structure, and disconnecting the cutting tip from the advancement device while the cutting tip is retained within the capture cup.

Subsidiary features of the method of forming the surgical pathway include disconnecting the capture cup from the alignment structure simultaneously with disconnecting of the cutting tip from the advancement device, retaining the distal end of the sound to avoid projecting the distal end of the sound into the surgical pathway by inflating an inflatable balloon on a distal end of the sound when the distal end of the sound is within the bladder and before the advancement device and connected cutting tip are longitudinally moved to create the surgical pathway, removing the alignment structure from the connected relationship with the handle portion of the sound by passing equipment extending into the surgical pathway through a gap in the retaining portion of the alignment structure, determining the distance from the bladder through the abdominal tissue to the external abdomen along which the surgical pathway is created by reference to indicia formed on the alignment structure, and longitudinally moving the advancement device and the cutting tip to create the surgical pathway by a distance at least equal to the distance from the bladder through the abdominal tissue to the external abdomen by reference to indicia formed on the sound.

Another aspect of the method of creating a surgical pathway involves expanding the surgical pathway using the dilator, by extending the stylet through the dilator, connecting the stylet connector to the advancement device connector after removing the cutting tip, and longitudinally moving the advancement device to move the connected stylet and dilator into the surgical pathway. A further subsidiary aspect involves determining the length of the surgical pathway from the bladder through the abdominal tissue to the external abdomen by reference to indicia formed on the alignment structure, and longitudinally moving the advancement device with the connected stylet by a distance at least equal to the distance from the bladder through the abdominal tissue to the external abdomen by reference to indicia formed on the dilator.

A further aspect of the method of creating the surgical pathway involves inserting a cannula in the dilator, by removing the stylet from the dilator after the dilator has been positioned within the surgical pathway, inserting an obturator into a cannula tube of a cannula, inserting a distal end of the cannula tube with the obturator inserted into the cannula tube into the dilator after the dilator has been positioned within the surgical pathway, expanding the surgical pathway by insertion of the cannula tube and obturator into the dilator, and removing the obturator from the cannula. A further subsidiary feature of this aspect of the method involves inserting a medical instrument through the cannula tube from the exterior of the patient and into the bladder, and performing a medical procedure within the bladder using the medical instrument inserted through the cannula tube.

Another aspect of the invention involves a dilator for inserting a cannula into a surgical pathway extending between a bladder and an external abdomen. The dilator includes a body which is located outside of the abdomen. A ring portion of the body defines a central opening about a central axis through which the cannula is inserted. A plurality of arm receivers are connected to the ring portion on opposite sides of the central axis. A plurality of substantially straight and elongated arms are connected to and extend distally from each arm receiver. Each arm has a central passageway which extends substantially along the length of the arm. Each arm defines a window into the central passageway facing outward from the central axis at a position adjacent to the distal end of each arm. A longitudinal tab member is positioned within the central passageway of each arm. The longitudinal tab member extends from a distal end located at the distal end of the arm past the window to a proximal end located in the arm receiver. A wing member is attached to the proximal end of the longitudinal tab member. The wing member is movably positioned in a longitudinally extending slot formed in the arm receiver. The wing member is movable in the slot in distal and proximal directions to move the portion of the longitudinal tab member which is proximal to the window in distal and proximal directions within the central passageway. A portion of the longitudinal tab adjacent to the window including stress risers adjacent to deflection portions of the longitudinal tab member. The stress risers direct the deflection portions to protrude outwardly through the window upon longitudinal distal movement of the longitudinal tab member by the wing member and to withdraw the deflection portions into the window upon longitudinal proximal movement of the longitudinal tab member by the wing member. The central passageway of each arm extend substantially straight between the window and the proximal end of each arm. The proximal and distal movement of the wing member in the slot occurring in substantially straight alignment with the portion of the longitudinal tab member extending in the center passageway of each arm.

Other subsidiary features of the dilator of the present invention include indicia formed at intervals along at least one arm to indicate the depth of movement of the dilator into the surgical pathway, a loop connected at distal end of the arms on opposite sides of the central axis with each loop extending toward the central axis and the loops occupying respectively different longitudinal positions on the arms to allow the loops to overlap upon transverse inward deflection of the arms toward the central axis.

Another aspect involves combining the dilator with a stylet which comprises a shaft having a longitudinal length that is greater than the length of the arms of the dilator. A stylet connector is formed on a distal end of the shaft to releasably connect with a complementary connector of a device located in the surgical pathway. The shaft of the stylet extends through the center opening along the central axis with the distal end of the shaft of the stylet extending through the overlapped loops on the distal ends of the arms to hold the arms deflected transversely inwardly during insertion of the dilator in the surgical pathway. Subsidiary features of the dilator include side cavities formed on opposite transverse sides of the central passageway, and forming the loops by a wire curved in the form of a loop having ends extending into the side cavities. The ends of the wire extend substantially the entire length of each arm. A knob at a proximal end of the shaft of the stylet includes a connector which connects in a complementary manner with a connector on the ring portion, upon insertion of the stylet through the center opening and the distal end of the shaft through the overlapped loops. The complementary connectors between the knob and the ring portion and between the distal end of the shaft and the device in the surgical pathway release from one another by movement of the knob relative to the ring portion.

Another aspect of the invention involves combining the dilator with the cannula. The cannula comprises a cannula tube which defines an internal passageway for inserting and manipulating medical instruments. An obturator includes an obturator shaft which is adapted to be removably received within the internal passageway of the cannula tube. The obturator shaft has a distal end of tapered and rounded shape which protrudes beyond the distal end of the cannula tube. The center opening of the dilator receives the cannula tube and the obturator inserted within the cannula tube, causing the arms of the dilator to expand transversely to accommodate the cannula tube and the obturator shaft as the cannula and the obturator move distally into the center opening of the dilator. The expansion of the arms to accept the cannula and the obturator also expanding the surgical pathway. Subsidiary feature involves a proximal body portion of the cannula having a complementary connector for connecting with a connector on the ring portion of the dilator upon insertion of the cannula through the center opening of the dilator.

A more complete appreciation of the present invention and its scope may be obtained from the accompanying drawings, which are briefly summarized below, from the following detailed description of presently preferred embodiments of the invention, and from the appended claims.

BRIEF DESCRIPTION OF THE DRAWINGS

FIG. 6A is a side elevational view of the advancement device showing an advancement coil connected to an advancement rod.

FIG. 6B is an expanded portion of the advancement device shown in FIG. 6A, with a portion broken out.

FIG. 7 is a partial longitudinal cross-sectional view of a sound of the apparatus shown in FIG. 1, showing a cutting tip connected to the advancement coil located at a distal end of the sound.

FIG. 17 shows inserting the sound through the urinary tract into the bladder;

FIG. 18 shows pressing the distal end of the sound against the bladder and tissue between the bladder and the exterior abdomen along with the guide arm and capture cup above a tented or bulged area of the exterior abdomen;

FIG. 19 shows moving the guide arm downward along the mast to position the capture cup on the exterior abdomen at the tented or bulged location;

FIG. 20 shows expanding a balloon on the distal end of the sound to maintain the distal end of the sound within the bladder and preventing it from entering the surgical pathway;

FIG. 21 shows advancing the cutting tip from the distal end of the sound through the bladder into the tissue between the bladder and the external abdomen while creating the surgical pathway; and FIG. 22 shows completion of the surgical pathway by advancement of the cutting tip into the capture cup and rotation of the capture cup to remove it from the guide arm and to remove the cutting tip from the advancement coil.

FIG. 24A is a longitudinal cross-sectional view of an arm of the dilator shown in FIG. 23.

FIG. 24B is a transverse cross-sectional view of the arm shown in FIG. 24A, taken substantially in the plane of line 24B-24B.

FIG. 26 shows the dilator and stylet connected to the advancement coil of the sound of the apparatus shown in FIG. 1;

FIG. 27 shows moving the dilator and stylet into the surgical pathway by retraction of the advancement coil;

FIG. 28 shows anchoring the distal end of the dilator in the bladder;

FIG. 29 shows disconnecting the dilator and stylet from the advancement coil within the bladder;

FIG. 30 shows the dilator and stylet in the surgical pathway after removal of the sound from within the bladder and urinary tract;

FIG. 31 shows removing the stylet from the dilator; and

FIG. 32 shows the dilator anchored in the bladder after removing the stylet.

FIG. 36 shows inserting the connected cannula and obturator into the dilator during expansion of the surgical pathway;

FIG. 37 shows the connected cannula and obturator fully inserted into the dilator and complete expansion of the surgical pathway; and FIG. 38 shows removing the obturator from the dilator.

DETAILED DESCRIPTION

Figure 1:
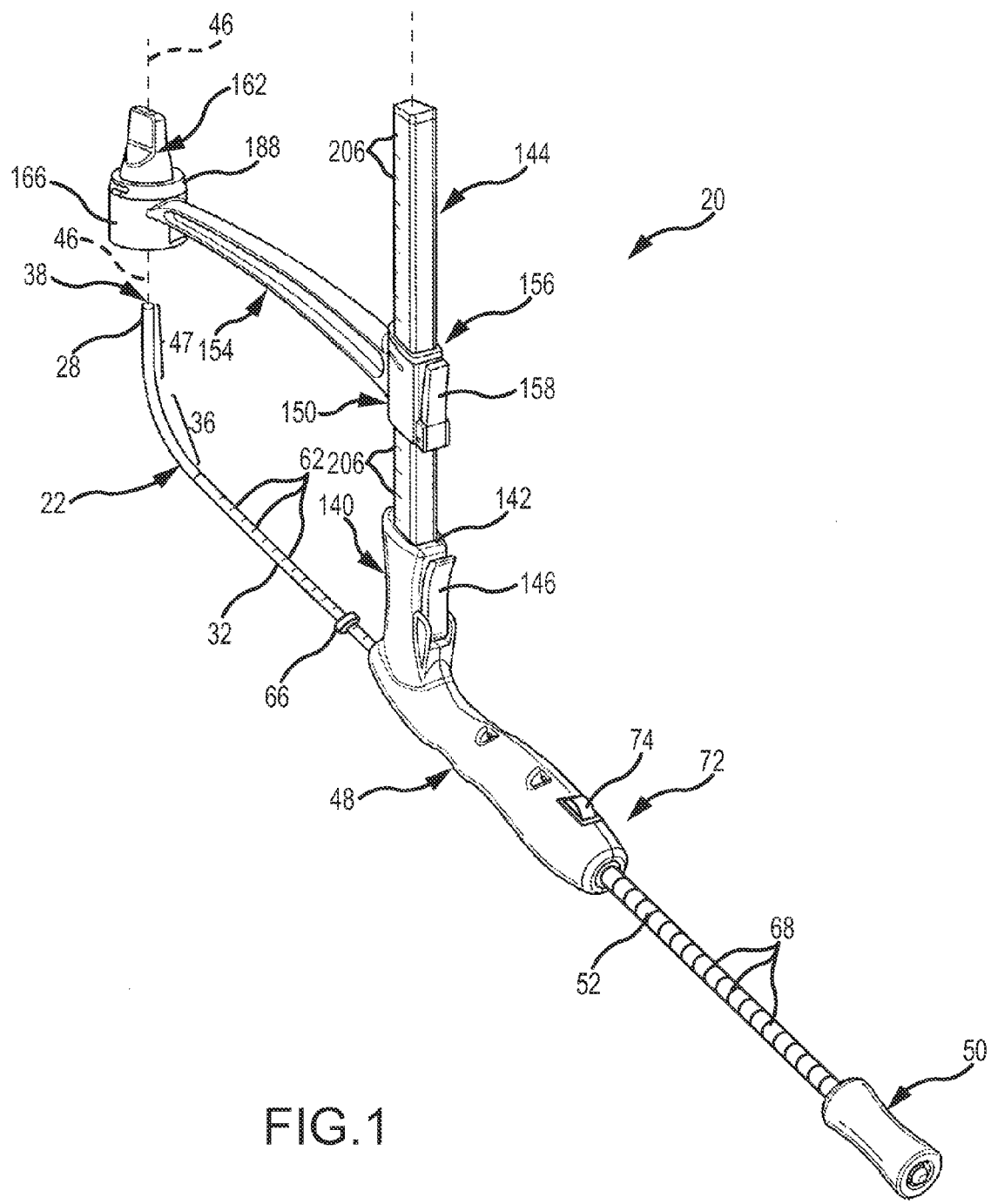
FIG. 1 is a perspective view of a suprapubic cystotomy apparatus of the present invention.
Figure 2:
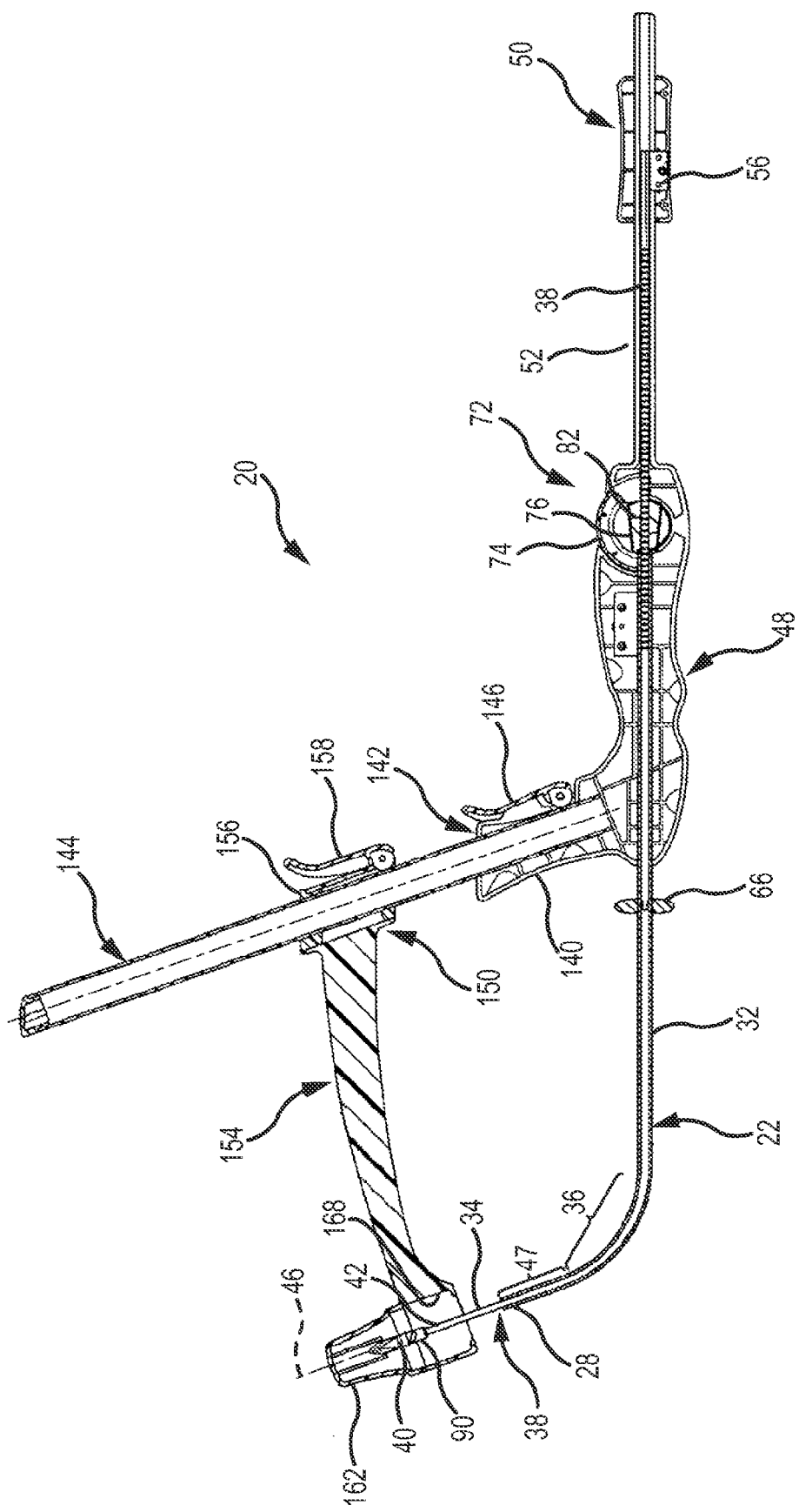
FIG. 2 is a longitudinal cross-sectional view of the apparatus shown in FIG. 1.

A cystotomy apparatus 20 which embodies a portion of the present invention is shown in FIGS. 1 and 2. The apparatus 20 is used to perform a cystotomy (FIGS. 17-22) and related procedures (FIGS. 26-29) on a patient. A sound 22 of the apparatus 20 is inserted though a urethra or urinary tract 24 and into a bladder 26 of the patient (FIGS. 17-22, 26-32, 36-38, 40 and 41). The surgeon manipulates a proximal portion of the apparatus 20 to position a distal end 28 of the sound against the bladder 26 at a location where a surgical pathway 29 (FIGS. 21 and 22) is cut from the bladder 26 through intervening tissue to an external abdomen 30 of the patient (FIGS. 17-22).

The relative terms "proximal" and "distal" are used herein to describe aspects of the apparatus 20 in relation to the medical practitioner who inserts the sound 22 into the urinary tract 24 at the exterior opening of the urinary tract 24. Accordingly, the portions of the apparatus 20 which are the most internal within the patient and are therefore more removed from the surgeon are referred to as "distal," and the portions of the apparatus 20 which are closest to the exterior opening of the urinary tract 24 and the surgeon are referred to as "proximal." This same convention applies with respect to those portions of the apparatus 20 which are not within the urinary tract 24, (e.g. guide arm 154) in the sense that those external portions which are more removed from the surgeon are referred to as "distal" and the portions which are closer to the surgeon are referred to as "proximal."

The sound 22 comprises a rigid hollow tube 32 which contains an advancement device 34. The advancement device 34 is shown in greater detail in FIG. 6, and includes a distal advancement coil 35 which is welded to a proximal advancement rod 37. The rigid hollow tube 32 has a moderate curved portion 36 close to the distal end 28. The curved portion 36 facilitates directing the distal end 28 of the sound 22 into an advantageous position where the surgical pathway 29 is to be created, in conformance with the anatomy of the patient. The advancement device 34 is axially moveable within a center passageway 38 of the tube 32. The advancement coil 35 is flexible enough to bend around the curved portion 36 of the rigid hollow tube 32, when the advancement device 34 is advanced and retracted within the tube 32. The characteristics of the advancement coil 35 limit the contraction of the advancement coil 35 in an axial or longitudinal direction, despite its flexibility in a transverse direction. The advancement rod 37 of the advancement device is straight and rigid. The advancement rod 37 does not enter or move within the curved portion 36 of the rigid hollow tube 32, when the advancement device is moved longitudinally in the center passageway 38 of the tube 32.

Figure 18:
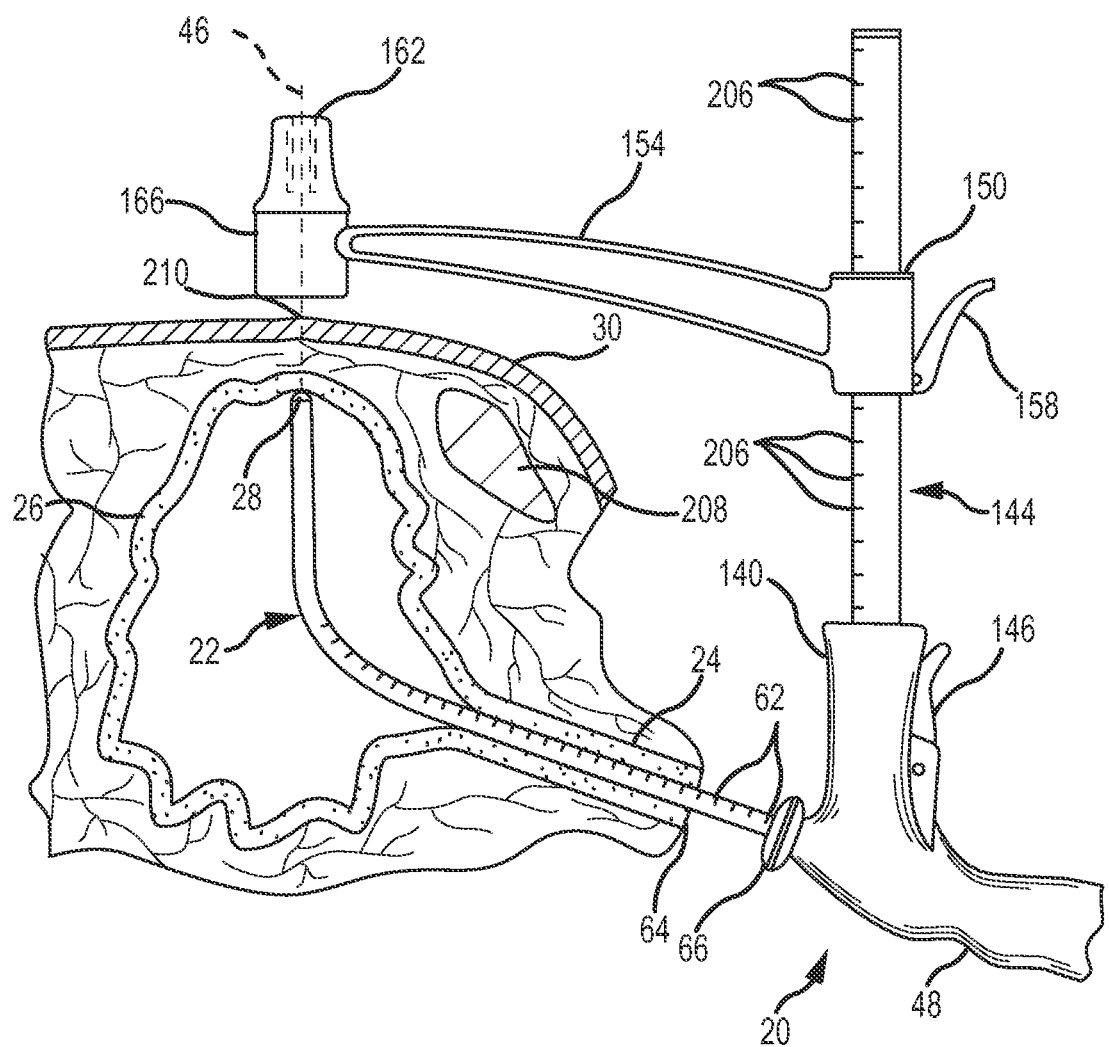

A cutting tip 40 is attached to a distal end 42 of the advancement coil 35. The cutting tip 40 includes a blade 41 (FIGS. 7 and 8) which cuts through the intervening tissue between the bladder 26 and the exterior abdomen 30. The cutting tip 40 is advanced out of the distal end 28 of the sound 22 and is pushed through the bladder 26, the intervening tissue and out of the external abdomen 30 to create the surgical pathway 29 (FIGS. 21 and 22), after the distal end 28 of the sound 22 is positioned against the bladder 26 (FIG. 18). Force is applied to the proximal end of the advancement device 34 at the proximal end of the apparatus 20 outside of the patient, to advance the advancement device 34 through the rigid hollow tube 32 and force the cutting tip 40 through the tissue to create the surgical pathway 29. The cutting tip 40 moves along a path 46 which extends generally in alignment with a straight portion 47 of the tube 22 which is located between the curved portion 36 and the distal end 28 of the sound 22. The advancement coil 35 is sufficiently rigid in the transverse dimension to maintain the distal end 42 aligned and coaxial with the path 46 when advanced the distal end 42 is advanced from the distal end 28 of the sound 22 and the cutting tip 40 is pushed through the bladder 26, the intervening tissue and out of the external abdomen 30.

The sound 22 is connected to a proximal portion of the apparatus 20 which is located outside of the urinary tract 24. The proximal portion of the apparatus which is located exterior of the patient includes a front handle 48 and a rear handle 50. The surgeon grasps one or both of the handles 48 and 50 when manipulating the sound 22 in the urinary tract 24 and the bladder 26.

Figure 3:
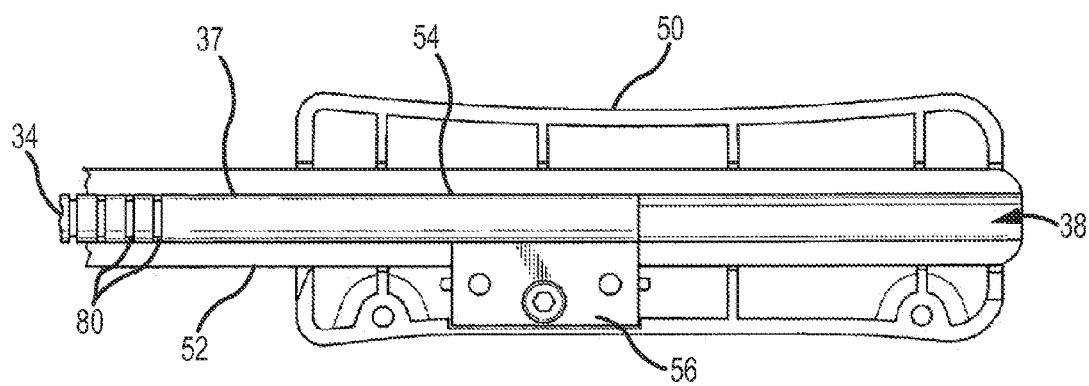
FIG. 3 is a longitudinal cross-sectional view of a rear handle and its connection to an advancement device of the apparatus shown in FIG. 1.
Figure 4:
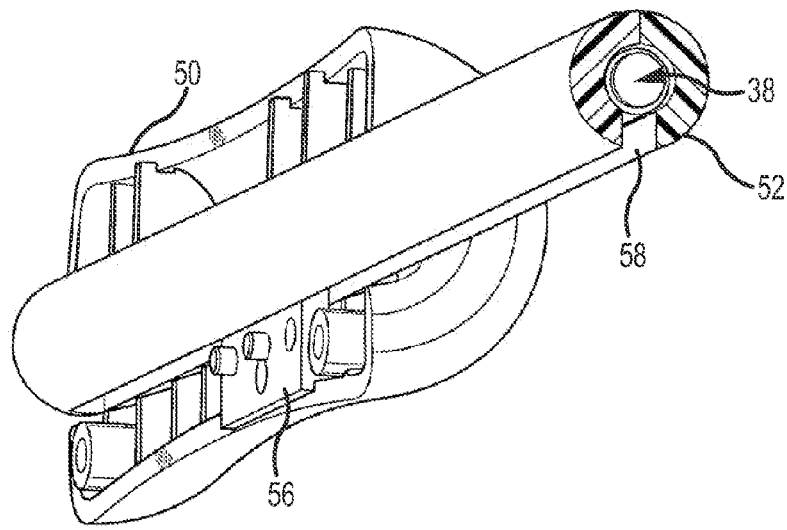
FIG. 4 is a partial perspective and sectioned view of the rear handle shown in FIG. 3.

The rear handle 50 is slidably mounted on a tubular body 52 which extends proximally from the front handle 48. The passageway 38, which contains the advancement device 34, extends from the distal end 28 of the sound, through the front handle 48 and through the tubular body 52. A proximal end 54 of the advancement rod 37 is connected to a connector plate 56 within the rear handle 50, as shown in FIGS. 3 and 4. A narrow slot 58 extends along the tubular body 52 and creates enough clearance for the connector plate 56 to extend into the passageway 38 where it is connected to the proximal end of the advancement rod 37, while allowing the rear handle 50 to move along the tubular body 52. The rear handle 50 is moved toward and away from the front handle 48 to advance and retract the advancement device 34 within the passageway 38, respectively. The extension and retraction of the advancement device 34 extends and retracts the cutting tip 40 relative to the distal end 28 of the sound 22. The connector plate 56 residing within the slot 58 prevents the rear handle 50 from rotating relative to the tubular body 52.

Indicia 62 are formed on the sound 22 to indicate distance from the distal end 28 of the sound 22, as shown in FIG. 1. The indicia 62 are used to determine the length of the sound 22 which is inserted into the urinary tract 24 (FIGS. 17-22), by observing the indicia 62 closest to an exterior opening 64 of the urinary tract 24. To facilitate identifying the length of the sound 22 inserted into the urinary tract 24 and bladder 26, an indicator slide 66 is moved adjacent to the external opening 64 of the urinary tract 24 (FIG. 20). Movement of the indicator slide 66 to the position adjacent the external opening 64 allows the surgeon to readily determine whether the position of the sound within the urinary tract 24 and bladder 26 has changed from the initial desired position during the course of the procedure.

Indicia 68, shown in FIG. 1, are formed on the tubular body 52 to indicate a distance that the cutting tip 40 has been extended from the distal end 28 of the sound 22. The distance that the cutting tip 40 is extended from the distal end 28 of the sound 22 is determined by observing the location of the rear handle 50 relative to the indicia 68 before distal movement of the rear handle 50 to advance the advancement device 34 and the connected cutting tip 40, observing the location of the rear handle 50 relative to the indicia 68 during the distal movement of the rear handle 50, and determining the difference between the two indicia. The difference between the two indicia represents the amount of advancement of the cutting tip 40. The ability to determine the amount of advancement of the cutting tip 40 is important in determining whether the cutting tip 40 has created a surgical pathway of sufficient length to extend from the bladder 26 to the external abdomen 40.

Figure 5A:
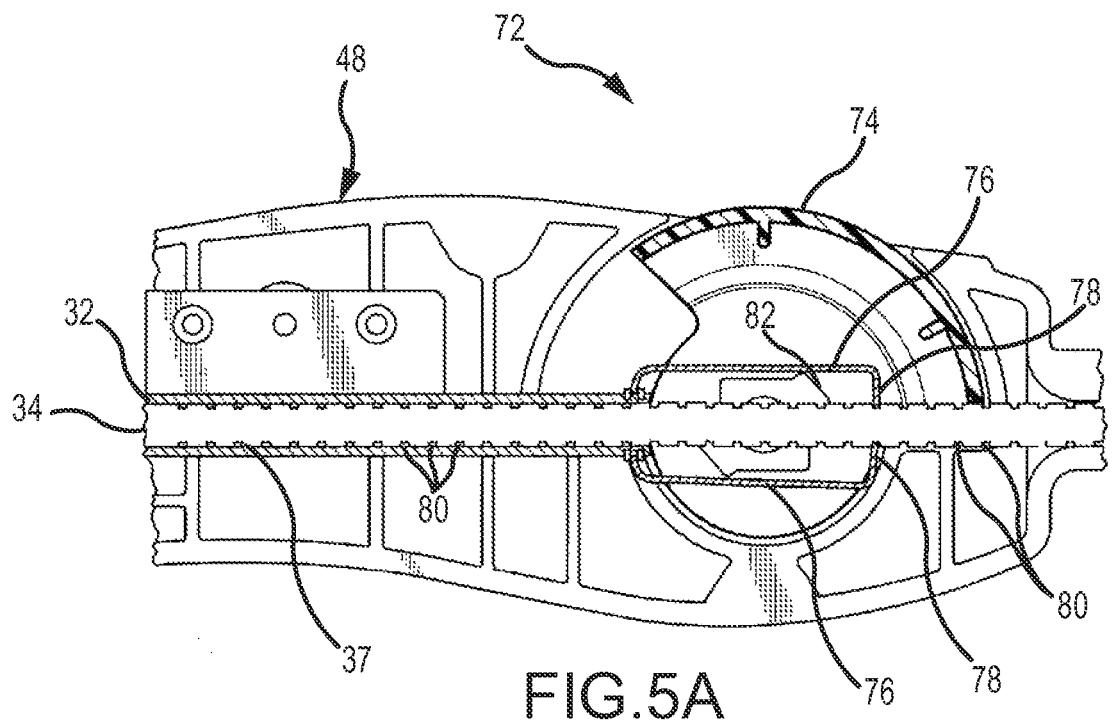
FIG. 5A is a longitudinal cross-sectional view of a front handle and a locking mechanism of the apparatus shown in FIG. 1, shown in a locked position.
Figure 5B:
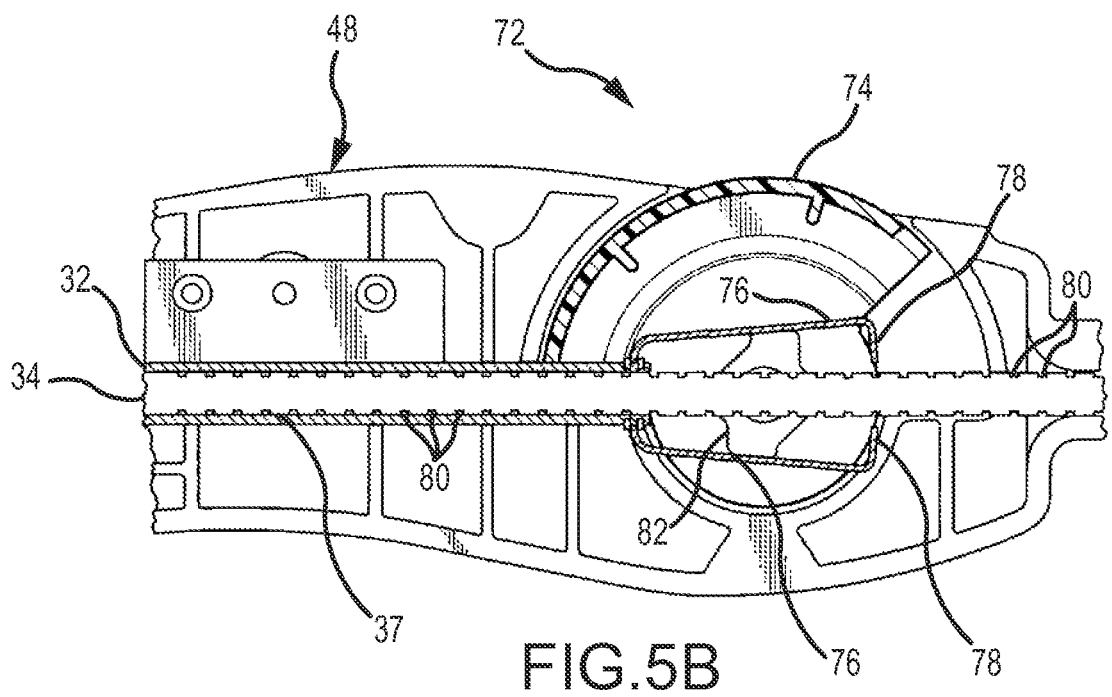
FIG. 5B is a longitudinal cross-sectional view similar to that shown in FIG. 5, showing an unlocked position of the locking mechanism.

A locking mechanism 72 of the front handle 48 selectively locks the advancement device 34 in a desired advanced or retracted position within the passageway 38, as shown in FIGS. 5 and 6. The locking mechanism 72 comprises a rotatable brake wheel 74 which is movable between a locked position (FIG. 5) and an unlocked position (FIG. 6). A pair of brake spring arms 76 are mounted in the front handle 48 on opposite sides of the advancement rod 37 of the advancement device 34. The brake spring arms 76 are preferably formed from a single piece of spring steel having a bridge portion between the spring arms 76 with a hole though the bridge portion to accept the advancement rod 37. Ends 78 of the brake spring arms 76 are biased to contact the advancement device 34 in the locked position. Evenly-spaced circumferential notches 80 are spaced apart along the circumference of a length of the advancement rod 37 which passes adjacent to the ends 78 of the brake spring arms 76. The notches 80 are each wide enough to receive the ends 78 of the brake spring arms 76. The advancement device 34 is locked in position when the ends 78 of the brake spring arms 76 are received in one of the circumferential notches 80.

A cam member 82 is formed on the brake wheel 74 to contact and bend the ends 78 of the brake spring arms 76 away from and out of the notches 80 of the advancement rod 37, when the brake wheel 74 is rotated into the unlocked position (FIG. 6). The shape of the cam member 82 maintains the brake wheel 74 in the unlocked position once rotated into the unlocked position, without requiring continuous external force to hold the brake wheel 74 in the unlocked position. The axial movement of the advancement device 34 is not impeded by the brake spring arms 76 when the brake wheel 74 is in the unlocked position.

When the brake wheel 74 is rotated into the locked position (FIG. 5) from the unlocked positioned (FIG. 6), the ends 78 of the brake spring arms 76 move into at least one circumferential notch 80. If the ends 78 contact the advancement rod 37 of the advancement device 34 at a location between two circumferential notches 80, the ends 78 will slide into an adjacent one of the notches 80 with further slight distal or proximal movement of the rear handle 50, thereafter locking the advancement device 34 in place. The ability to lock the advancement device 34 in a desired position, and therefore establish a desired position of the cutting tip 40, is a convenience to the surgeon for holding the position of the cutting tip 40 at different stages of the procedure, without requiring continual manual force to hold the desired position. Although not shown, a cap may be hinged to the front handle 48 to selectively pivot and cover and uncover the brake wheel 74. When the cap is pivoted into the position covering the brake wheel 74, manipulation of the handle 48 will not accidentally move the brake wheel 74 into an unlocked position.

The distal end 28 of the rigid hollow tube 32 is capped with a semispherical soft sheath 84 before use, as shown in FIG. 7. The semispherical soft sheath 84 provides a rounded or curved forwardmost end on the distal end 28 of the sound 22, which facilitates guiding the distal end 28 of the sound 22 through the urinary tract 24. The curved forwardmost end created by the soft sheath 84 helps to prevent trauma to the urinary tract 24 (FIG. 17) which might otherwise occur, if the forwardmost end of the distal end 28 of the sound 22 was open and inserted into the urinary tract 24, for example. The sheath 84 is also useful to prevent unnecessary trauma to the bladder 26 when the surgeon probes the bladder to locate the desired position for creating the surgical pathway. The sheath 84 is formed from material such as silicone, which is readily pierced when the cutting tip 40 is extended.

The pathway 38 at the distal end 28 of the rigid hollow tube 32 of the sound 22 includes an increased diameter portion 86 to accommodate the cutting blade 41 of the cutting tip 40. The cutting tip 40 includes a cutting tip connector 88 which connects with an advancement device connector 90 formed on the distal end 42 of the advancement coil 35. The interaction of the cutting tip connector 88 and the advancement device connector 90 releasably connects the cutting tip 40 to the advancement coil 35, as shown in FIGS. 7 and 8.

Figure 8:
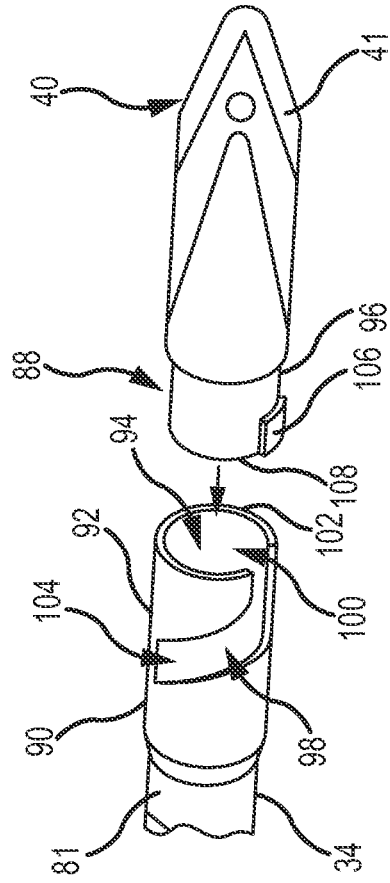
FIG. 8 is an exploded partial perspective view of the advancement coil and the cutting tip shown in FIG. 7, illustrating a bayonet connection of the advancement coil and the cutting tip.

The advancement device connector 90 includes a tubular wall 92 which defines a receptacle 94, as shown in FIGS. 7 and 8. The cutting tip connector 88 includes a cylindrical main body 96 sized to closely fit within the receptacle 94. A spiral shaped entry slot 98 is formed into the tubular wall 92. The entry slot 98 extends from an opening 100 at a distal end 102 of the tubular wall 92 to an end 104 located proximally from the distal end 102. A bayonet finger 106 extends radially outward from a small portion of a base 108 of the cylindrical main body 96. To connect the cutting tip connector 88 to the advancement device connector 90, the base 108 of the cylindrical main body 96 is coaxially aligned with the receptacle 94 and the bayonet finger 106 is axially aligned with the slot opening 100. The cylindrical main body 96 is then pushed into the receptacle 94 as the bayonet finger 106 enters the entry slot 98. The main body 96 is rotated relative to the receptacle 94 until the bayonet finger 106 abuts against the slot end 104. The cutting tip connector 88 is disconnected from the advancement device connector 90 by reversing this action.

The cutting tip connector 88 and the advancement device connector 90 described above are bayonet-style connectors. Other types of connectors may be used to connect the cutting tip 40 to the advancement coil 35. One other type of connector is created by interdigitated cutting tip and advancement device connectors 110 and 112, respectively, shown in FIGS. 9 and 10. Both connectors 110 and 112 have cylindrical bodies 114 and 116 with mating ends 118 and 120, respectively. The mating ends 118 and 120 interconnect with one another to connect the cutting tip 42 and the distal end 42 of the advancement coil 34.

The mating ends 118 and 120 each have deep radially-extending recesses 122 adjacent to a shallow radially-extending recesses 124 formed into sides of the cylindrical bodies 114 and 116. The shape of each deep recess 122 is complementary to the shape of each shallow recess 124 formed on the other mating end 118 and 120. The deep recesses 122 of each mating end 118 and 120 mate with the complementary shallow recesses 124 of the other mating end 118 and 120. The mating ends 118 and 120 laterally connect to axially align the cylindrical bodies 114 and 116 as a continuous cylinder when the complementary recesses 124 and 122 fit together, as shown in FIG. 10.

Figure 10:
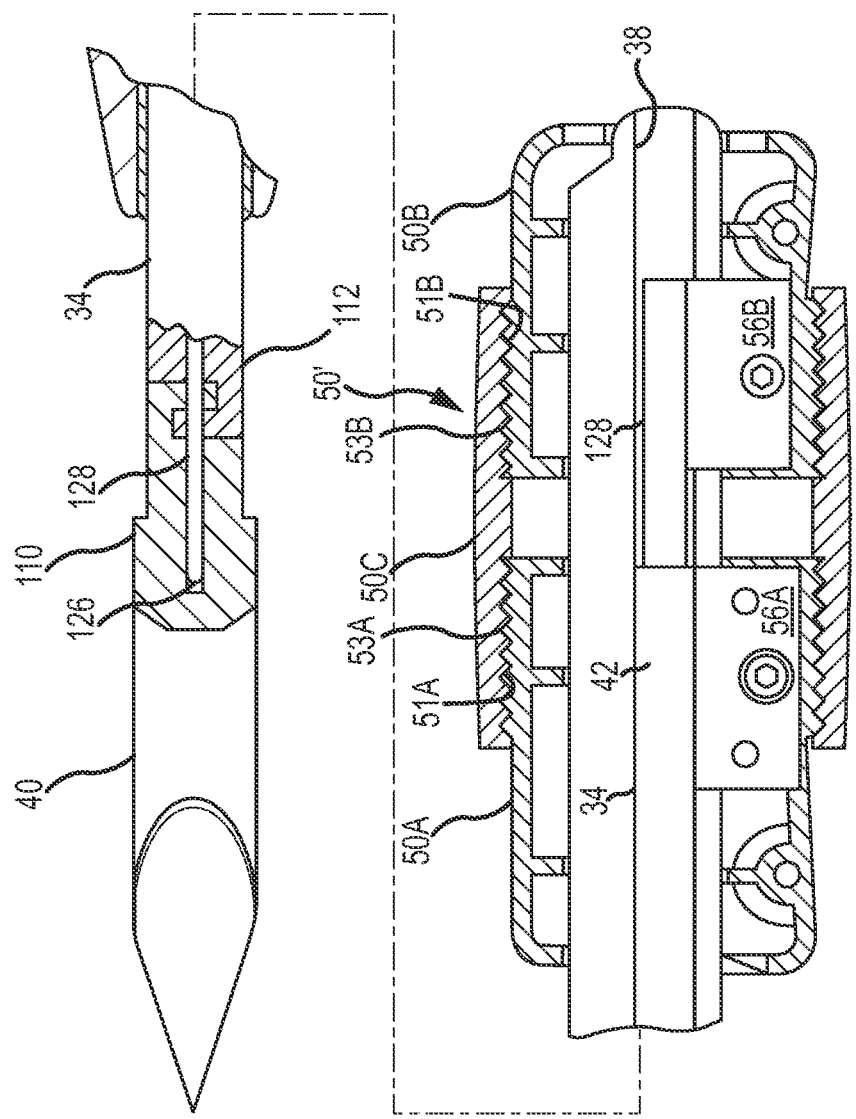
FIG. 10 is a longitudinal and broken out cross-sectional view of the interdigitated connection between the advancement coil and the cutting tip shown in FIG. 9, and its interaction with an alternative embodiment of the rear handle of the apparatus shown in FIG. 1.

To keep the mating ends 118 and 120 together in the connected position shown in FIG. 10, both cylindrical bodies 114 and 116 have center openings 126 which align to form a single continuous center opening when the cylindrical bodies 114 and 116 are connected. A lock structure or wire 128 is axially movable within the advancement device 34 and is used to hold the interdigitated connectors 110 and 112 in the connected-together and locked-together relationship. The interdigitated connectors 110 and 112 are locked together by advancing the lock wire 128 into the center openings 126 of the connected together cylindrical bodies 114 and 116. The mating ends 118 and 120 are prevented from moving laterally with respect to each other, and are thus prevented from disconnecting from each other. The mating ends 118 and 120 are disconnected from each other by retracting the lock wire 128 from the center openings 126 and then laterally separating the mating ends 118 and 120 from one another. The lock wire 128 extends from the distal end 42 of the advancement coil 35 to the proximal end of the advancement rod 37 through the passageway 38 of the rigid hollow tube 32 to the rear handle 50 of the proximal portion of the apparatus 20 (FIG. 1).

Another embodiment of the rear handle 50', shown in FIG. 10, allows the surgeon to selectively advance or retract the lock wire 128, and thereby selectively connect or disconnect the interdigitated cutting tip and advancement device connectors 110 and 112. The rear handle 50' is formed by a front portion 50A and rear portion 50B. A connector plate 56A connects the advancement rod 37 of the advancement device 34 to the front portion 50A, and a connector plate 56B connects the lock wire 128 to the rear portion 50B. Threads 51A and 51B on the exterior of both the front and rear portions 50A and 50B respectively engage threads 53A and 53B on the interior portion of rotatable sleeve 50C. The threads 51A/53A are reversed with respect to the threads 51B/53B. Rotation of the sleeve 50C about the front and rear portions 50A and 50B in one direction causes the front and rear portions 50A and 50B to move closer together and rotation of the sleeve 50C about the front and rear portions 50A and 50B in the other direction causes the front and rear portions 50A and 50B to move apart.

When the front and rear portions 50A and 50B move closer together with rotation of the sleeve 50C, the lock wire 128 is advanced within the advancement device 34. When the front and rear portions 50A and 50B move farther apart with rotation of the cylindrical connector 50C in the opposite direction, the lock wire 128 is retracted within the advancement device 34. When the sleeve 50C remains stationary with respect to the front and rear halves 50A and 50B, the front and rear halves 50A and 50B move in unison to advance or retract the advancement device 34 within the passageway 38.

Using the bayonet-style connectors 88 and 90 (FIGS. 7 and 8) rather than the interdigitated connectors 110 and 112 (FIGS. 9 and 10) eliminates the need for the extra mechanical lock wire 128 and eliminates the need for multiple parts in the rear handle 50, to connect or disconnect the cutting tip 40 from the advancement coil 35. On the other hand, using the interdigitated connectors 110 and 112 rather than the bayonet-style connectors 88 and 90 positively locks the interdigitated connectors 110 and 112 together, thereby providing assurance that the connectors 110 and 112 will not disengage without the affirmative mechanical action of rotating the sleeve 50C to retract the lock wire 128.

Figure 19:
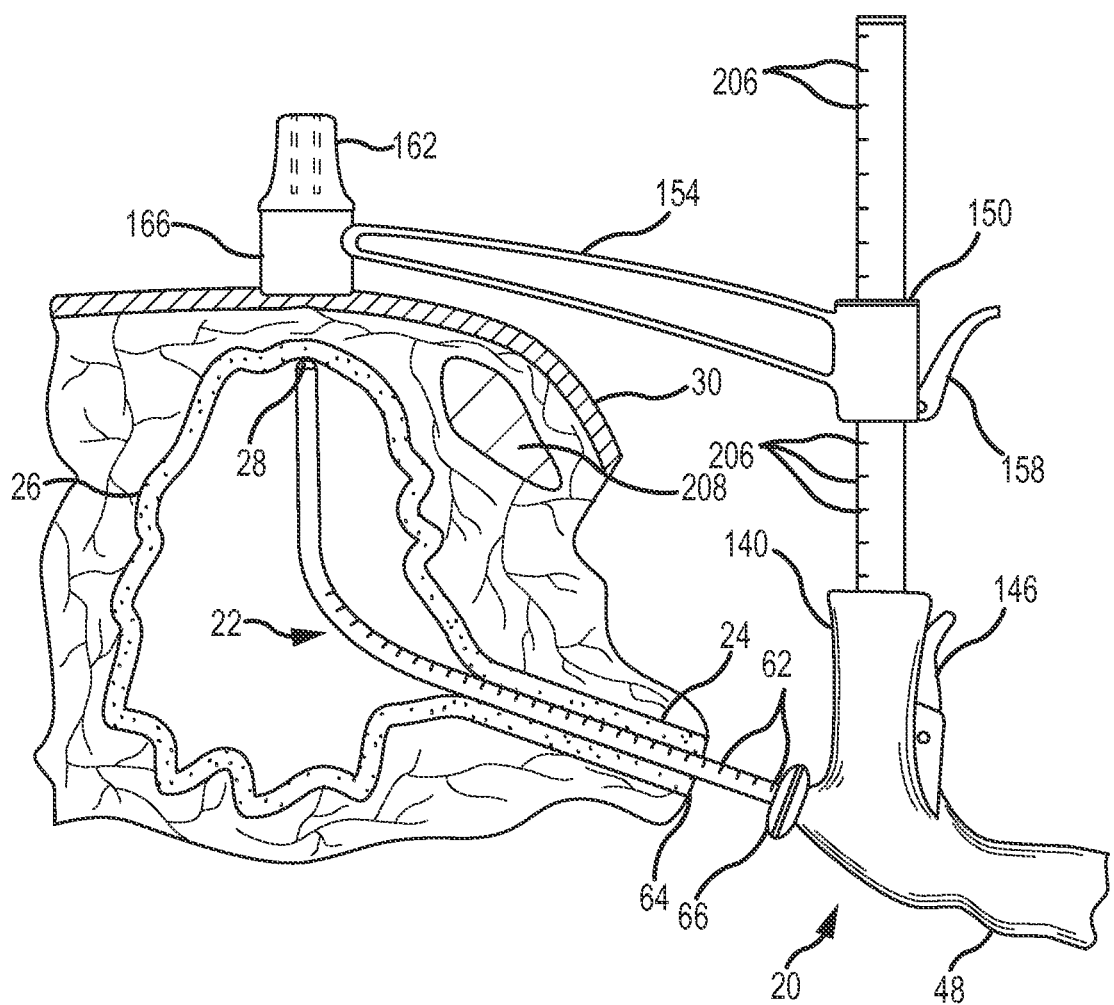
Figure 20:
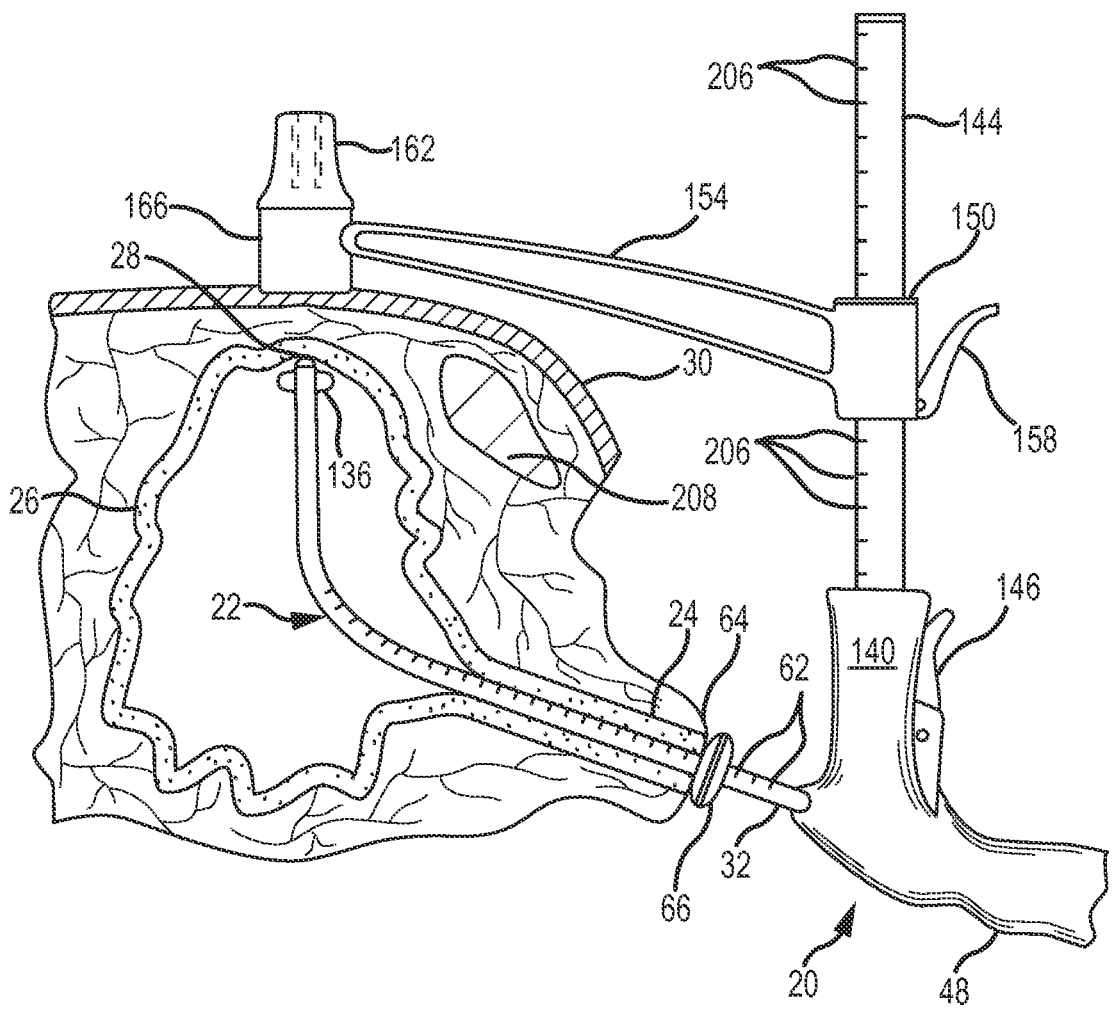
Figure 21:
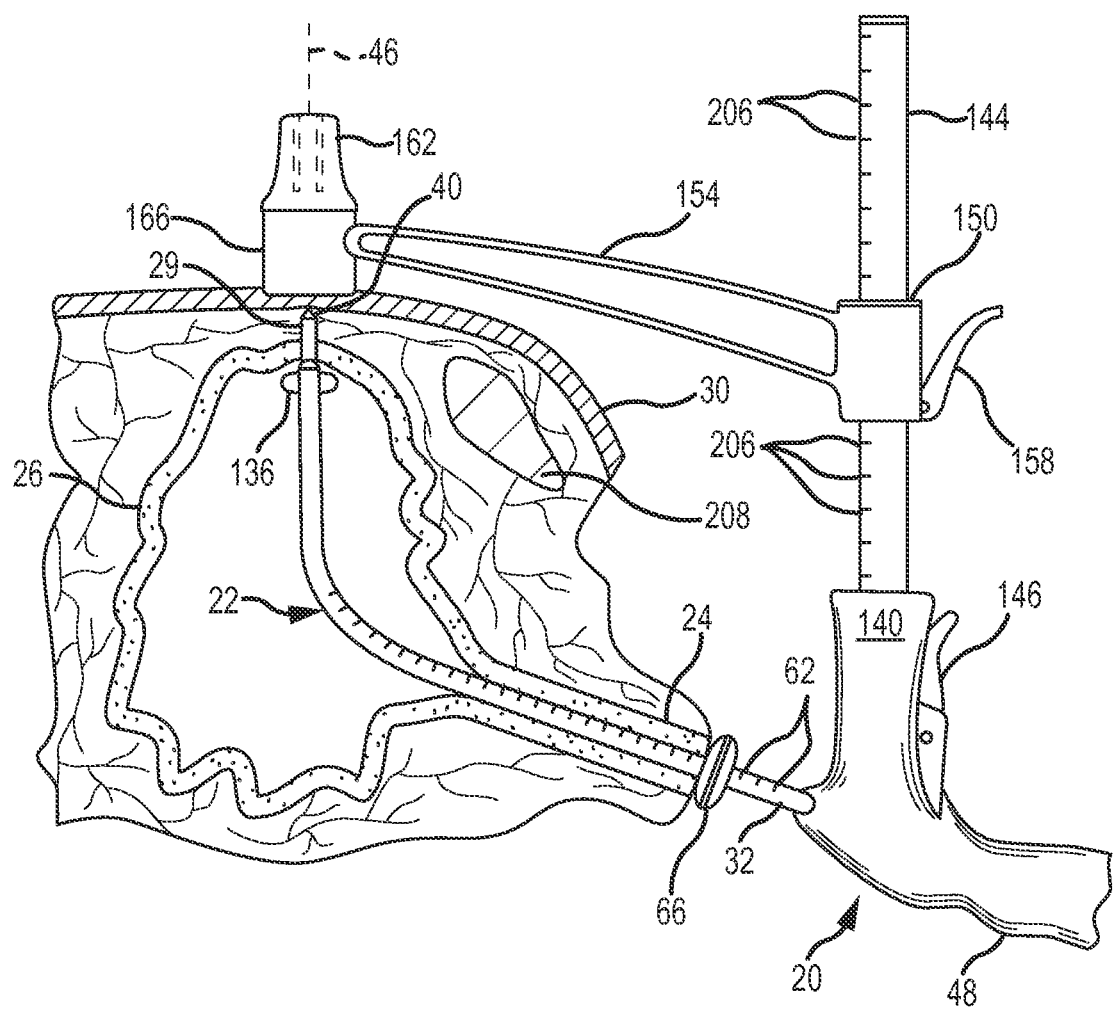
Figure 22:
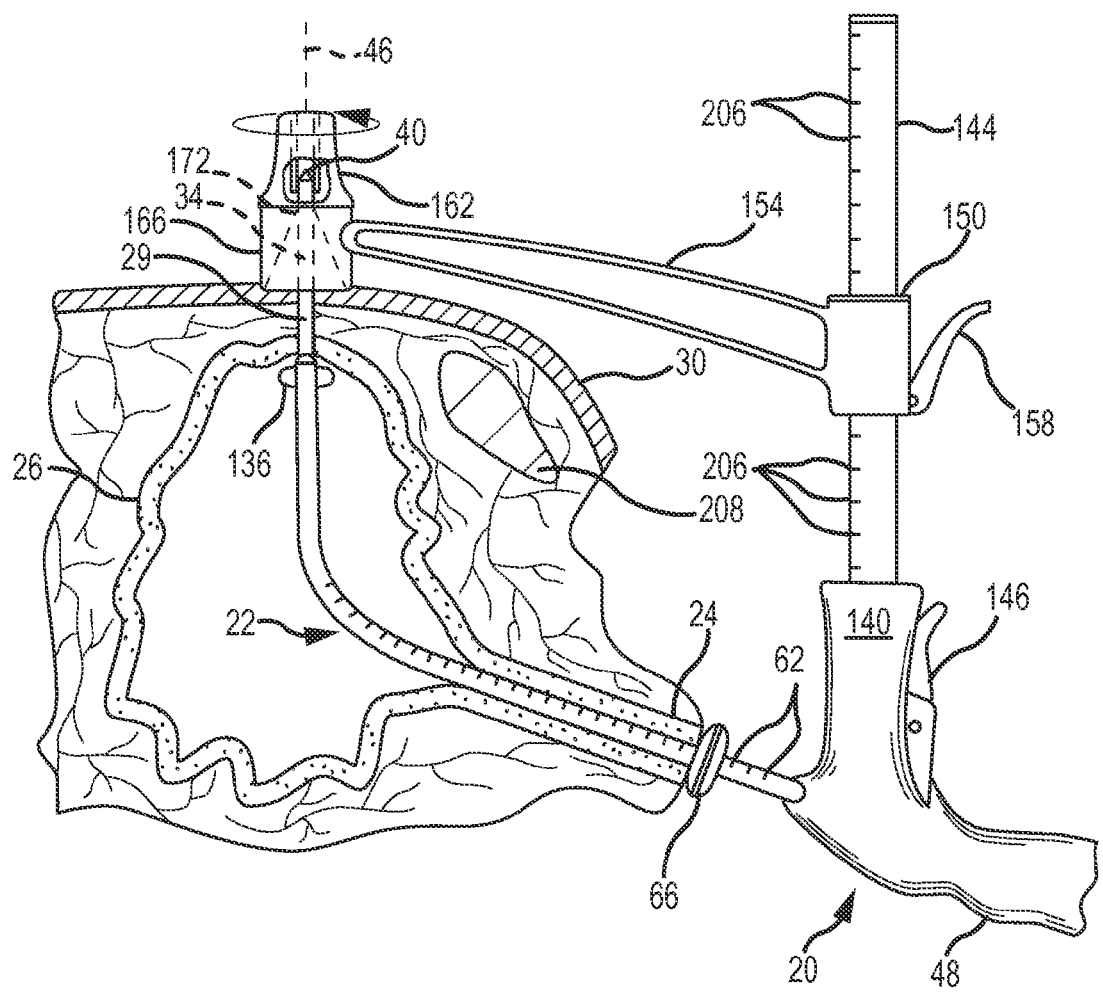

The primary purpose of the advancement device 34 is to advance the cutting tip 40 along a desired linear path 46 through the bladder 26 and the intervening tissue to the external abdomen 30 (FIGS. 17-22). The advancement coil 35 of the advancement device 34 must therefore have sufficient lateral stiffness and strength to avoid substantially deviating the path of cutting movement of the cutting tip 40 through the bladder 26 and the intervening tissue to the external abdomen 30, compared to the desired path 46, as the advancement coil 35 is extended from the straight portion 47 of the hollow rigid tube 32 (FIGS. 21 and 22). However, the advancement coil 35 must also be flexible enough to bend during movement through the curved portion 36 of the rigid hollow tube 32 (FIGS. 1 and 2) when the advancement coil 35 is advanced or retracted.

Figure 11:
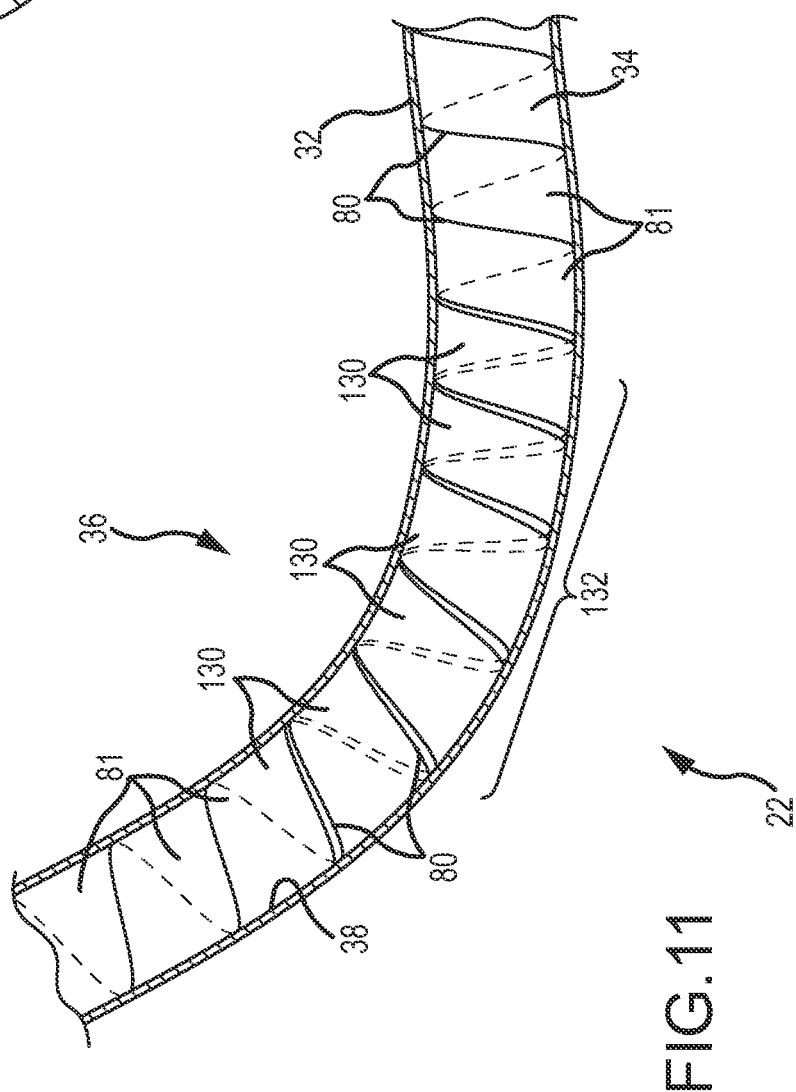
FIG. 11 is a partial longitudinal cross-sectional view of a curved portion of the sound and of the advancement coil contained in that curved portion of the apparatus shown in FIG. 1.

To achieve these functional characteristics, the advancement coil 35 is constructed from a single ribbon or band 81 of metal that is tightly wound in a helical coiled or spiraled manner to form a tube-like shape, as shown in FIG. 11. The band 81 forms a series of adjacent coils 130 which continuously abut one another when the advancement coil 35 extends linearly. The abutting adjacent coils 130 thus resist linear compression. The resistance to linear compression allows the advancement coil 35 to transmit enough mechanical force to the cutting tip 40 from the rear handle 50 to cut through the bladder 26 and the abdominal tissue to the exterior abdomen 30. Similarly, because of the width of the band 81 and its spiral-wound construction, the adjacent coils 130 also resist linear expansion. The resistance to linear expansion allows the retraction of the advancement coil 35 to retract the cutting tip 40 approximately the same distance as the rear handle 50 is moved. In this manner, the surgeon has excellent control over the degree of extension and retraction of the cutting tip 40.

The coiled configuration of the band 81 allows the adjacent coils 130 of the advancement coil 35 to separate slightly from one another along an outside arc 132 as the advancement coil 35 moves through the curved portion 36 of the rigid hollow tube 32, as shown in FIG. 11. The ability of the individual coils 130 to separate slightly at the outer turn radius of the curved portion 26 allows the advancement coil 35 to bend as necessary without compromising the previously described requirements for straight advancement with slight or no deviation from the desired path 46 (FIG. 18) when cutting the surgical pathway 29 (FIGS. 21 and 22).

Figure 12:
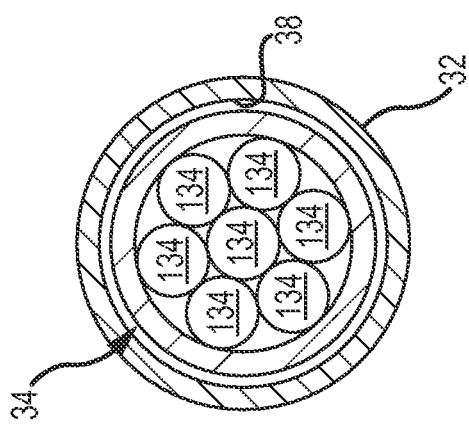
FIG. 12 is a transverse cross-sectional view of another embodiment of the advancement coil of the apparatus shown in FIGS. 1 and 11, containing a plurality of small diameter rods.

If it is desired to further stiffen the advancement coil 35 against lateral deflection without compromising its capability to move through the curved portion 36, the open center area within the advancement coil 35, may be filled with small diameter rods 134 of moderate flexibility, shown in FIG. 12. The small diameter rods 134 extend the entire length of the advancement coil 35. The rods 134 may extend generally parallel to one another, or the outside rods 134 may be slightly helically spiraled with respect to one another.

The small diameter rods 134 may be part of the advancement coil 35 when the bayonet-style connectors 88 and 90 (FIGS. 7 and 8) connect the cutting tip 40. However, the lock wire 128 used with the interdigitated connectors 110 and 112 could also be used at the center of an outer circumference of rods 134. Under such circumstances, the outer circumference of rods 134 is connected together and the lock wire 128 moves relative to the outer circumference of rods 134. A friction-reducing sheath or surface surrounding the lock wire 128 facilitates movement of the lock wire 128 relative to the outer circumference of rods 134.

Figure 13:
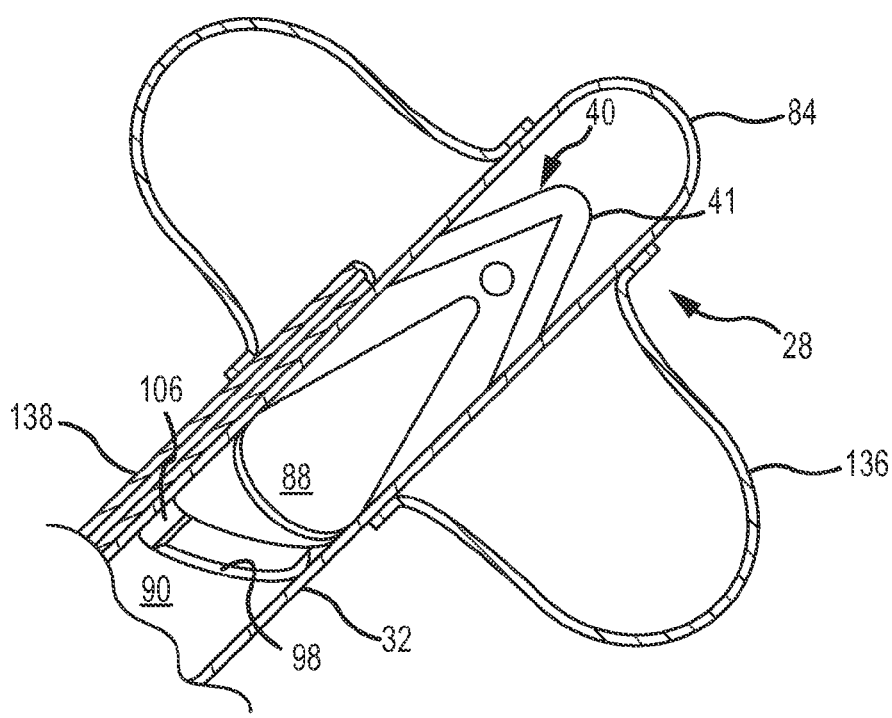
FIG. 13 is a partial longitudinal cross-sectional and perspective view of a distal end of the sound of the apparatus shown in FIGS. 1 and 7, illustrating an inflatable balloon.

When the surgical pathway 29 is created through the bladder 26 and the intervening tissue to the external abdomen 30, the distal end 28 of the sound 22 may inadvertently also extend into the surgical pathway, as can be understood from FIGS. 21 and 22. To eliminate the need for the surgeon to precisely hold the proximal end of the apparatus 20 while the surgical pathway 29 is created, and thereby avoid inadvertently moving the distal end 28 of the sound 22 into the surgical pathway 29, an inflatable balloon 136 is used at the distal end 28 of the sound 22 and the rigid hollow tube 32, as shown in FIG. 13. The inflatable balloon 136 is connected to an inflation tube 138 which extends along the rigid hollow tube 32 from the distal end 28 to near the front handle 48 (FIGS. 1 and 2). The inflation tube 138 terminates at its distal end in a conventional fitting (not shown) which allows inflation fluid to be delivered through the tube 138 and into the balloon 136 for inflating the balloon. After inflation, the connection fitting holds the inflation fluid to maintain the balloon 136 in its expanded position shown in FIG. 13. The conventional fitting also allows the inflation fluid to be removed to collapse the balloon 136.

The inflatable balloon 136 is collapsed against the exterior of the rigid hollow tube 32 when deflated so as not to impede the insertion of the sound 22 through the urinary tract 24. The balloon 136 is inflated after the distal end 28 of the sound 22 has been inserted into the bladder 26 and prior to advancing the cutting tip 40 from the rigid hollow tube 32 to create the surgical pathway (FIG. 20). The inflated balloon 136 presses against the bladder 26 when creating the surgical pathway from the bladder 26 through the intervening tissue to the external abdomen 30 (FIGS. 21-22). Pressing the inflated balloon 136 against the bladder 26 surrounding the location of the surgical pathway prevents the distal end 28 of the sound 22 from extending into the surgical pathway and possibly even completely through the surgical pathway.

Extending the distal end 28 of the sound 22 into the surgical pathway creates additional trauma and may tear or otherwise distort the surgical pathway and make use of other equipment during the procedure more difficult. The restraint from the inflated balloon 136 is particularly useful when the rear handle 48 is forced forward to advance the cutting tip and create the surgical pathway. The force caused by moving the rear handle 48 forward may be transferred through the apparatus 20, but the inflated balloon 136 resists this effect. Of course, the balloon 136 is deflated before the sound 22 is removed from the bladder 26 and the urinary tract 24.

The apparatus 20 shown in FIGS. 1 and 2 includes a mast 144, a guide arm 156 and a capture cup 162 which are also used while the sound 22 is located in the urinary tract 24 and bladder 26. The terms "distal" and "proximal" are used in reference to the same relative positions previously described relative to the proximal front and rear handles 48 and 50, even though the mast 144, the guide arm 156 and the capture cup 162 are located on the exterior of the patient during use.

In the apparatus 20, shown in FIGS. 1 and 2, a closed mast receiver 140 extends upward (as shown) from the front handle 48 and defines a pocket 142 into which the mast 144 is inserted. A conventional cam latch lever 146 is attached to the mast receiver 140 and is movable between an unlocked and locked positions. The cam latch lever 146 includes a cam 148 that pushes the mast 144 against the mast receiver 140 when the cam latch lever 146 is in the locked position (shown in FIGS. 1 and 2). Locking the mast 144 into position within the receiver 140 holds the mast 144 within the closed mast receiver 140 and also limits or eliminates any movement or play that might otherwise occur between the mast 144 and the receiver 140.

An open mast receiver 150 is formed on a proximal end 152 of the guide arm 154. The open mast receiver 150 defines an opening 156 which is sized to receive the mast 144 at a location vertically spaced from the location where the mast 144 is received in the closed mast receiver 140. A cam latch lever 158, similar to the cam latch lever 146, is attached to the open mast receiver 150. The cam latch lever 158 is movable between an unlocked position (FIG. 18) and a locked position (FIGS. 1, 2 and 19-22). The cam latch lever 158 locks the mast 144 in position within the open receiver 150 when the cam latch lever 158 is in the locked position. The cam latch lever 158 has a cam 160 (FIG. 2) that presses against the mast 144 when the cam latch lever 158 is in the locked position, thus preventing the mast 144 from moving within the opening 156. Locking the mast 144 into position within the open receiver 150 holds the guide arm 154 in a rigid position relative to the mast 144 and also eliminates any movement or play that might otherwise occur between the mast 144 and the guide arm 154.

The mast 144 and the guide arm 154 position the capture cup 162 coaxially with the expected travel path 46 of the cutting tip 40 (FIGS. 18 and 19). The capture cup 162 is removably connected at a distal end 164 of the guide arm 154, as described in more detail below, and is used to safely accept, remove and retain the cutting tip 40 after it has been used to create the surgical pathway. After the capture cup 162 has accepted the cutting tip 40, the capture cup 162 is manipulated to disconnect the cutting tip 40 from the advancement device 34 and release the capture cup 162 from the guide arm 154. The cutting tip 40 is safely retained within the capture cup 162 to prevent inadvertent contact with the cutting tip 40. Retaining the cutting tip 40 within the capture cup 162 allows both components to be safely handled by the surgical personnel without risk of encountering the cutting tip 40. Both the capture cup 162 and the retained cutting tip 40 are disposed of as a single device as medical waste.

Figure 14:
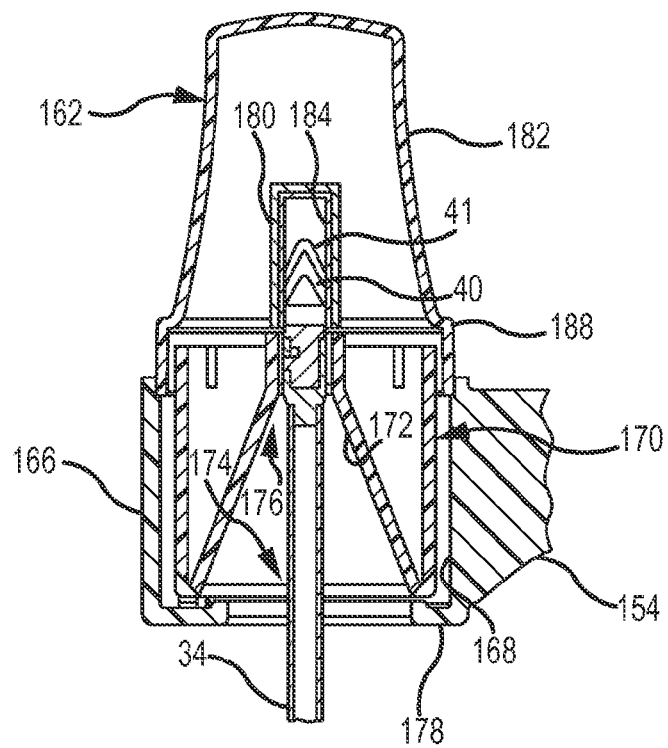
FIG. 14 is a partial longitudinal cross-sectional view of a capture cup and funnel housing connected to a distal end of a guide arm of the apparatus shown in FIG. 1, illustrating the cutting tip advanced into the capture cup.
Figure 15:
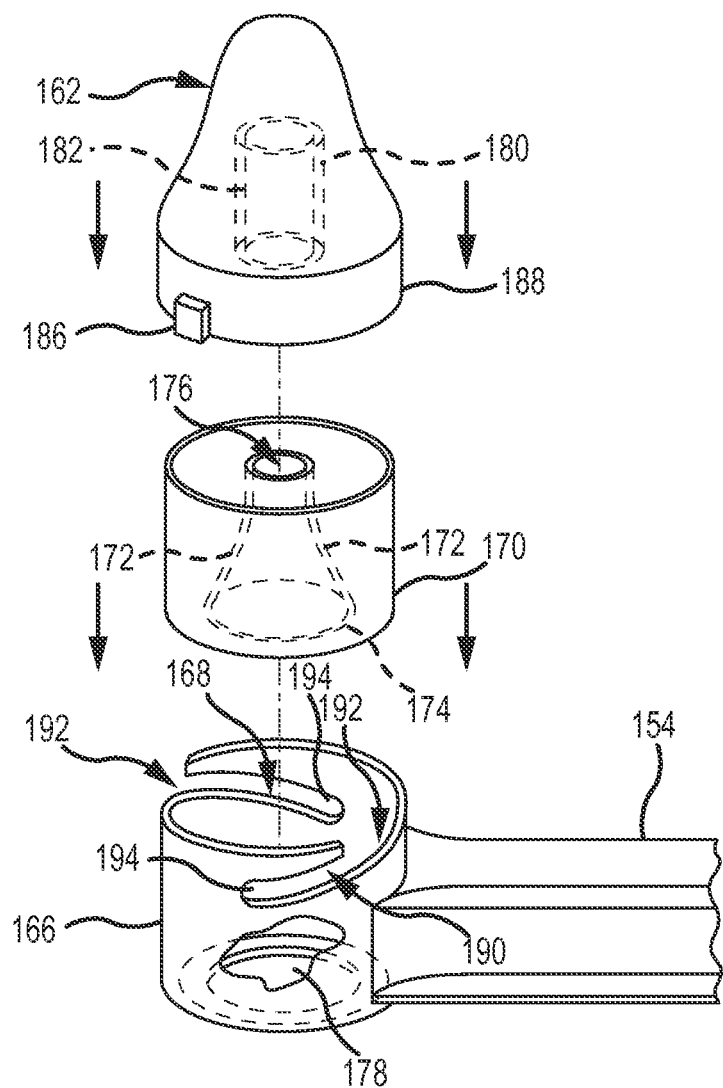
FIG. 15 is an exploded perspective view of the capture cup, funnel housing and a portion of the guide arm shown in FIG. 14.

An annular housing 166 is formed on the distal end 164 of the guide arm 154, as shown in FIGS. 14 and 15. The annular housing 166 defines a cylindrical cavity 168 which receives a funnel housing 170. The funnel housing 170 defines an inverted funnel shape 172. The inverted funnel shape 172 has a relatively large diameter opening 174 at the bottom (as shown) of the funnel housing 170 and transversely and upwardly constricts to a relatively small diameter opening 176 at the top (as shown) of the funnel housing 170. An annular support lip 178 extends radially inward from the bottom (as shown) of the annular housing 166. The support lip 178 holds the funnel housing 170 in position at the bottom of the cylindrical cavity 168 defined within the annular housing 166.

The capture cup 162 releasably attaches to the top (as shown) of the annular housing 166 and sits atop the funnel housing 170 when attached to the annular housing 166. The inverted funnel shape 172 is preferably made from or lined with metal or hard ceramic material to prevent the cutting tip from penetrating the funnel shape 172. The funnel shape 172 directs the cutting tip 40 into a cylindrical cavity 180 of the capture cup 162 (FIG. 14), after the cutting tip has created the surgical pathway. The capture cup 162 includes a capture housing body 182 from which the cylindrical cavity 180 opens downward (as shown) above the small diameter opening 176 of the inverted funnel shape 172. The capture housing body 182 is preferably constructed from translucent or transparent plastic material so that the surgeon can observe the cutting tip 40 entering the cavity 180. The cylindrical cavity 180 has a diameter approximately equal to the diameter of the small diameter opening 176 of the inverted funnel shape 172. A relatively pliable elastomeric or polymeric sleeve 184, which is also preferably constructed of translucent or transparent plastic, is attached to the inside of the cylindrical cavity 180.

Bayonet fingers 186 (one of which shown in FIG. 15) extend radially outward from opposing sides of an annular base 188 of the capture housing body 182 and fit within spiral slots 190 formed in the annular housing 166. The spiral slots 190 extend from open ends 192 which each extend in a downward about 90 degrees in a clockwise spiral manner (as viewed from the top of the annular housing 166) around a circumference of the annular housing 166. The spiral slots 190 terminate at ends 194 which are slightly closer to the bottom (as shown) of the annular housing 166 than are the open ends 192 of the spiral slots 190.

The capture cup 162 is connected to the annular housing 166 by first inserting the funnel housing 170 into the cylindrical cavity 168 with the large diameter opening 174 of the inverted funnel shape 172 facing downward, as shown in FIG. 15. The bayonet fingers 186 of the capture cup 162 are then aligned with and inserted into the open ends 192 of the spiral slots 190. The capture cup 162 is then rotated clockwise (as viewed from above the capture cup 162) until the bayonet fingers 186 reach the ends 194 of the spiral slots 190. With the capture cup 162 connected to the annular housing 166, the cylindrical cavity 180 of the capture cup 162 is adjacent to and coaxially aligned with the small diameter opening 176 of the inverted funnel shape 172.

The capture cup 162 is aligned with the intended path 46 of the cutting tip 40 when it is advanced from the distal end 28 of the sound 22. Because the advancement coil 35 is somewhat flexible in the lateral sense, the cutting tip 40 may deviate slightly from the path 46 as the cutting tip 40 is advanced. Under those conditions, the cutting tip 40 will nevertheless encounter the large diameter opening 174 of the inverted funnel shape 172 when the surgical pathway is completed. The inverted funnel shape 172 directs the cutting tip into the small diameter opening 176 and into the cylindrical cavity 180, despite the possibility of a slight lateral deviation of the cutting tip 140 from the desired path 46 (FIGS. 21 and 22) as the surgical pathway is created.

The elastomeric or polymeric sleeve 184 receives or "captures" the cutting tip 40 after the cutting tip 40 enters the cavity 180. The blade 41 of the cutting tip 40 cuts into the sleeve 184, as the cutting tip 40 enters the cavity 180. The blade 41 of the cutting tip 40 is wider than an inside diameter of the sleeve 184, causing the blade 41 to cut into the sleeve 184. The elastomeric or polymeric characteristics of the sleeve 184 create friction against the blade 41 to hold the cutting tip 40 in place within the cavity 180. In this manner, the cutting tip 40 is firmly lodged within cavity 180 of the capture cup 162.

To disconnect the cutting tip 40 from the advancement device 34 after cutting the surgical pathway and the cutting tip 40 has been received and held within the cavity 180 of the capture cup 162, as shown in FIG. 14, the bayonet-style connections of both the capture cup 162 to the annular housing 66 and the cutting tip 40 to the advancement coil 34 are simultaneously released by rotating the capture cup 162 in a counter-clockwise direction (as viewed from the top of the capture cup 162). The cutting tip 40 rotates with the capture cup 162 due to the retention of the cutting tip 40 in the cavity 180. The cutting tip connector 88 (FIG. 8) rotates in conjunction with the cutting tip 40 and disconnects from the advancement device connector 90 (FIG. 8). The advancement device 34 is prevented from rotating by virtue of the non-rotatable connection between the advancement device 34 and the rear handle 50 and between the rear handle 50 and the tubular body 52 (FIGS. 3 and 4). After the capture cup 162 has been disconnected from the annular housing 166 of the guide arm 154, the capture cup 162 along with the cutting tip 40 are discarded.

Since the spiral slot 98 of the advancement device connector 90 (FIGS. 7 and 8) and the spiral slots 190 of the annular housing 166 are similarly shaped, over-rotating the capture cup 162 will not damage any of the components, which might be the case if L-shaped slots were employed rather than spiral slots. Additionally, the longitudinal distances between the beginning and end of the slots 98 is greater than the longitudinal distances between the beginning and end of the slots 190 resulting in as slight longitudinal force on the cutting tip when the cutting tip connector 88 is disconnected from the advancement device connector 90. This slight longitudinal force causes the capture cup 162 jump slightly upward upon disconnection and create a tactile indication that the cutting tip connector 88 has been disconnected.

Figure 16A:
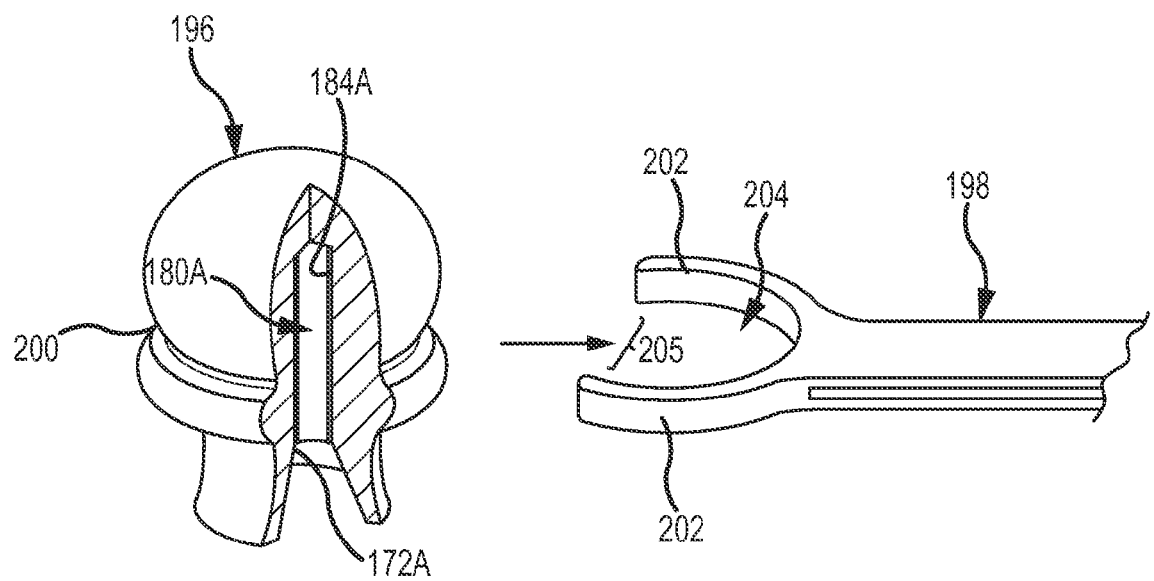
FIG. 16A is a perspective exploded view of another embodiment of the capture cup and guide arm compared to that shown in FIGS. 14 and 15, illustrating a portion of the capture cup broken out and a distal portion of the guide arm.

An alternative embodiment of a capture cup 196 and a guide arm 198 are shown in FIG. 16A. The capture cup 196 includes a funnel housing 170A, a cylindrical cavity 180A lined with an elastomeric or polymeric sleeve 184A and an inverted funnel shape 172A aligned with the cylindrical cavity 180A, all of which are integral with the capture cup 196 and similar in shape and function to comparable elements in the capture cup 162 (FIGS. 14 and 15). An annular recess 200 is defined on an exterior of the capture cup 196. A pair of forks 202 extend distally from the distal end of the guide arm 198 and define a semicircular-shaped opening 204, as compared to the annular housing 166 of the capture cup 162 (FIGS. 14 and 15). A gap 205 separates the distal ends of the forks 202.

The capture cup 196 connects to the guide arm 198 by insertion of the capture cup 196 through the gap 205 into the semicircular-shaped opening 204, with the forks 202 positioned tangentially within the annular recess 200. The forks 202 are moderately and resiliently flexible in a lateral sense and are normally separated by a diameter which is slightly less than the inner diameter of the annular recess 200. The distal ends of the forks 202 are separated at the gap 205 when the capture cup 196 is inserted between them. The forks 202 resiliently return almost to their normal position while fitting within the annular recess 200 to firmly hold the capture cup 196 with respect to the guide arm 198.

Once the cutting tip 40 is captured within the cavity 180A, as a result of the blade 41 of the cutting tip 40 cutting into the elastomeric or polymeric sleeve 184A, the capture cup 196 is rotated while the forks 202 to remain in the annular recess 200. The rotation of the capture cup 196 disconnects the bayonet style connection of the cutting tip connector 88 relative to the advancement device connector 90 (FIG. 8), leaving the cutting tip within the capture cup 196. The capture cup 196 is disconnected from the distal end of the guide arm 198 by separating the forks 202 and withdrawing the capture cup 196 from between the forks 202. Thereafter the capture cup 196 and the retained cutting tip 40 can be handled and disposed of without risk of injuring medical personnel.

One of the advantages of the fork-shaped connection arrangement between the capture cup 196 and the distal end of the guide arm 198, is that the space between the forks 202 allows additional medical equipment to be attached to the connector of the advancement device 34 without first disconnecting the mast 144 and/or guide arm 156, as is required in the embodiment shown in FIGS. 14 and 15. Connecting equipment to the advancement coil 34 after removing the cutting tip 40 without first removing the mast 144 and the guide arm 198 presents less risk of inadvertently losing the advancement device 34 within the surgical pathway 29 before the additional equipment is connected.

Figure 16B:
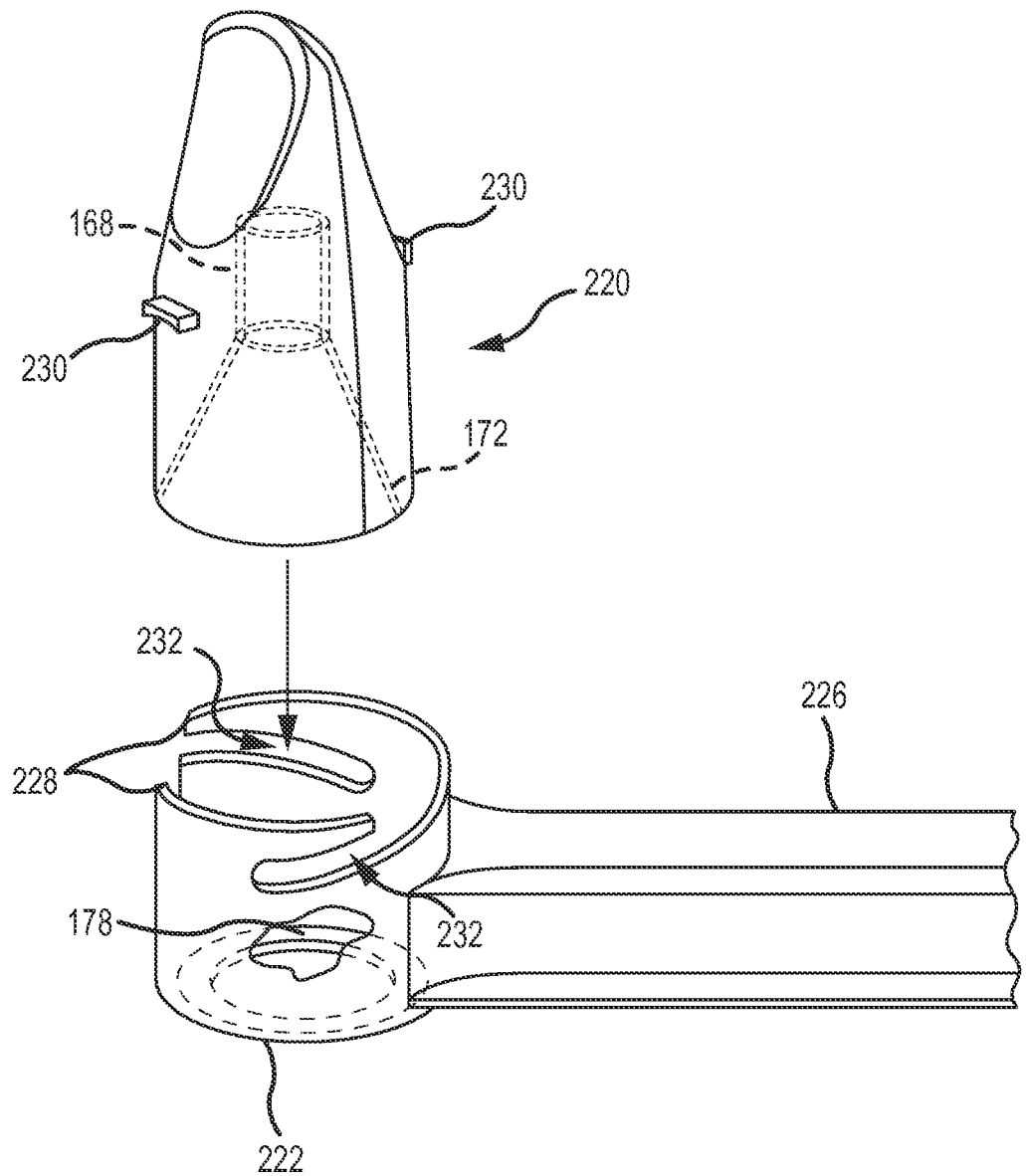
FIG. 16B is a perspective exploded view of another embodiment of the capture cup and guide arm compared to that shown in FIGS. 14 and 15 and in FIG. 16A, illustrating a portion of the capture cup broken out and a distal portion of the guide arm.

Another embodiment 220 of a capture cup which allows equipment to be connected to the advancement device 34 before disconnecting the guide arm and mast is shown in FIG. 16B. The capture cup 220 is similar to the integral capture cup 196 (FIG. 16A), in that it integrally includes a funnel housing, a cylindrical cavity lined with an elastomeric or polymeric sleeve, and an inverted funnel shape aligned with the cylindrical cavity (none of which are shown but all of which are generally similar to the comparable elements shown in the capture cup 200, FIG. 16A). The capture cup 220 is used with an annular housing 222 on the distal end of a guide arm 226. The annular housing 222 is similar to the annular housing 166 (FIG. 15), except that an opening 228 is formed in the circumference of the annular housing 222 on the opposite side from the guide arm 226. The opening 228 allows the guide arm 226 to be removed after the equipment has been attached to the advancement device 34.

The exterior surface of the capture cup 220 includes fingers 230 at diametrically opposite exterior positions. The fingers 230 are located to fit within spiral slots 232 formed in the annular housing 222. The spiral slots 232 are similar to the spiral slots 190 formed in the annular housing 166 (FIG. 15). Inserting the fingers 230 into the spiral slots 232 and twisting the capture cup 220 firmly attaches the capture cup 220 to the annular housing 222.

As an alternative to its use when retained to the guide arm, as described above, the embodiments of the capture cup previously described can be used independently to capture and retain the cutting tip, and to release the cutting tip from its connection to the advancement device. Such uses might not involve the use of the mast and the alignment arm of the cystostomy apparatus 20, but would involve the use of the sound 22.

After the cutting tip 40 is captured in the capture cup 230, the capture cup 222 is rotated to withdraw the fingers 230 from the spiral slots 232. This same rotational movement disconnects the cutting tip 40 from the distal end of the advancement coil 35. The capture cup 222 and the cutting tip 40 which is retained within it are thereafter removed from the guide arm 226. Additional equipment is attached to the advancement device connector 90. The opening 228 in the circumference of the annular housing 222 allows the guide arm to be removed after the additional equipment has been attached to the advancement coil 35.

Indicia 206 are formed along the length of the mast 144. The indicia 206 indicate distance between the bottom of the annular housing 166 and the tip of the distal end 28 of the sound 22. Because the tube 32 is rigid, and because the mast 144 is rigidly connected to the front handle 48 at the mast receiver 140, and because the guide arm 154 is rigidly connected to the mast 144 at the mast receiver 150, this rigid geometry allows the indicia 206 to reliably measure the distance between the tip of the distal end 28 of the sound and the bottom of the annular housing 166. The surgeon notes the distance between the bottom of the annular housing 166 and the distal end 28 of the sound 22 from the indicia 206. It is this distance that the cutting tip 40 will have to be advanced to create the surgical pathway.

The mast receiver 140 orients the mast 144 parallel to the straight portion 47 of the rigid tube 32 at the distal end 28 of the sound 22. Because of this parallel relationship, and because the projected path 46 of the cutting tip 40 is aligned with the straight portion 47 of the rigid tube 32, differences in the length of the surgical pathway are accurately indicated by the indicia 206. Furthermore, the capture cup 162 remains concentrically positioned relative to the path 46 despite repositioning the guide arm 154 along the mast 144.

An exemplary sequence of operations to perform a suprapubic cystotomy with the cystotomy apparatus 20 (FIGS. 1-16) is described below with reference to FIGS. 17-22.

The apparatus 20 is initially prepared for the cystotomy procedure by disconnecting the mast 144 from the front handle 48, and sliding the indicator slide 66 to a proximal position abutting the front handle 48. The mast 144, guide arm 154 and capture cup 162 are removed from the front handle 48 prior to inserting the sound 22 through the urinary tract 24 to prevent the mast, guide arm and capture cup from diminishing the tactile feel available to the surgeon when inserting the sound 22 through the urinary tract 24.

Figure 17:
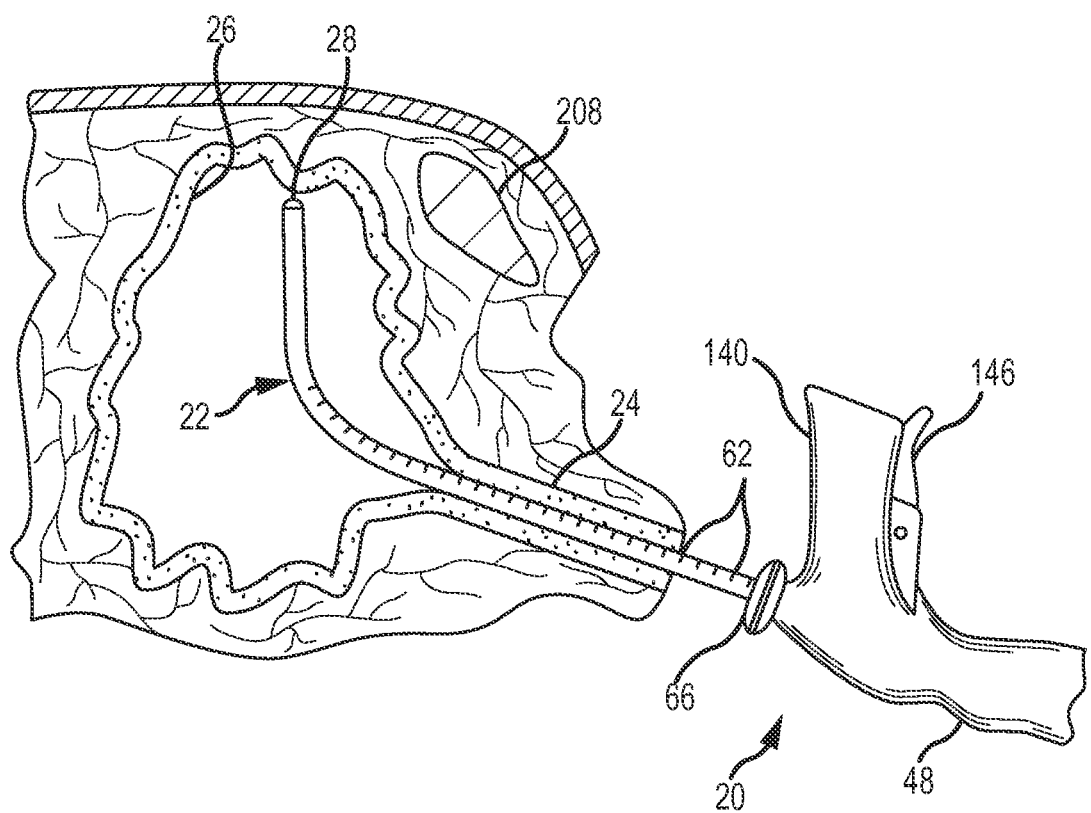
FIGS. 17-22 are partial cross-sectional and perspective views showing a series of actions involved in using the apparatus shown in FIGS. 1-16 in a cystotomy to cut a surgical pathway from the bladder to the exterior abdomen in a patient. More specifically.

The sound 22 is inserted through the urinary tract 24 and is positioned with the distal end 28 of the sound 22 facing toward the location on the external abdomen 30 from which the surgeon desires the surgical pathway to emerge, as shown in FIG. 17. The mast 144, the guide arm 54 and the capture cup 162 are then reconnected to the front handle 48. The mast 144 is inserted into the closed mast receiver 140 of the front handle 48 while the cam latch lever 146 is in the unlocked position. The mast 144 is then locked into position by moving the cam latch lever 146 into the locked position, as previously described.

The distal end 28 of the sound 22 is then pressed against the bladder 26 to establish a slight "tenting" position 210 of the external abdomen 30, as shown in FIG. 18. The tenting 210 is preferably at a location on the abdomen 30 about one or two finger widths above a pubic bone 208 of the patient.

The open mast receiver 150 is then unlocked by moving the latch lever 158 into the unlocked position, which allows the guide arm 154 to be lowered along the mast 144. Lowering the guide arm 154 in this manner places the capture cup 162 immediately above the tenting position 210, with the annular housing 166 resting on the external abdomen 30, as shown in FIG. 19. The cam latch lever 158 is then moved to the locked position locking the guide arm 154 into position relative to the mast 144. The mast 144 and the guide arm 154 position the capture cup 162 coaxial to the path 46 along which the cutting tip 40 is intended to be advanced.

With the guide arm 154 and the capture cup 162 in the position shown in FIG. 19, the surgeon then observes the separation distance between the tip of the distal end 28 of the sound 22 and the bottom of the annular housing 166, by use of the indicia 206. This distance represents the amount of advancement of the cutting tip 40 necessary to create the surgical pathway 29 (FIGS. 21 and 22).

The inflatable balloon 136 is then inflated to prevent the distal end 28 of the sound 22 from extending into the surgical pathway when the cutting tip 40 is advanced, as shown in FIG. 20. The indicator slide 66 is then moved along the hollow rigid tube 32 to abut against the external opening 64 of the urinary tract 24. The surgeon uses the indicia 62 along the hollow tube 32 to mark the desired position of the sound 22 within the urinary tract 24 and to also recognize unintended distal or proximal movement of the apparatus 20.

The cutting tip 40 is then advanced from the distal end 28 of the sound 22, as shown in FIG. 21, by moving the rear handle 50 (FIGS. 1 and 2) distally towards the front handle 48. The cutting tip 40 advances along the path 46 and cuts through the bladder 26 and the intervening tissue to the external abdomen 30, thereby creating the surgical pathway 29 which extends from inside the bladder 26 to outside of the patient at the external abdomen 30.

Advancement of the cutting tip 40 continues until the cutting tip 40 enters the cylindrical cavity 180 (FIGS. 14 and 15) of the capture cup 162 and becomes lodged within the sleeve 184 (FIGS. 14 and 15), as shown in FIG. 22. The surgeon knows how far the cutting tip 40 must advance to enter the capture cup 162 by reference to the indicia 206 on the mast 144. The extent of advancement of the cutting tip 40 is determined by reference to the indicia 68 (FIG. 1) on the tubular body 52 distal to the rear handle 50. The surgeon is assured that the cutting tip 40 has entered the capture cup 162 by visually observing the presence of the cutting tip 40 through the transparent or translucent capture cup 162. The cutting tip 40 should be observable within the capture cup 162 when the rear handle 50 moves slightly past the indicia 68 on the tubular body 52 corresponding to the distance indicated by the indicia 206 on the mast 144 between the tip of the distal end 28 of the sound 22 and the annular housing 166.

After the cutting tip 40 has been successfully captured within the capture cup 162, the capture cup 162 is rotated counter-clockwise (as viewed from above the capture cup 162) at least 90 degrees. The counter-clockwise rotation of the capture cup 162 simultaneously disconnects the cutting tip 40 from the advancement coil 35 and the capture cup 162 from the annular housing 166. In the embodiment which utilizes the interdigitated connections 110 and 112 (FIGS. 9 and 10), the lock wire 128 is retracted prior to separating the capture cup 162 (or 196) from the annular housing 166 at the distal end of the guide arm 154 (or from the semicircular opening 204 at the distal end of the guide arm 198). The capture cup with the retained cutting tip may thereafter be handled safely and disposed of as medical waste.

After the surgical pathway 29 has been created as shown in FIG. 22, it must be held open. Otherwise the pathway will collapse and will become impossible or very difficult to insert any equipment through the surgical pathway. To avoid collapse, a material object must always be present within the surgical pathway 29, thereby maintaining the surgical pathway 29.

The apparatus 20 is used to assist with the insertion of a cannula 400 (FIG. 33) within the surgical pathway 210, by which to access the bladder 26 with additional medical instruments (e.g., 414, FIG. 41) from outside of the patient to perform medical procedures inside the bladder 26. The apparatus 20 may also be used to assist with the insertion of a catheter (not shown) by which to drain urine from the bladder 26. The procedure and details of inserting the catheter through the surgical pathway into the bladder are described more completely in the previously-identified U.S. application Ser. No. 12/238,941. The remaining portion of the description contained herein will focus principally on inserting the cannula 400, although some of the following discussion is also applicable to inserting the catheter.

Prior to inserting the cannula 400 (FIG. 27), the surgical pathway 29 must be widened enough to receive the cannula 400. The cannula 400 has a transverse width that is significantly greater than the width of the cutting tip 40. Consequently, the cannula 400 will not fit within the surgical pathway 29 without first widening it.

Figure 23:
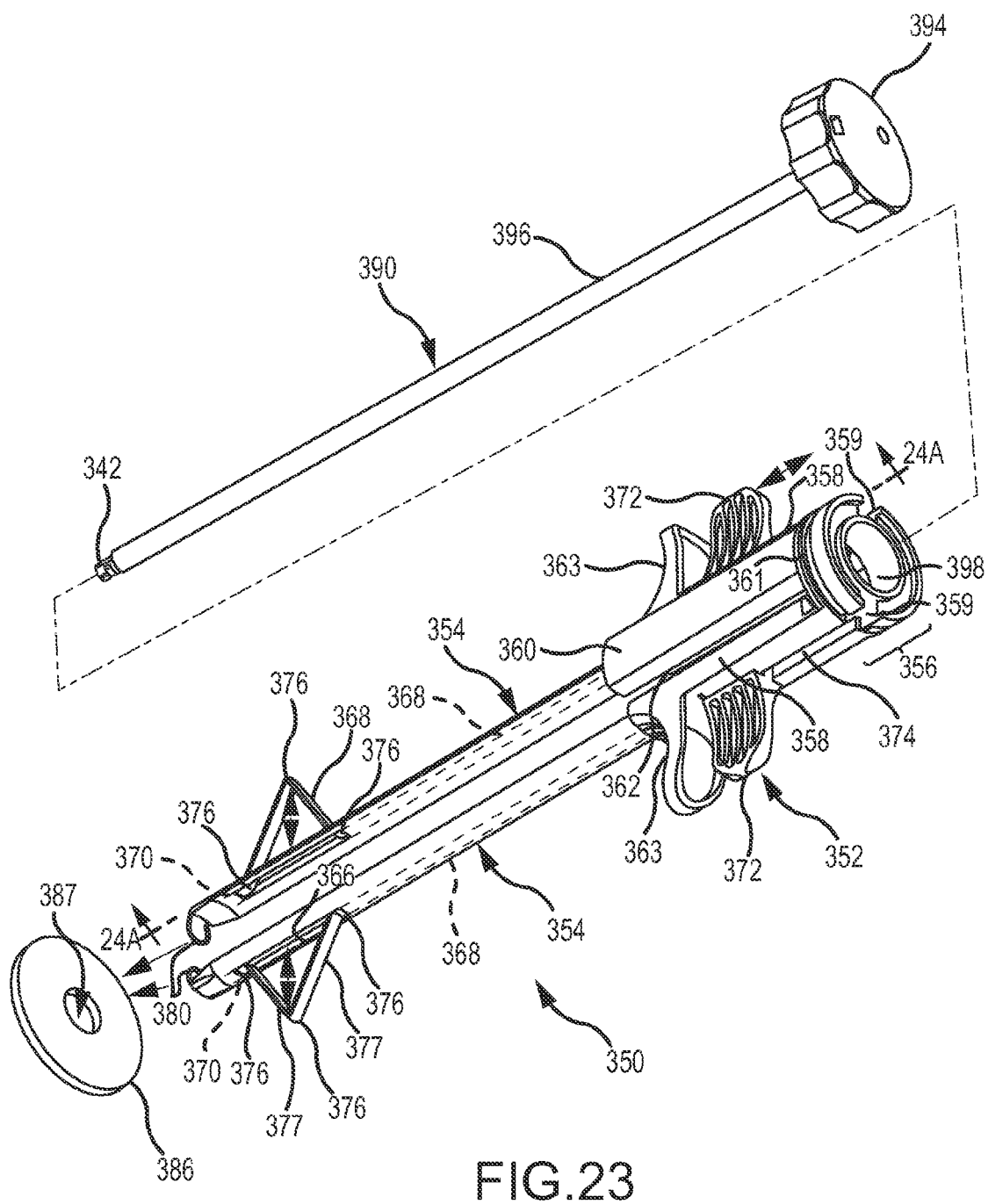
FIG. 23 is an exploded perspective view of a dilator and a stylet of the present invention used with the dilator, both of which are inserted into the surgical pathway between the bladder and abdomen created as shown in FIG. 22, by use of the apparatus shown in FIG. 1.
Figure 25B:
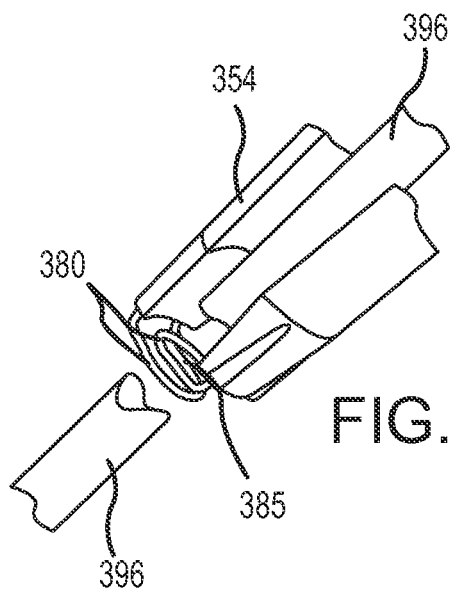
FIG. 25B is an enlarged perspective view of a portion of the dilator shown in FIG. 25A.
Figure 25A:
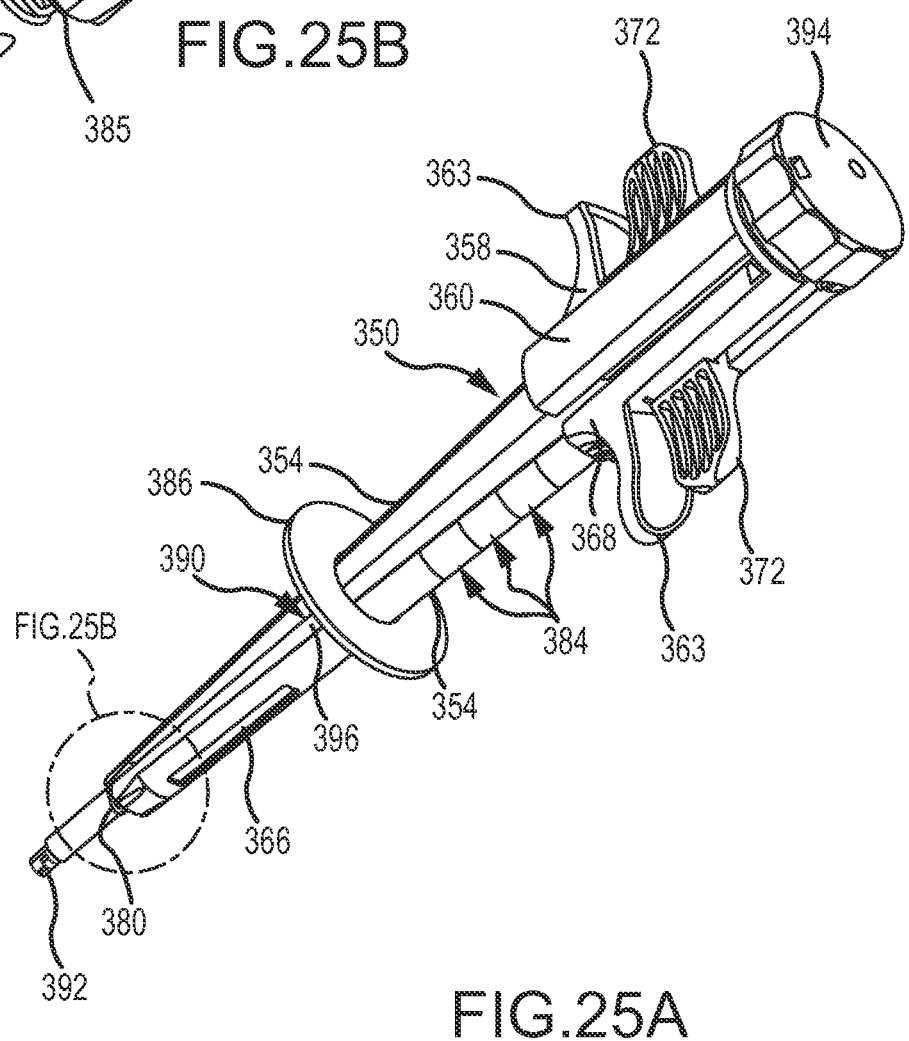
FIG. 25A is a perspective view of the dilator and the stylet shown in FIG. 23, illustrated in a connected together relationship, with an enlarged portion of a distal end of the connected dilator and stylet.

A dilator 350, shown in FIGS. 23 and 25, is used to widen the surgical pathway 29. The relative terms "proximal" and "distal" are used herein in relation to the cannula 400, the dilator 350 and the other equipment used with the cannula 400 and dilator, in relation to the medical practitioner who inserts the cannula 400, dilator 350 and other equipment used with both into the surgical pathway 29. Accordingly, the portions of the cannula 400 and dilator 350 which are the most internal within the surgical pathway or the patient, and are therefore more farther removed from the surgeon, are referred to as "distal." The portions of the cannula 400, dilator 350 and the equipment used with both which are closest to the surgeon relative to the surgical pathway are referred to as "proximal." Additionally, the dilator 350, cannula 400 and obturator 450 are shown in exaggerated scale relative to the apparatus 20 and bladder 26 and urinary tract 24 in FIGS. 26-32, 36-38 and 40-41 for clarity of understanding.

The dilator 350 has a main body portion 352 which is generally cylindrically shaped. The body portion 352 remains outside of the exterior abdomen 30. The dilator 350 also includes a pair of spaced apart arms 354 which extend from the body portion 352 and are inserted into the surgical pathway 29. The body portion 352 includes an upper ring portion 356 from which there extend distally a pair of diametrically opposite and longitudinally extending arm receivers 358 and a pair of diametrically opposite and longitudinally extending sidewalls 360 located between the arm receivers 358. The sidewalls 360 and the arm receivers 358 are each separated circumferentially by a small gap 362. Four small gaps 362 are therefore located around the body portion 352.

The arm receivers 358 and the sidewalls 360 are integrally connected at their proximal ends with the annular ring portion 356. The annular ring portion 356 is located at proximal end of the body portion 352. The ring portion 356 includes an insertion slot 359 and an annular retention groove 361 formed adjacent to its proximal end. The insertion slot 359 and retention groove 361 are adapted to receive complementary-shaped connection fingers (not shown) of a stylet 390 (FIG.

23) and of a cannula 400 (FIG. 33) to connect those components to the dilator 350 during different stages of use discussed below. The insertion slots 359 and retention groove 361 interact with a complementary-shaped connection finger (not shown) of the stylet and the cannula to create a bayonet-style connection. Finger grips 363 protrude outwardly from the distal ends of each arm receiver 358. The finger grips 363 are useful for maintaining the dilator 350 in a generally stabilized position when the surgeon applies force with other equipment used with the dilator, as discussed below.

One of the arms 354 extends distally forward and generally parallel from each of the two arm receivers 358, as is shown in FIGS. 23, 24A and 25. The arm receivers 358 each contain a cavity 365 at their distal ends into which a proximal end of one of the arms 354 is inserted. The proximal end of each arm 354 is held in place in the cavity 365 by adhesive, after the other components associated with each arm 354 have been assembled.

The arms 354 have a generally crescent-moon shaped cross section as shown in FIG. 24B. A center cavity 364 extends along the full length of each arm 354. A window 366 (FIG. 23) extends from the outside surface of the distal end of each arm 354 into the center cavity 364.

Figure 24C:
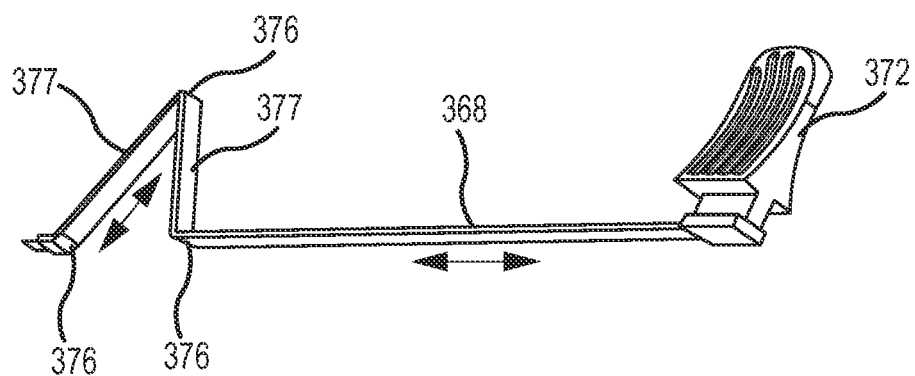
FIG. 24C is a perspective view of a longitudinal tab and wing of the dilator shown in FIG. 23, removed from the dilator with a distal portion of the longitudinal tab shown in an expanded condition.

A tab 368 extends longitudinally within and along the full length of the center cavity 364 of each arm 354. Wings 372 are located at the proximal ends of each longitudinal tab 368, as shown in FIGS. 24A and 24C. The wings 372 are preferably integrally formed with the longitudinal tabs 368, such as by molding them from plastic material as the tabs 368 are made. The wings 372 move proximally and distally within longitudinal tracks 374 formed in the exterior surfaces of the arm receivers 358.

Each tab 368 is inserted in the center cavity 364, and its distal end is connected to the distal end of the center cavity 354 by adhesive. The wing 372 is inserted in the longitudinal tracks 374 while the proximal end of the arm 354 is inserted into the cavity 365. Adhesive is applied to the exterior of the proximal end of the arm 354 to hold it in its inserted position in the cavity 365. In this manner each arm 354 is assembled to its arm receiver 358.

Figure 26:
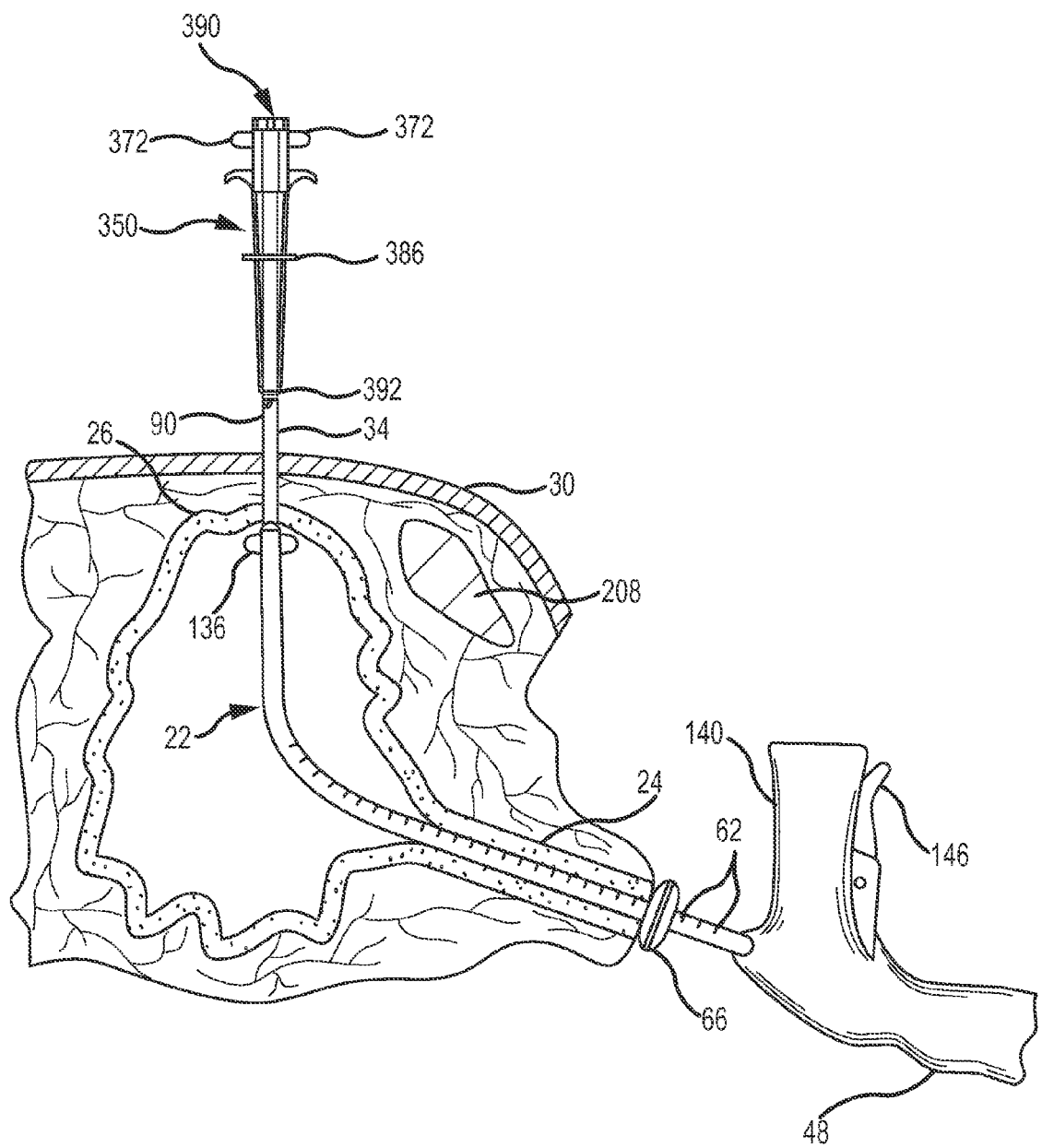
FIGS. 26-32 are partial cross-sectional and perspective views showing a series of actions involved in using the dilator and stylus shown in FIGS. 23-25 along with the apparatus shown in FIGS. 1-16 to maintain the surgical pathway completed as shown in FIG. 22, with the dilator and stylus having a greater scale in proportion to the other aspects of FIGS. 26-32. More specifically.

Stress risers 376 are located on the longitudinal tabs 368, near the distal ends 370. The stress risers 376 cause portions 377 of the longitudinal tabs 368 to deflect out through the windows 366 when the tabs 368 and the wings 372 are moved toward the distal end of the tracks 374, as shown in FIGS. 23 and 24C. Sliding the wings 372 toward the proximal end of the tracks 374 cause the portions 377 of the longitudinal tabs 368 to retract into the windows 366 as shown in FIG. 26.

Figure 24D:
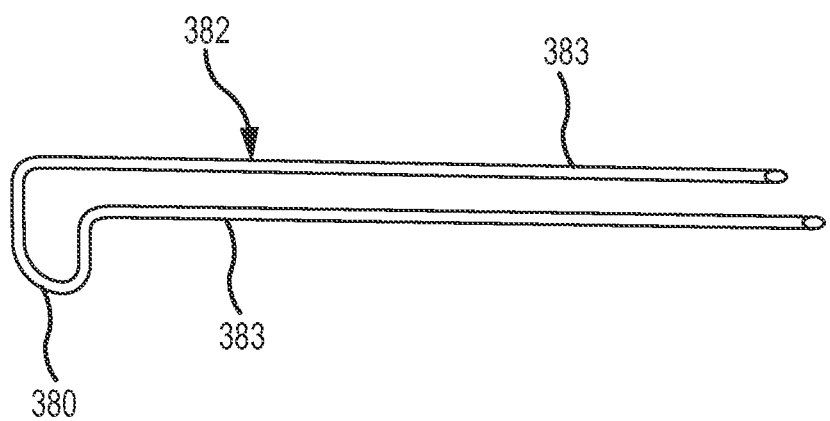
FIG. 24D is a perspective view of a wire and loop formed in the wire shown in FIGS. 23 and 24A, removed from the arm of the dilator.

Parallel side cavities 378 are formed within the arms 354 on opposite sides of the center cavity 364, as shown in FIG. 24B. The side cavities 378 extend the entire length of the arms 354. The parallel side cavities 378 hold a wire loop 380 at the distal ends of each arm 354. The wire loop 380 is formed by bending the center of a relatively long wire 382 into a right angle U-shape, as shown in FIG. 24D. The two relatively lengthy end portions 383 of the wire 382 extend from the loop 380 in a parallel relationship with one another. The end portions 383 are inserted into the side cavities 378 of each arm 354 and are held there by an adhesive. The end portions 383 of each wire 382 extend the entire length of each arm 354 within the side cavities 378. The end portions 383 of each wire 382 strengthen the arms 354 when inserted in the side cavities 378. The U-shaped portion of each wire 382 forms the wire loop 380 which protrudes inwardly from the distal end of each arm 354 toward the other arm 354, as shown in FIG. 23.

Indicia 384 are formed along the length of at least one of the arms 354, as shown in FIG. 25. The indicia 384 indicate a distance from a proximal end of the windows 366. The surgeon correlates the distance indicated by the indicia 384 with the thickness of the abdomen indicated by the indicia 206 of the mast 144 to determine when the dilator 350 is inserted within the surgical pathway 29 deeply enough to position the windows 366 within the bladder 26 to allow the portions 377 of the longitudinal tabs 368 to protrude from the windows 366 and anchor the dilator 350 in the bladder 26.

A disc-shaped flexible retention ring 386 is slidably positioned over the arms 354. A hollow center 387 through the retention ring 386 permits the arms 354 to pass through the retention ring 386. The retention ring 386 is movable along the arms 354 to abut against the external abdomen 30 when the dilator 350 is at the desired depth in the surgical pathway. Contacting the retention ring 386 against the external abdomen prevents the dilator 350 from moving into the bladder 26 from the desired position, while the expanded portions 377 of the longitudinal tabs 368 prevent the dilator 350 from moving out of the bladder 26. In this manner, the dilator retained or anchored on opposite sides of the abdominal tissue which separates the bladder 26 from the external abdomen 30.

Slight flexibility in the annular ring portion 356 of the body 352 allows the distal ends of the arm receivers 358 to be squeezed slightly toward one another, as shown in FIG. 25, allowing the distal ends of the arms 354 to move closely adjacent to one another. The wire loops 380 are slightly offset from one another in a longitudinal direction so that they overlap to jointly form an enclosure 385 (FIG. 25) when the arms 354 are our moved toward each other. A distal end of a stylet 390 (FIG. 23) is inserted through the enclosure 385 formed by the overlapping wire loops 380, as shown in FIG. 25. Holding the distal ends of the arms 354 together with a stylet 390 allows the dilator 350 to be inserted into the surgical pathway 29.

Figure 9:
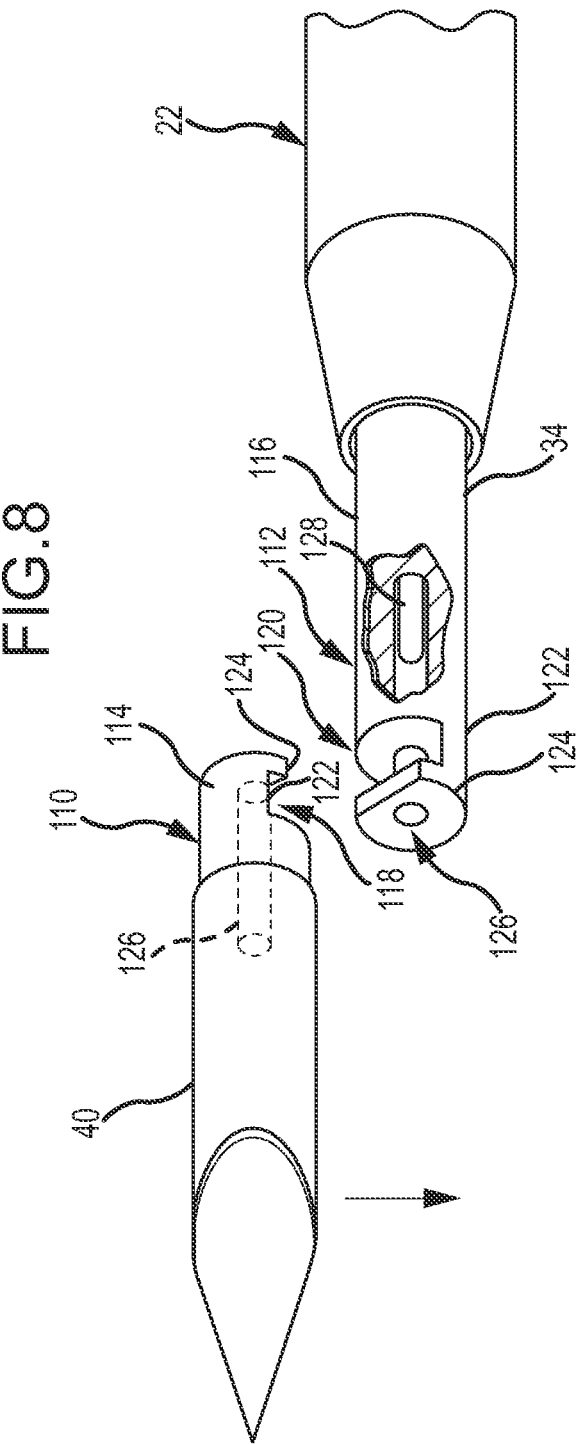
FIG. 9 is an exploded perspective view of the details of an interdigitated connection between the advancement coil and the cutting tip, which constitutes an alternative to the connection shown in FIGS. 7 and 8.

The stylet 390 includes a distal end connector 392 and a knob 394 separated by a long narrow shaft 396. The distal end connector 392 on the shaft 396 is substantially similar in shape to the bayonet style cutting tip connector 88 (FIGS. 7 and 8) of the cutting tip 40 (FIGS. 7 and 8), or to the interdigitated cutting tip connector 110 (FIGS. 9 and 10). For purposes of the following description, the distal end connector 372 is described as the bayonet connector, although the interdigitated connector could also be used as an alternative. The bayonet connector 392 is intended to be connected to the advancement device connector 90 (FIGS. 7 and 8) of the advancement coil 35 (FIG. 7). The shaft 396 is relatively rigid so that it may transfer rotational force from the knob 394 to the bayonet connector 392.

The stylet 390 is attached to the dilator 350 as shown in FIG. 25 by inserting the shaft 396 through an annular opening 398 in the ring portion 356 of the dilator body 352. Continued insertion of the stylet 390 into the dilator 350 while pressing the arm receivers 358 inward positions the shaft 396 between the spaced apart arms 354 and through the enclosing wire loops 380 at the distal ends of the arms 354, thus securing the distal ends of the arms 354 against the shaft 396.

The bayonet connector 392 and a short distal part of the shaft 396 extend distally beyond the overlapped wire loops 380. The wire loops 380 retain the distal ends of the arms 354 close to the shaft 396. Maintaining the distal ends of the arms 354 close to the shaft 396 facilitates insertion of the dilator 350 into the surgical pathway 29 by minimizing the cross sectional area of the dilator 350 and by preventing the distal ends of the arms 354 from projecting into the tissue surrounding the surgical pathway.

The interior of the knob 394 is hollow and is adapted to connect to the proximal ring portion 356 of the main body 352 of the dilator 350 (FIG. 25). The interior of the knob 394 includes two diametrically opposite and radially inward projecting connection fingers (not shown) which are adapted to be inserted within the insertion slots 359 and to be rotated within the retention groove 361 of the ring portion 356 (FIG. 23) in a bayonet-style connection manner to hold the stylet 390 within the dilator 350.

The bayonet connector 392 is connected to the advancement device connector 90, as shown in FIG. 26. The bayonet connector 392 connects to the advancement device connector 90 in the same manner as the cutting tip connector 88 connects to the advancement device connector 90 (FIGS. 7 and 8). The opening 228 in the annular housing 222 (FIG. 16B), or the gap 205 between the forks 202 (FIG. 16A), permits the mast 144 and guide arm 154 (or 198) to be removed and set aside after the connected dilator 350 and stylet 390 are attached to the advancement coil 35. Otherwise the mast 144 and the guide arm 154 (FIG. 1) must be removed and set aside before the connected-together stylet 390 and dilator 350 are connected to the advancement device connector 90. The retention ring 386 is moved far enough up the arms 354 in the proximal direction to ensure that the retention ring 386 does not interfere with the insertion of the dilator 350 to a desired depth within the surgical pathway 29.

Figure 27:
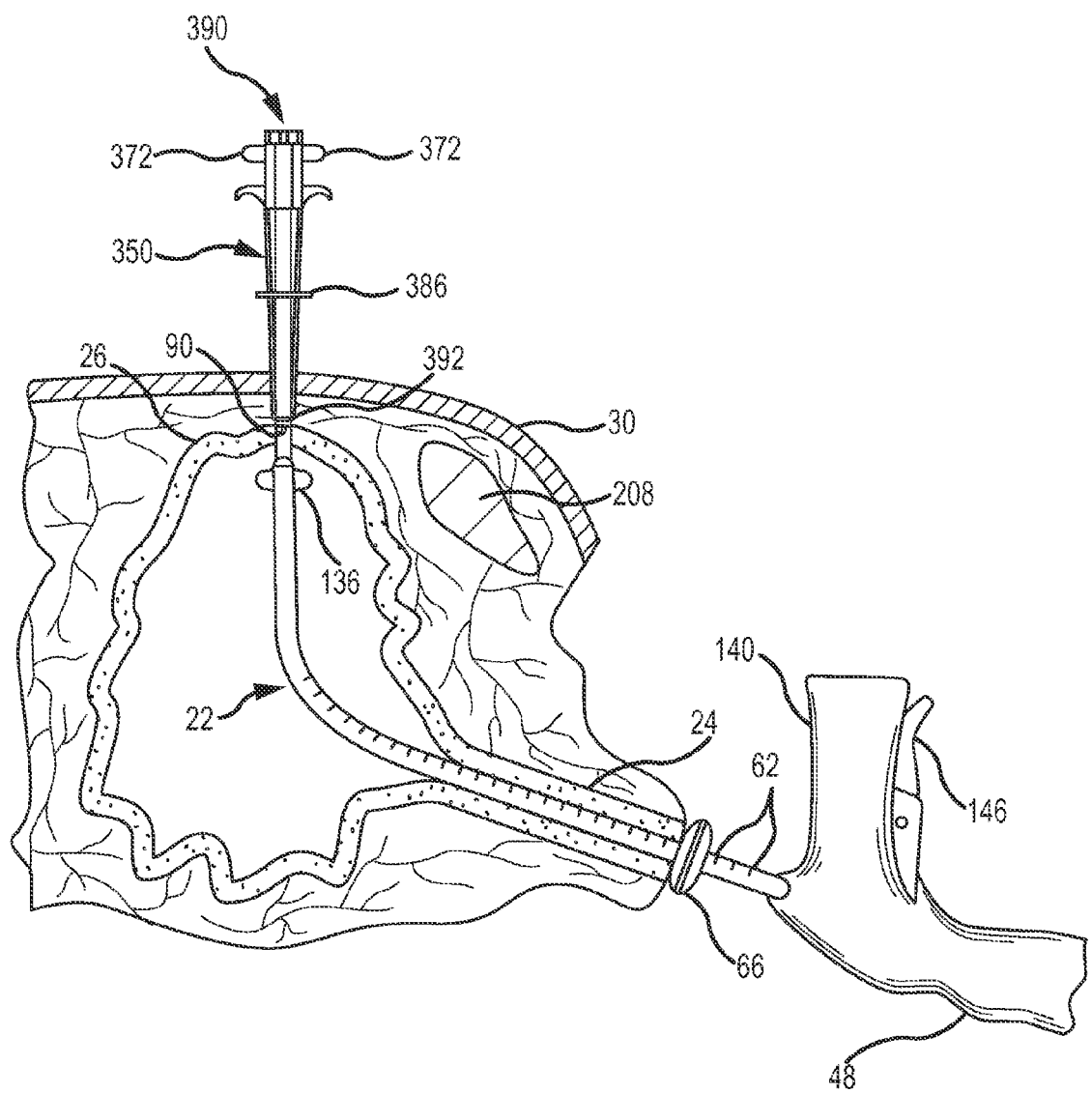

After the connectors 392 and 90 are connected, the surgeon moves the rear handle 50 (FIGS. 1 and 2) rearwardly or proximally away from the front handle 48 to retract the advancement device 34. The retraction of the advancement device 34 moves the connected stylet 390 and dilator 350 into the surgical pathway 29, as shown in FIG. 27.

Figure 28:
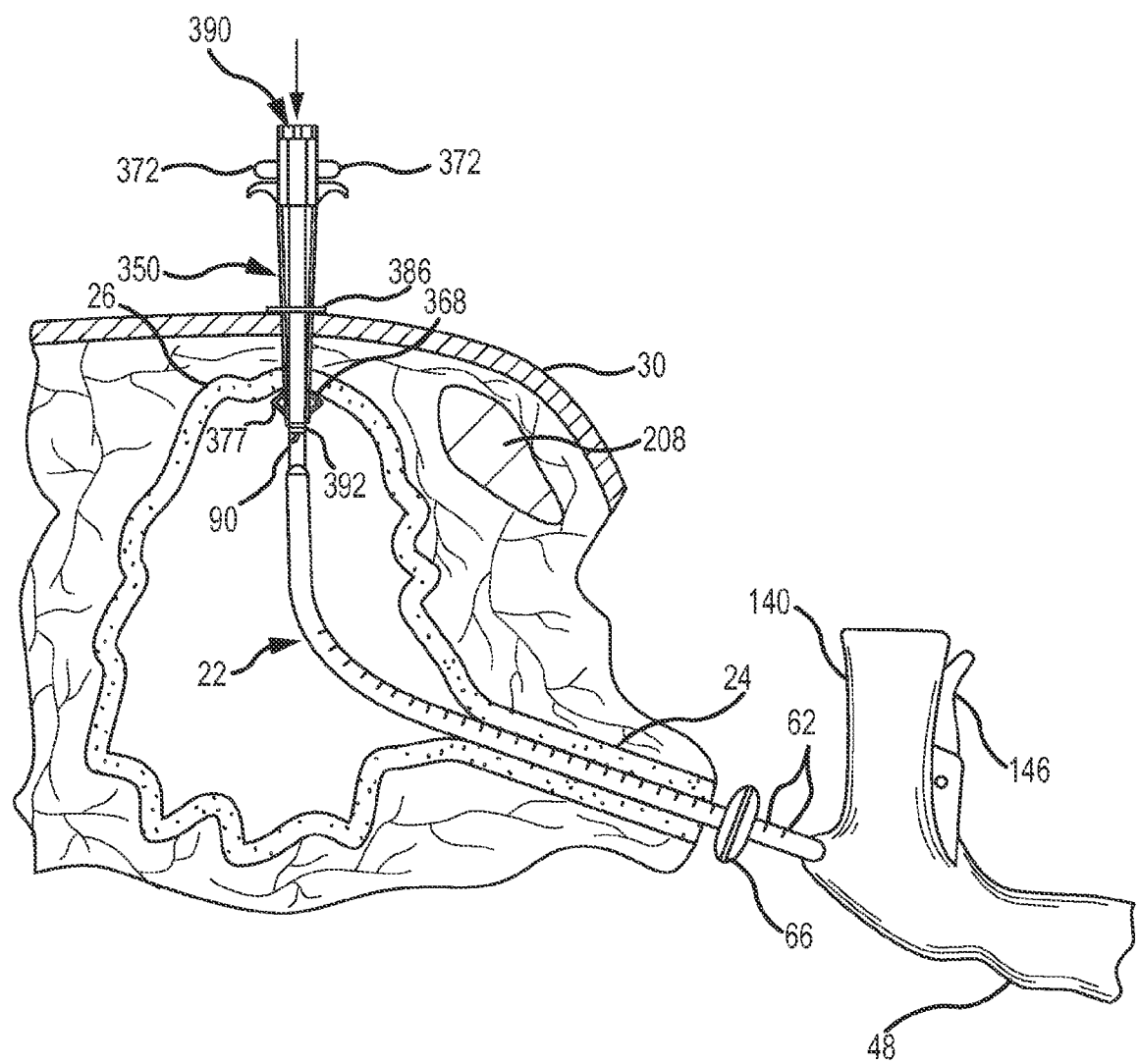

While or after retracting the advancement device 34, the distal end 28 of the sound 22 is moved away from the bladder 26, as shown in FIG. 28. The inflatable balloon 136 (FIGS. 26 and 27) may also be collapsed at this time.

Figure 29:
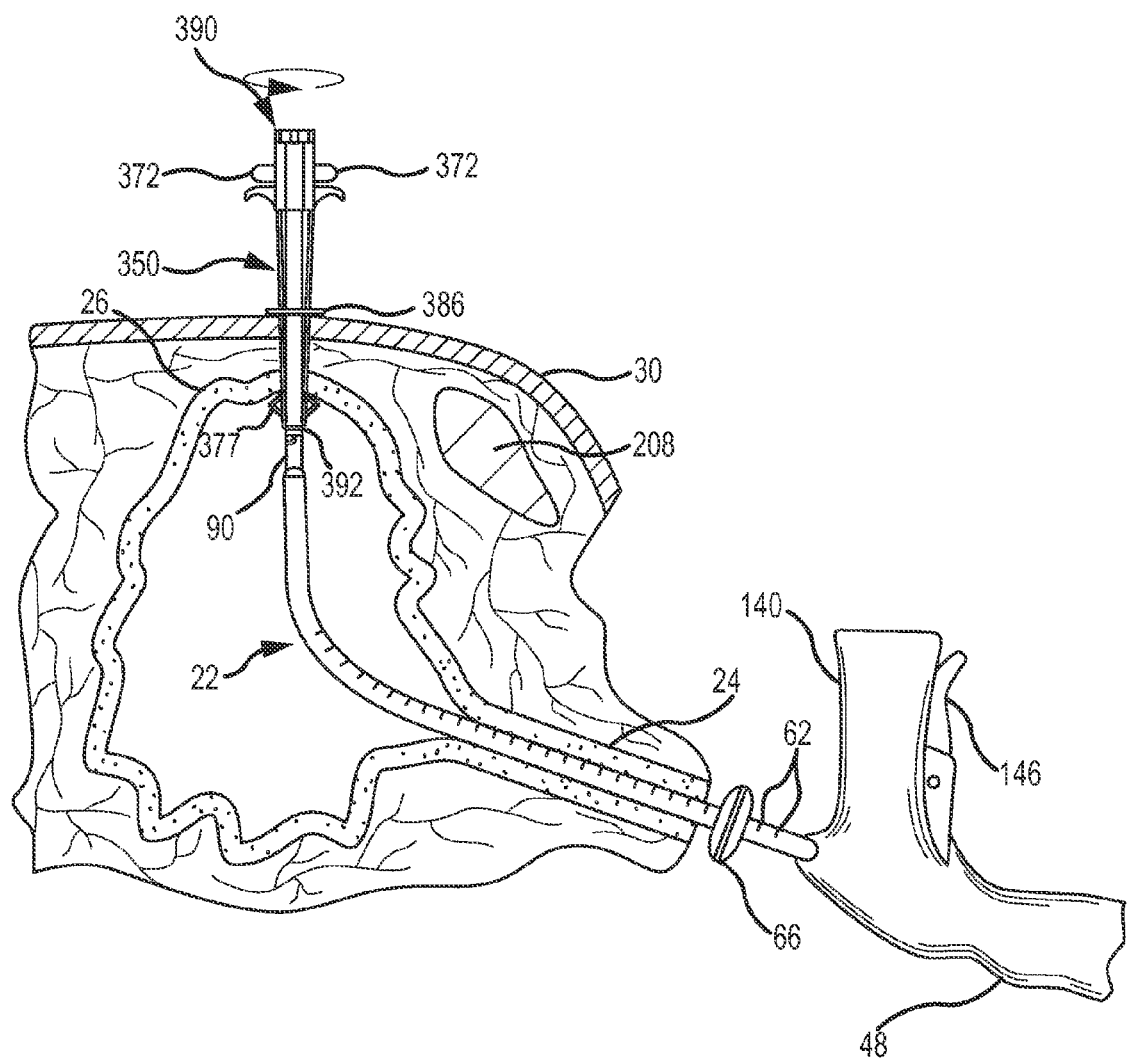

The combined retraction of the advancement device 34 and the sound 22 moves the distal ends of the connected dilator 350 and stylet 390 sufficiently into the bladder to position the windows 366 (FIG. 25) in the arms 354 in the bladder 26, as shown in FIG. 29. The indicia 384 (FIG. 25) on the arms 354 indicate the distance within the surgical path 29 that the dilator 350 has been inserted. The distance of insertion of the dilator 350 should be greater than the thickness of the tissue between the bladder 26 and the external abdomen 30, as earlier determined by reference to the indicia 206 on the mast 144, in order to locate the windows 366 within the bladder 26. After the dilator 350 has been inserted into the surgical pathway 29 to the desired depth, the retention ring 386 is moved down the arms 354 to abut against the external abdomen 30 and anchor the dilator 350 against further distal movement into the bladder 26.

After the dilator 350 has been inserted into the surgical pathway 29 as shown in FIG. 29, the surgeon presses downward on the wings 372 to expand the longitudinal tabs 368 from the windows 366 (FIG. 25). The protrusion of the tabs 368 from the windows 366 contacts the inner wall of the bladder 26 adjacent to the surgical pathway 29 and thereby anchors the dilator 350 in the surgical pathway. Anchoring the dilator 350 in this manner prevents it from unintended withdrawal from the surgical pathway.

Figure 30:
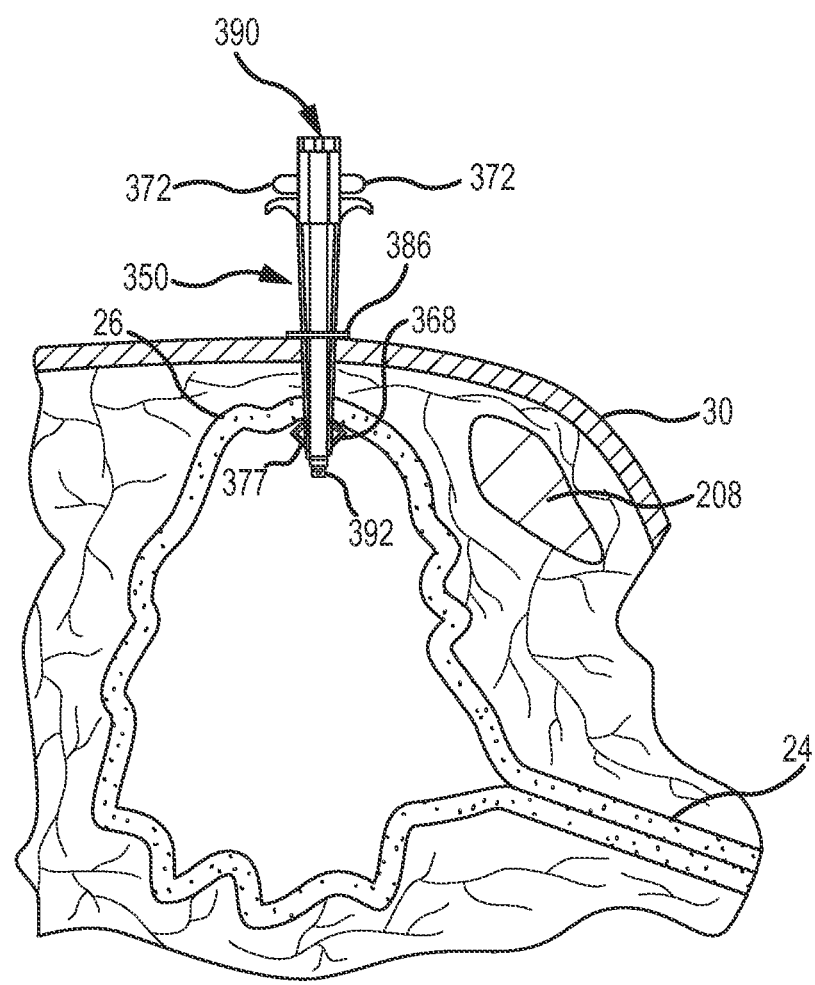

After the dilator 350 has been anchored, the knob 394 of the stylet 390 is rotated sufficiently to disconnect the bayonet connector 392 from the advancement device connector 90 thereby disconnecting the stylet 390 from the advancement coil 35 (FIG. 7), as shown in FIG. 29. After the stylet 390 has been disconnected from the advancement coil 35 after the dilator 350 has been anchored in the bladder, the sound 22 is removed from the urinary tract 24, as shown in FIG. 30.

Figure 31:
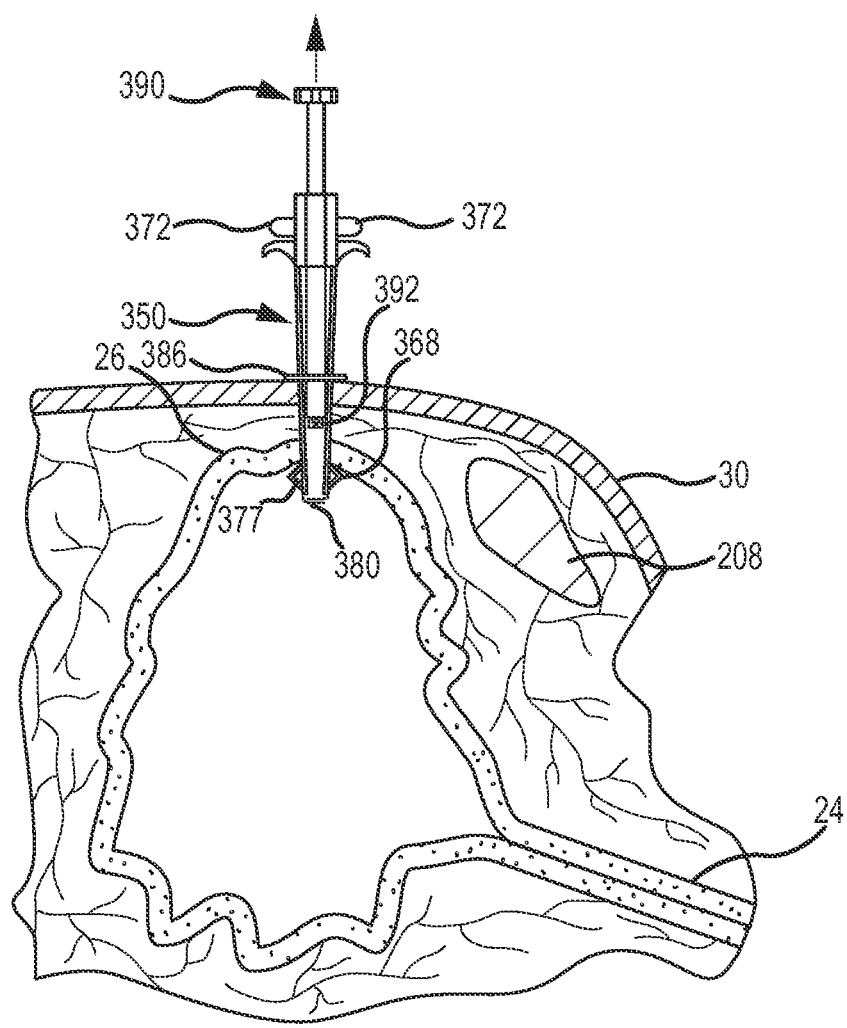
Figure 32:
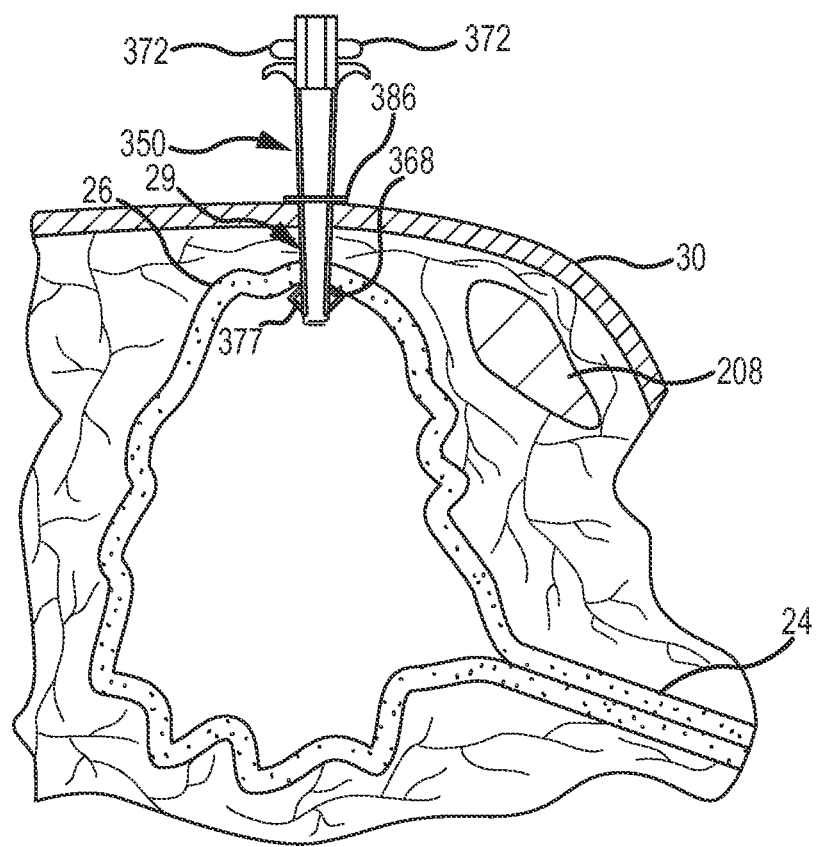

The stylet 390 is then removed from the dilator 350 by rotating the knob 394 relative to the ring portion 356 of the main body 352, thereby disconnecting the bayonet-style connection formed by the internal fingers within the knob 394 (not shown) and the insertion slot 359 and retention groove 361 (FIG. 23). The shaft 396 is then withdrawn from the annular opening 398 in the annular ring portion 356 of the main body 352, as shown in FIG. 31. Removing the stylet 390 in this manner leaves only the dilator 350 in the surgical pathway 29 (FIG. 32).

Figure 33:
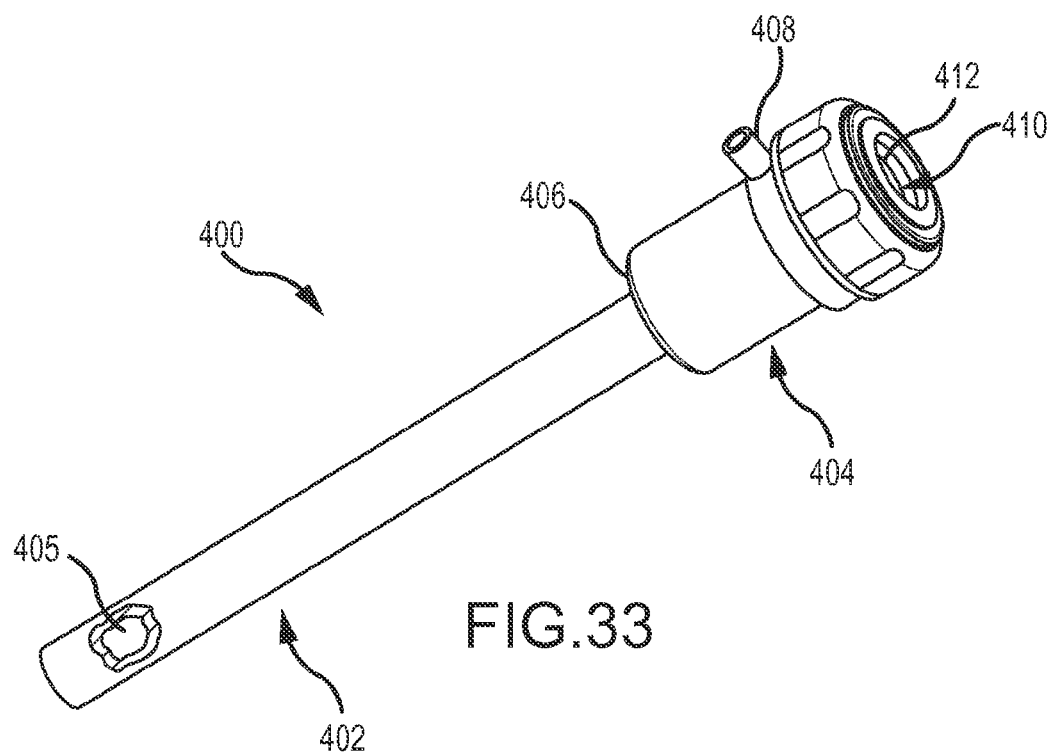
FIG. 33 is a perspective view of a cannula of the present invention used in conjunction with the dilator shown in FIGS. 23-32.
Figure 34:
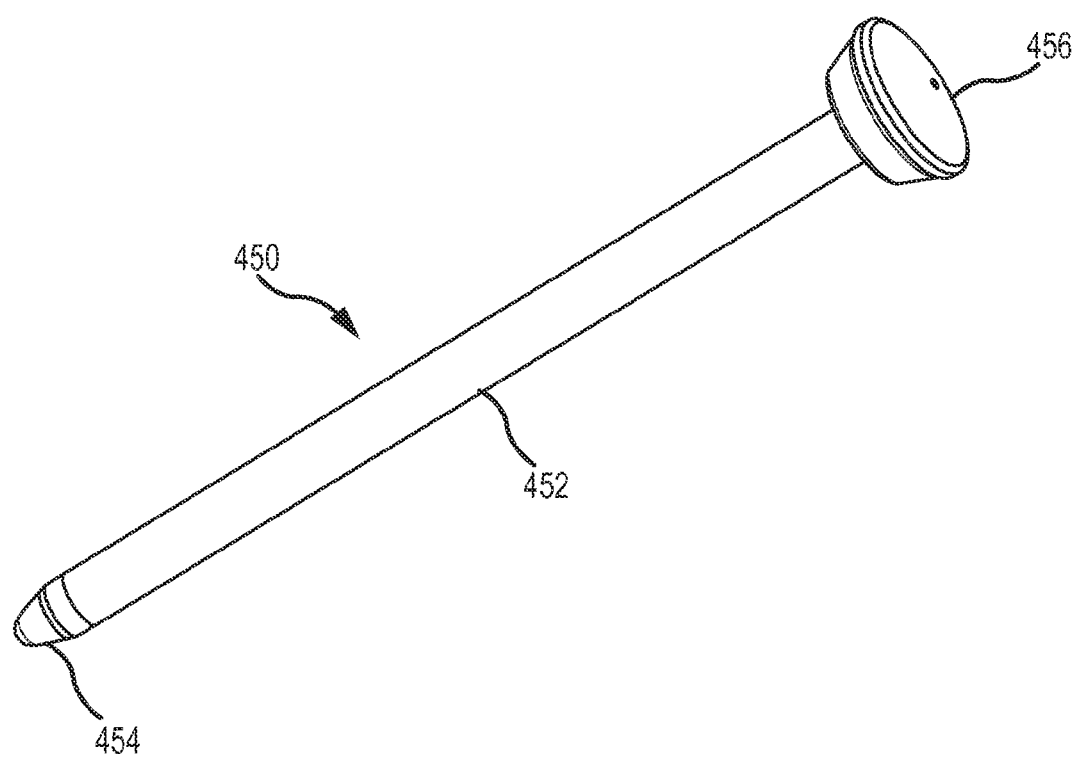
FIG. 34 is a perspective view of an obturator of the present invention used in conjunction with the cannula shown in FIG. 33 to insert the cannula into the dilator shown in FIG. 23.
Figure 35:
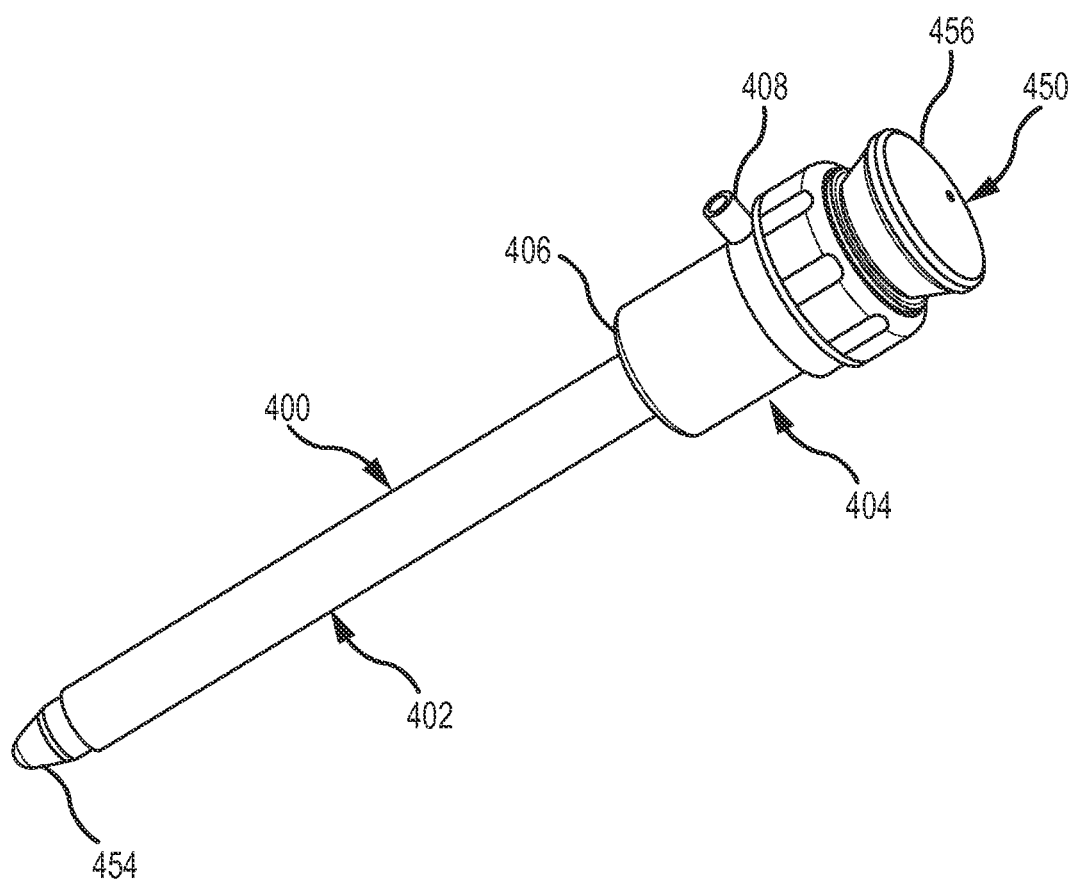
FIG. 35 is a perspective view of the cannula shown in FIG. 33 into which the obturator shown in FIG. 34 has been inserted and connected.
Figure 36:
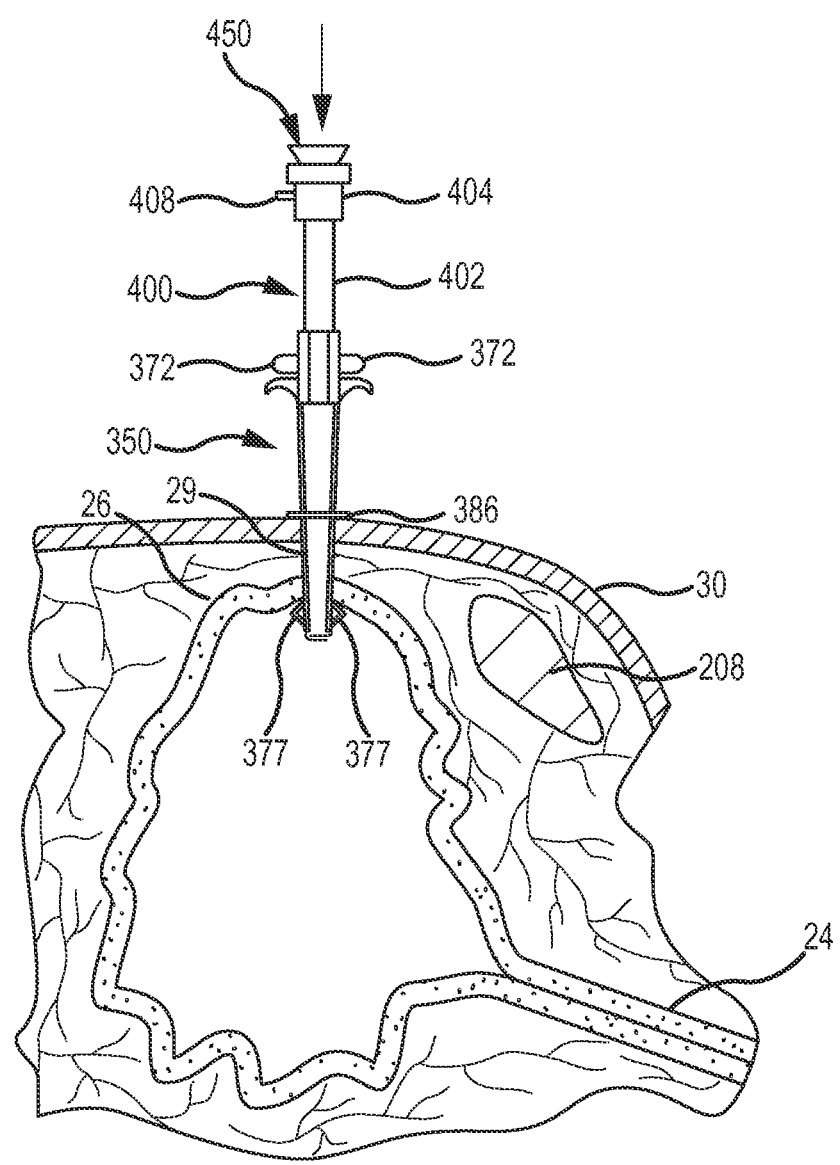
FIGS. 36-38 are partial cross-sectional and perspective views showing a series of actions involved in inserting the cannula and obturator shown in FIGS. 33-35 into the dilator shown in FIGS. 23 and 32 to expand the surgical pathway, with the cannula, obturator and dilator having a greater scale in proportion to the other aspects of FIGS. 36-38. More specifically.
Figure 37:
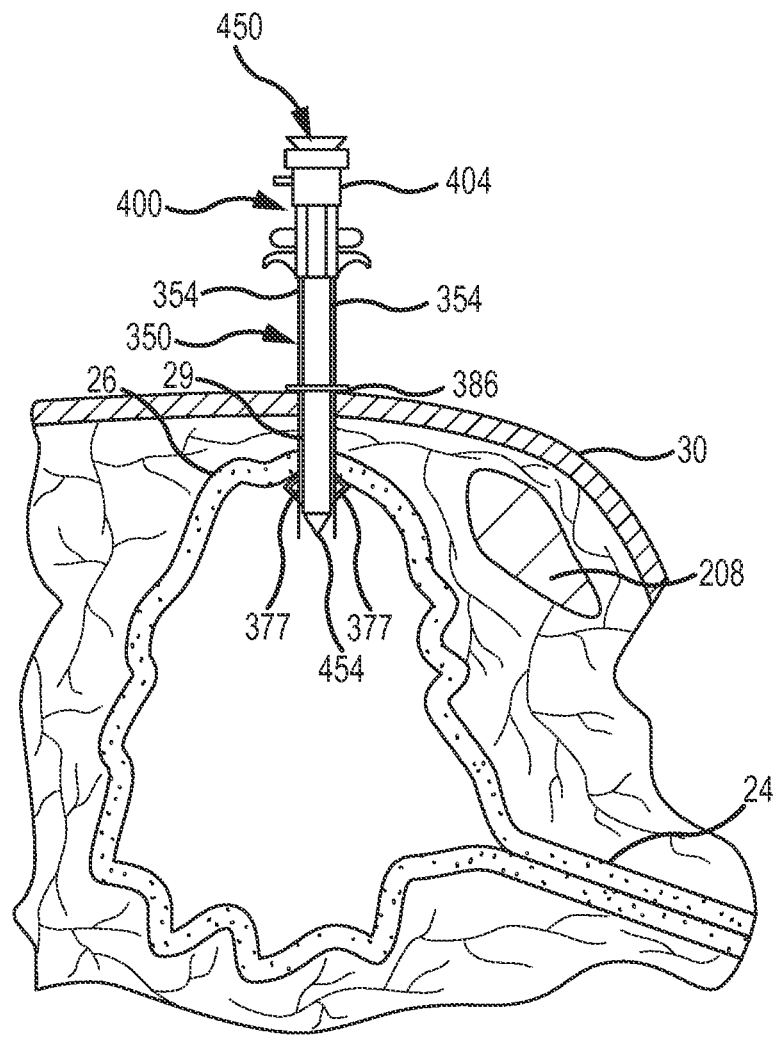

With the dilator 350 successfully inserted and anchored in the surgical pathway 29, a cannula 400, shown in FIG. 33 and an obturator 450, shown in FIG. 34, which are connected together as shown in FIG. 35, are then jointly inserted while connected together into the dilator 350. The insertion of the connected together cannula 400 and obturator 450 into the dilator 350 expands the surgical pathway 29 (FIGS. 36-37).

Figure 39:
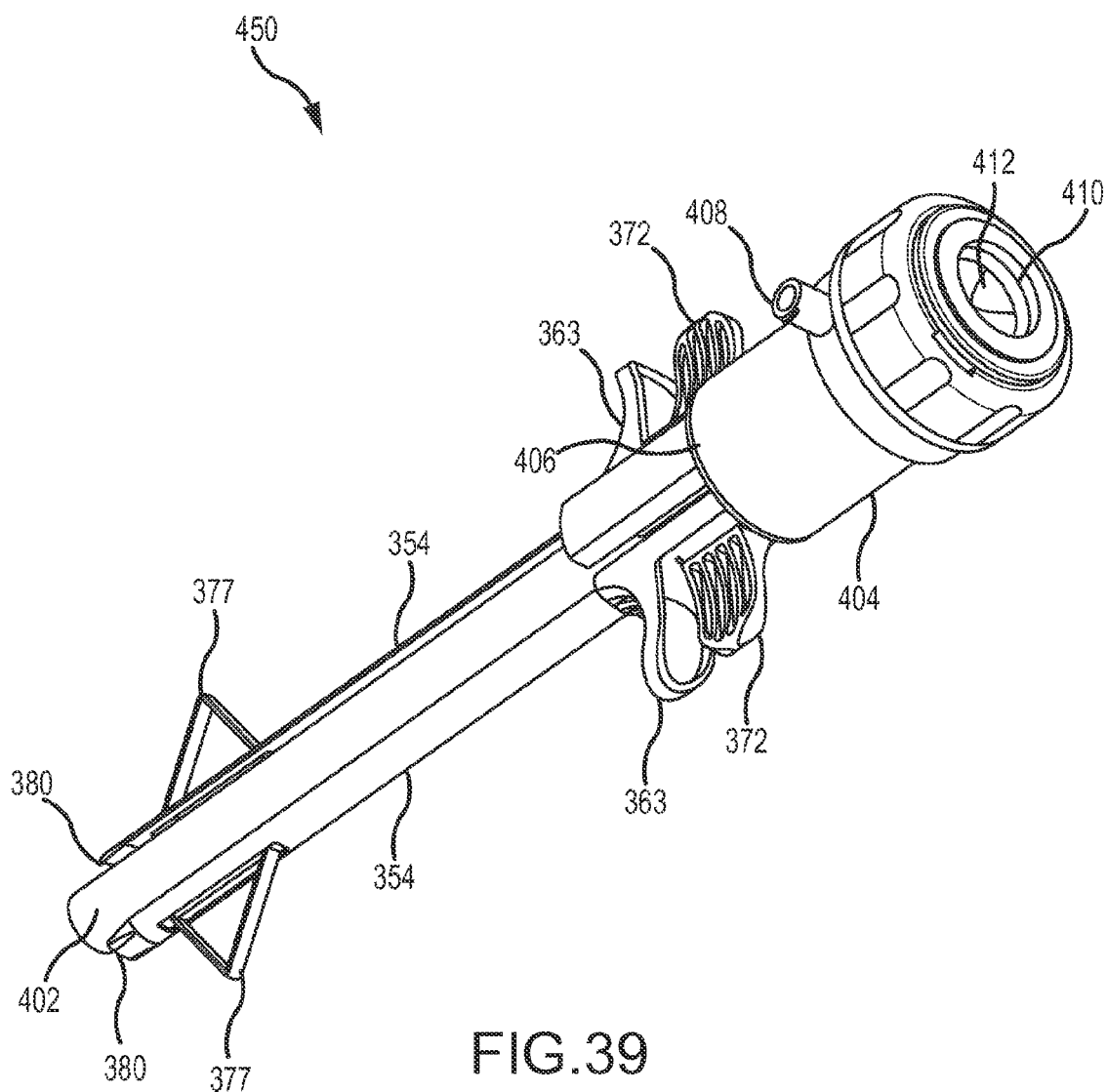
FIG. 39 is a perspective view of the cannula within the dilator after the obturator has been removed, in the condition shown in FIG. 38.

The cannula 400, shown in FIG. 33, includes a hollow tube portion 402 and a hollow body portion 404. A center passageway 405 extends completely along the length of the cannula 400. A distal part 406 of the body portion 404 is hollow at the exterior of the tube portion 402 and is adapted to connect to the proximal ring portion 356 of the main body 352 of the dilator 350 (FIGS. 23 and 39). The interior of the distal part 406 includes two diametrically opposite and radially inward projecting connection fingers (not shown) which are adapted to be inserted within the insertion slots 359 and to be rotated within the retention groove 361 of the ring portion 356 (FIG. 23) in a bayonet-style connection manner to hold the cannula 400 within the dilator 350.

Figure 41:
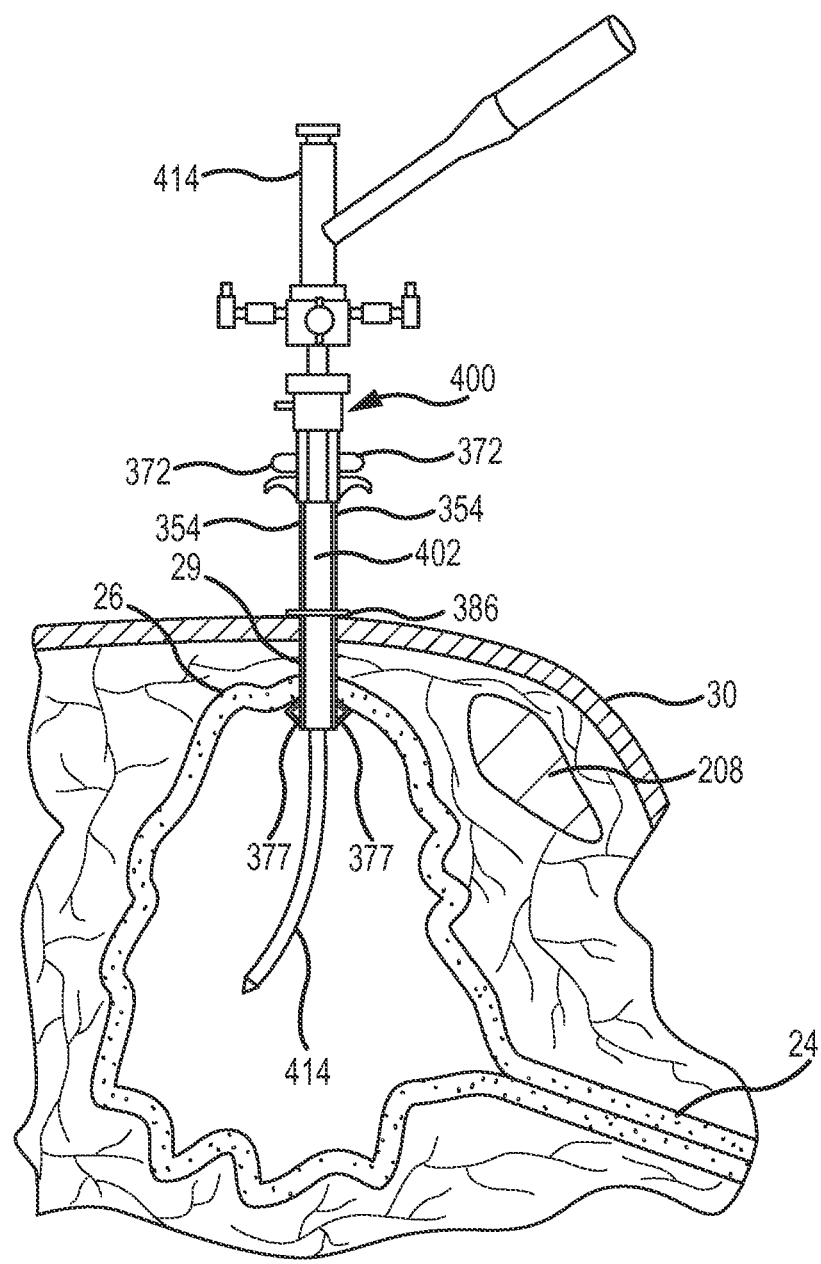
FIG. 41 is a partial cross-sectional and perspective illustration of inserting a medical instrument into the cannula connected to the dilator as illustrated in FIG. 40.

The body portion 404 also includes a fluid port 408 which communicates with the center passageway 405 of the tube portion 402. The fluid port 408 is used to flush fluid into the bladder 26 during a medical procedure, if desired by the surgeon, when the cannula 400 is connected to the dilator 350 and located in the surgical pathway. The body portion 404 also includes a opening 410 by which to access the interior passageway 405 extending through the dilator 400. A conventional dome seal 412 extends across the opening 410 to seal the opening 410 when no medical instrument is inserted through the opening 410. The dome seal 412 includes at least one slit which allows the dome seal 412 to separate sufficiently to accept a medical instrument 414 inserted therethrough into the cannula 400 and bladder 26 (FIG. 41). The dome seal 412 also collapses around the inserted medical instrument 414 to retard the flow of fluid from the bladder through the tube portion 402. A conventional pressure seal (not shown) is also included within the tube portion 402 of the cannula 400 to seal the interior passageway 405 against a medical instrument is inserted through the cannula 400 (FIG. 41).

The obturator 450, shown in FIG. 34, has a cylindrical shaft 452 which extends distally to a tapered and rounded distal end 454. A push cap 456 extends from the proximal end of the cylindrical shaft 452. The obturator 450 is used to assist the insertion of the cannula 400 (FIG. 33) into the dilator 350 (FIG. 23).

The tapered distal end 454 and the shaft 452 of the obturator 450 is inserted through the dome seal 412 and the cylindrical opening 410 and into the interior passageway 405 of the cannula 400. The shaft 452 is pushed into the passageway 405 until the push cap 456 abuts the body portion 404 of the cannula 400, and the tapered distal end 454 extends distally beyond the distal end of the tube portion 404 of the cannula 400, as shown in FIG. 35.

The combined cannula 400 and obturator 450 are then inserted into the dilator 350 by inserting the tapered distal end 454 into the annular opening 398 in the ring portion 356 of the dilator body 352, as shown in FIG. 36. The surgeon pushes on the push cap 456 while holding the dilator 350 steady at the finger support groups 363 (FIG. 23) to force the cannula 400 and obturator 450 into the dilator 350. As the combined cannula 400 and obturator 450 are inserted into the dilator 350, the arms 354 are pushed outward by a camming effect from the tapered point 454 against the arms 354. The arms move from the inwardly bowed in orientation (FIG. 25) to an outward parallel orientation (FIGS. 23 and 37). The tapered distal end 454 gently forces the arms 354 of the dilator 350 apart from one another while simultaneously enlarging the transverse width of the surgical pathway 29. The degree of taper and curvature of the distal end 454 causes the tissue surrounding the surgical pathway to expand elastically. The wire loops 380 of the dilator 350 deflect laterally to the outside of the cannula 400 as the connected cannula 400 and obturator 450 move between the distal ends of the arms 354.

Figure 38:
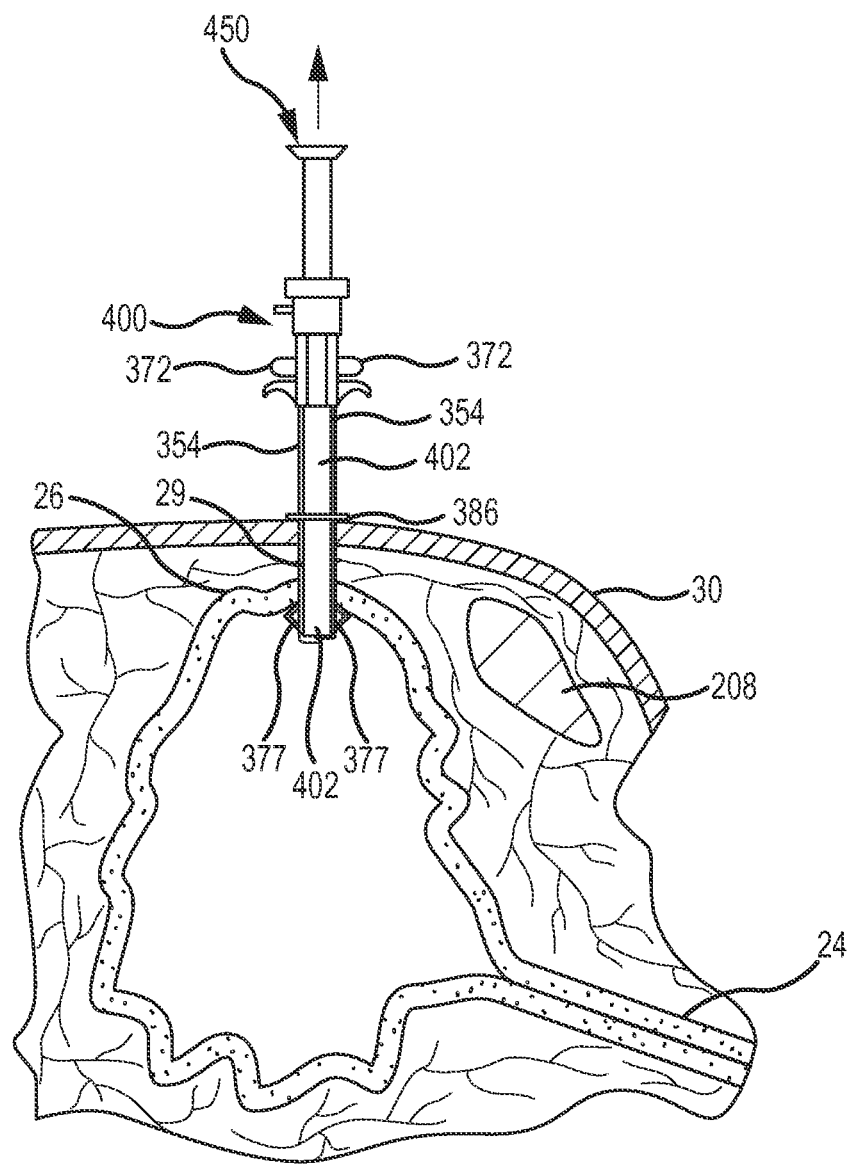
Figure 40:
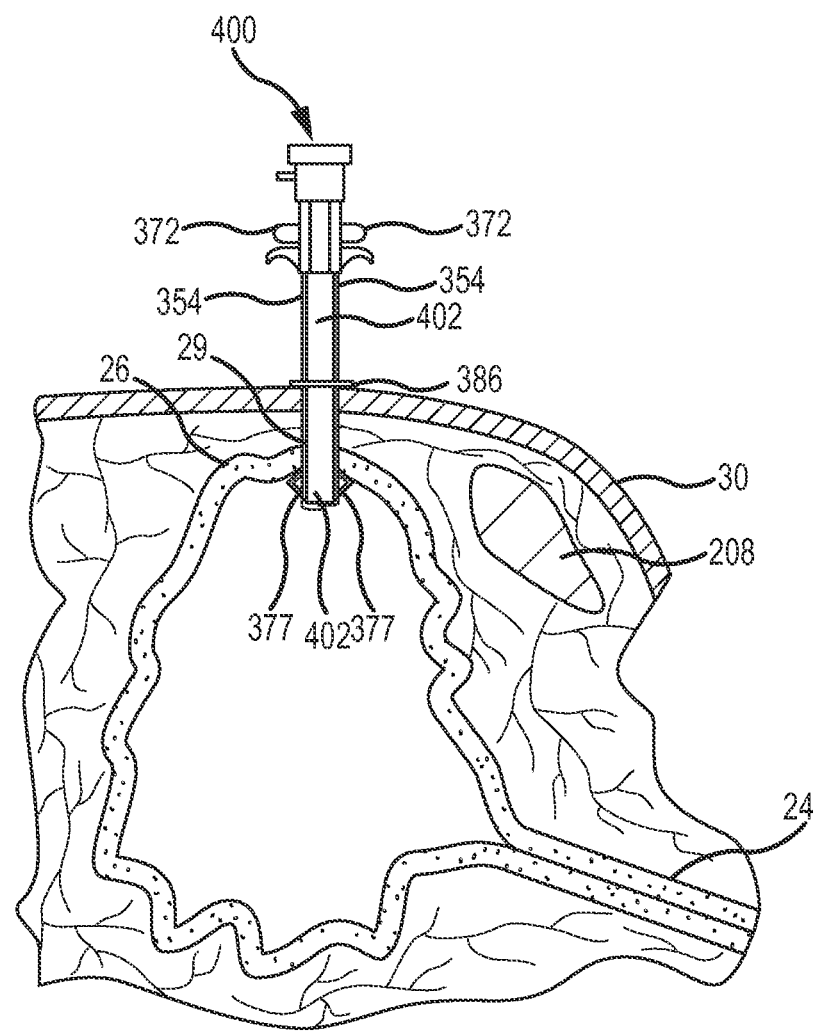
FIG. 40 is a partial cross-sectional and perspective illustration showing the cannula within the dilator as illustrated in FIG. 39 in a condition of use.

After the connected cannula 400 and obturator 450 are fully inserted into the dilator 350, as shown in FIG. 37, the cannula 400 and dilator 350 are attached to each other by engaging inside bayonet-style connection at the distal end of the distal part 406 of the body portion 404 (not shown), with the insertion slot 359 and retention groove 361 of the ring portion 356 of the dilator 350 (FIG. 23). In this manner, the cannula 400 is firmly connected to the dilator 350, and the dilator 350 is firmly anchored in the bladder by the protruding deflection portions 377 of the longitudinal tabs 368 (FIG. 39). The obturator 450 is then removed from the cannula 400, as shown in FIG. 38, leaving the connected dilator 350 and cannula 400 in the surgical pathway as shown in FIGS. 39 and 40.

The cylindrical opening 410 and interior passageway 405 of the cannula 400 provide access into the bladder 26 for medical instruments 414 inserted through the dome seal 412, as shown in FIG. 41. The medical instruments are manipulated from the outside of the patient to perform medical procedures within the bladder 26.

The cannula 400 and dilator 350 remain in place for the duration of the medical procedure. To remove them after the procedure is complete, the cannula 400 is disconnected from the main body 352 of the dilator 350, by twisting and unlocking the bayonet-style internal connection between the distal end of the park 406 and the slots 359 and retention grooves 361 on the annular ring 356 of the body 352 of the dilator 350 (FIG. 23). The cannula 400 is then withdrawn from the dilator 350 in the opposite direction from which it was inserted. The wings 372 are moved proximally in their tracks 374, causing the deflection portions 377 of the longitudinal tabs 368 to retract from their extended position into the windows 366 and the center cavity 364 of the arms 354. The arms 354 are free to move together, and the wire loops 380 are free to overlap each other. The arms 354 are withdrawn from the surgical pathway 29 by pulling the dilator 350 out of the surgical pathway away from the external abdomen 30 using the finger support groups 363 (FIG. 23). The surgical pathway 29 collapses after removal of the dilator 350. The natural bodily healing process seals the surgical pathway with time.

In the manner described above, the cystotomy apparatus 20 is used effectively to create the surgical path 29, while providing the surgeon with improved control to locate the surgical path as desired and to create the surgical path efficiently with minimum of trauma to the patient. The dilator 350, which is used in connection with the stylet 390 and the cystotomy apparatus 20, is effectively drawn into the surgical pathway to maintain that pathway. The cannula 400 and the obturator 450 are readily inserted through the dilator to expand the surgical pathway sufficiently to accept the cannula 400 without tearing the surgical pathway and inducing additional trauma to the patient. Removal of the obturator 450 from within the cannula 400 leaves a pathway for 05 through the cannula 400 which readily accepts medical instruments 414 to execute a desired medical procedure.

Features of the cystotomy apparatus 20, the dilator 350, the stylet 390, the cannula 400 and the obturator 450 interact in a complementary manner which facilitates the effective execution of the medical procedure. Many other advantages and improvements will be apparent upon fully appreciating the many significant aspects of the invention described above.

Presently preferred embodiments of the invention have been described with a degree of particularity. This description is of preferred examples of implementing the invention, and is not necessarily intended to limit the scope of the invention. The scope of the invention is defined by the following claims.

What is claimed:

1. A dilator for inserting a cannula into a surgical pathway extending between a bladder and an external abdomen, comprising:
   a body which is located outside of the abdomen, the body including a ring portion which defines a central opening about a central axis through which the cannula is inserted;
   a plurality of arm receivers connected to the ring portion on opposite sides of the central axis;
   a plurality of substantially straight and elongated arms for insertion into the surgical pathway, each arm connected to and extending distally from one arm receiver, each arm having a central passageway which extends substantially along the length of the arm, each arm defining a window into the central passageway facing outward from the central axis at a position adjacent to the distal end of the arm;
   a longitudinal tab member positioned within the central passageway of each arm, the longitudinal tab member extending from a distal end located at the distal end of the arm past the window to a proximal end located in the arm receiver;
   a wing member attached to the proximal end of the longitudinal tab member, the wing member movably positioned in a longitudinally extending slot formed in the arm receiver, the wing member movable in the slot in distal and proximal directions to move the portion of the longitudinal tab member which is proximal to the window in distal and proximal directions within the central passageway;
   a portion of the longitudinal tab member adjacent to the window including stress risers adjacent to deflection portions of the longitudinal tab member, the stress risers directing the deflection portions to protrude outwardly through the window upon longitudinal distal movement of the longitudinal tab member by the wing member and to withdraw the deflection portions into the window upon longitudinal proximal movement of the longitudinal tab member by the wing member;
   the central passageway of each arm extending substantially straight between the window and the proximal end of each arm; and
   the proximal and distal movement of the wing member in the slot occurring in substantially straight alignment with the portion of the longitudinal tab member extending in the center passageway of each arm.

2. A dilator as defined in claim 1, further comprising:
indicia formed at intervals along at least one arm to indicate the depth of movement of the dilator into the surgical pathway.

3. A dilator as defined in claim 1, further comprising:
a loop connected at each distal end of each arm on opposite sides of the central axis;
each loop extending toward the central axis;
the loops at the end of the arms occupying respectively different positions to allow the loops to overlap upon transverse inward deflection of each arm to the central axis.

4. A dilator as defined in claim 3, further comprising in combination a stylet, wherein the stylet comprises:
a shaft having a longitudinal length that is greater than the length of the arms of the dilator;
a stylet connector formed on a distal end of the shaft, the stylet connector adapted to releasably connect with a complementary connector of a device located in the surgical pathway; and
the shaft extending through the center opening along the central axis with the distal end of the shaft of the stylet extending through the overlapped loops on the distal ends of the arms to hold the arms deflected transversely inwardly during insertion of the dilator in the surgical pathway.

5. A dilator in combination with the stylet as defined in claim 4, wherein:
each arm includes side cavities formed on opposite transverse sides of the central passageway; and
each loop is formed by a wire curved in the form of a loop having ends extending into the side cavities of the arm to which the loop is connected.

6. A dilator in combination with the stylet as defined in claim 5, wherein:
the ends of each wire extend substantially the entire length of each arm.

7. A dilator in combination with the stylet as defined in claim 4, wherein:
the ring portion includes a connector surrounding the center opening;
the shaft of the stylet includes a knob at a distal end; and
the knob includes a complementary connector for connecting with the connector on the ring portion upon insertion of the stylet through the center opening and the distal end of the shaft through the overlapped loops.

8. A dilator in combination with the stylet as defined in claim 7, wherein:
the complementary connectors between the knob and the ring portion, and the complementary connectors between the distal end of the shaft and the device in the surgical pathway, release from one another by movement of the knob relative to the ring portion.

9. A dilator in combination with a cannula as defined in claim 1, wherein:
the cannula comprises a cannula tube which defines an internal passageway for inserting and manipulating medical instruments; and further comprising:
an obturator comprising an obturator shaft adapted to be removably received within the internal passageway of the cannula tube, the obturator shaft having a distal end of tapered and rounded shape which protrudes beyond the distal end of the cannula tube; and wherein:
the center opening of the dilator receives the cannula tube and the obturator inserted within the cannula tube, the arms of the dilator operatively expanding transversely to accommodate the cannula tube and the obturator shaft as the cannula and the obturator move distally into the center opening of the dilator, the expansion of the arms to accept the cannula and the obturator expanding the surgical pathway.

10. A dilator in combination with the cannula, as defined in claim 9, wherein:
the ring portion includes a connector surrounding the center opening;
the cannula includes a distal body portion through which the cannula tube extends;
the distal body portion of the cannula includes a complementary connector for connecting with the connector on the ring portion upon insertion of the cannula through the center opening of the dilator.

* * * * *